US012779036B2

(12) United States Patent
Marigowda et al.

(10) Patent No.: US 12,779,036 B2
(45) Date of Patent: Nov. 3, 2026

(54) COMBINATION THERAPY FOR THE TREATMENT OF CANCER

(71) Applicant: BICARA THERAPEUTICS INC., Cambridge, MA (US)

(72) Inventors: Shivakumar Bhadravathi Marigowda, Shivamoga (IN); Madhukara A R, Yelahanka New-Town (IN); Prashant Kumar Pandey, Uttar Pradesh (IN); Srinivas Reddy Boreddy, Bangalore (IN); Pradip Nair, Bangalore (IN)

(73) Assignee: BICARA THERAPEUTICS INC., Cambridge, MA (US)

( * ) Notice: Subject to any disclaimer, the term of this patent is extended or adjusted under 35 U.S.C. 154(b) by 664 days.

(21) Appl. No.: 18/256,761

(22) PCT Filed: Dec. 15, 2021

(86) PCT No.: PCT/US2021/010067

§ 371 (c)(1),
(2) Date: Jun. 9, 2023

(87) PCT Pub. No.: WO2022/132202

PCT Pub. Date: Jun. 23, 2022

(65) Prior Publication Data

US 2024/0082394 A1 Mar. 14, 2024

(30) Foreign Application Priority Data

Dec. 15, 2020 (IN) ............................ 202011054571

(51) Int. Cl.

*A61K 39/395* (2006.01)
*A61K 38/17* (2006.01)
*A61K 39/00* (2006.01)
*A61P 35/00* (2006.01)

(52) U.S. Cl.

CPC ........ *A61K 39/3955* (2013.01); *A61K 38/179* (2013.01); *A61K 39/001103* (2018.08); *A61P 35/00* (2018.01); *A61K 2039/505* (2013.01)

(58) Field of Classification Search

CPC .......... A61K 2039/54; A61K 2039/545; A61K 38/1793; C07K 2317/24; C07K 16/2818; C07K 16/2863; C07K 2319/33; C07K 2319/70; C07K 14/71

See application file for complete search history.

(56) References Cited

U.S. PATENT DOCUMENTS 5,977,316 A 11/1999 Chatterjee et al.
6,046,157 A 4/2000 Lin et al.
6,808,710 B1 10/2004 Wood et al.
7,488,802 B2 2/2009 Collins et al.
8,008,449 B2 8/2011 Korman et al.
8,168,757 B2 5/2012 Kinnefrock et al.
8,354,509 B2 1/2013 Carven et al.
8,815,247 B2 8/2014 Govindappa et al.
9,441,044 B2 9/2016 Bedi et al.
9,988,456 B2 6/2018 Govindappa et al.
11,021,527 B2 6/2021 Kumar et al.
11,203,624 B2 12/2021 Kumar et al.
11,208,460 B2 12/2021 Kumar et al.
11,274,142 B2 3/2022 Gu et al.
11,274,156 B2 3/2022 Bedi et al.
2013/0287802 A1 10/2013 Govindappa et al.
2015/0079109 A1 3/2015 Li et al.
2016/0009807 A1 1/2016 Govindappa et al.
2018/0134766 A1 5/2018 Larson et al.
2019/0169621 A1 6/2019 Govindappa et al.
2019/0284257 A1 9/2019 Kumar et al.
2020/0140547 A1 5/2020 Bendi et al.
2020/0330794 A1 10/2020 Papadopoulos et al.
2020/0397823 A1 12/2020 Wyman et al.
2021/0002348 A1 1/2021 Karow et al.
2021/0107969 A1 4/2021 Bedi et al.
2022/0017601 A1 1/2022 Tian et al.
2022/0023420 A1 1/2022 Sabzevari et al.
2022/0169702 A1 6/2022 Zwaagstra et al.
2022/0204587 A1 6/2022 Lenferink et al.
2022/0289824 A1 9/2022 Liu et al.
2023/0043290 A1 2/2023 Iorio et al.
2024/0084018 A1 3/2024 Jangle et al.
2024/0343813 A1 10/2024 Salazar et al.
2024/0400683 A1 12/2024 Bedi et al.

FOREIGN PATENT DOCUMENTS

JP 2019-526613 A 9/2019
WO WO1998048024 10/1988
WO WO2008156712 12/2008
WO 2011109789 A2 9/2011

(Continued)

OTHER PUBLICATIONS

Extended European Search Report in European Application No. 21907338.4, mailed Oct. 25, 2024.

(Continued)

*Primary Examiner* — Gyan Chandra

(74) *Attorney, Agent, or Firm* — Haynes and Boone, LLP

(57) ABSTRACT

Provided herein are methods of treating cancer by administering to a subject having cancer an antibody, or functional fragment or functional variant thereof, that specifically binds programmed cell death protein 1 (PD1); and a fusion protein that comprises a targeting moiety and an immunomodulatory moiety, wherein: i) said targeting moiety specifically binds epidermal growth factor receptor (EGFR); and (ii) said immunomodulatory moiety comprises an amino acid sequence of the extracellular domain of transforming growth factor-beta receptor II (TGFβRII).

28 Claims, 9 Drawing Sheets

Specification includes a Sequence Listing.

(56) References Cited

FOREIGN PATENT DOCUMENTS

| | | | |
|---|---|---|---|
| WO | WO2012145493 | | 10/2012 |
| WO | WO2014179664 | | 11/2014 |
| WO | WO2014194302 | | 12/2014 |
| WO | WO201535606 | | 3/2015 |
| WO | WO2015085847 | | 6/2015 |
| WO | WO2015112800 | | 7/2015 |
| WO | WO2015112900 | | 7/2015 |
| WO | WO201719846 | | 2/2017 |
| WO | WO2017024465 | | 2/2017 |
| WO | WO2017025016 | | 2/2017 |
| WO | WO2017040790 | | 3/2017 |
| WO | WO2017132825 | | 8/2017 |
| WO | WO2017133540 | | 8/2017 |
| WO | 2018057303 | A1 | 3/2018 |
| WO | 2019173692 | A2 | 11/2019 |
| WO | WO2021248247 | A1 | 12/2021 |
| WO | WO2022042537 | A1 | 3/2022 |
| WO | WO2022132202 | | 6/2022 |
| WO | WO2023064278 | A2 | 4/2023 |
| WO | WO2023168363 | A1 | 9/2023 |

OTHER PUBLICATIONS

Japanese Office Action in Japanese Application No. 2023-559962 mailed Jan. 6, 2026.

Int J Radiat Oncol, Apr. 1, 2020, vol. 106, No. 5, Suppl., pp. 112 1-1122,doi: 10.1016/j.ijrobp.2019.11.376.

Anonymous: "NCT04429542 ver. 3: Jul. 6, 2020" Jun. 7, 2020 (Jun. 7, 2020), XP093213496, Retrieved from the Internet: URL:https://clinicaltrials.gov/study/NCT04 429542?term=NCT04429542&rank=1&tab=history &a=3#version-content-panel * the whole document *.

Sacco A. G. et al: "An open-label, non-randomized, multi-arm, phase II trial evaluating pembrolizumab combined with cetuximab in patients (pts) with recurrent/metastatic (R/M) head and neck squamous cell carcinoma (HNSCC): updated results of cohort 1 analysis", International Journal of Radiation: Oncology Biology Physics., vol. 106, No. 5, Apr. 1, 2020 (Apr. 1, 2020) , p. 1121, XP093213854, USA ISSN: 0360-3016, DOI: 10.1016/j.ijrobp.2019.11.375 Retrieved from the Internet: URL:https://www.redjournal.org/action/show Pdf?

Besse Benjamin et al: "Efficacy and safety of necitumumab and pembrolizumab combination therapy in patients with Stage IV non-small cell lung cancer", Lung Cancer, Elsevier, Amsterdam, NL, vol. 142, Feb. 19, 2020 (Feb. 19, 2020), pp. 63-69, XP086090178, ISSN: 0169-5002, DOI: 10.1016/J.LUNGCAN.2020.02.003 [retrieved on Feb. 19, 2020].

ClinicalTrials.gov ID NCT04429542, Viewing V4 (Sep. 14, 2020) [on-line], Sep. 17, 2020,[Search Day Dec. 19, 2025].

Onco Targets Ther,2019, vol. 12,pp. 9527-9538,doi: 10.2147/OTT.S224013.

International Search Report; PCT/US2021/010067; Search Completed Apr. 3, 2022, Report mailed Apr. 14, 2022; 4 pages.

Boreddy SR, Nair R, Pandey PK, et al. BCA101 Is a Tumor-Targeted Bifunctional Fusion Antibody That Simultaneously Inhibits EGFR and TGFβ Signaling to Durably Suppress Tumor Growth. Cancer Res. 2023;83(11):1883-1904. doi:10.1158/0008-5472.CAN-21-4425.

```
                         SEQUENCE LISTING


<160> NUMBER OF SEQ ID NOS: 67

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asn Tyr Tyr Met Tyr
1               5


<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Gly Ile Asn Pro Ser Asn Gly Gly Thr Asn Phe Asn Glu Lys Phe Lys
```

-continued

```
1               5                   10                  15

Asn


<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Arg Asp Tyr Arg Phe Asp Met Gly Phe Asp Tyr
1               5                   10


<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Arg Ala Ser Lys Gly Val Ser Thr Ser Gly Tyr Ser Tyr Leu His
1               5                   10                  15


<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Leu Ala Ser Tyr Leu Glu Ser
1               5


<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln His Ser Arg Asp Leu Pro Leu Thr
1               5


<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
```

```
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120


<210> SEQ ID NO 8
<211> LENGTH: 111
<212> TYPE: PRT
<213> ORGANISM: Artificial Sequence
<220> FEATURE:
<223> OTHER INFORMATION: Synthetic Construct

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 9
<211> LENGTH: 447
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 10
<211> LENGTH: 446
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60
```

```
Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 11
<211> LENGTH: 218
<212> TYPE: PRT
<213> ORGANISM: Artificial Sequence
<220> FEATURE:
<223> OTHER INFORMATION: Synthetic Construct

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Asn Ser Gly Met His
1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Val Ile Trp Tyr Asp Gly Ser Lys Arg Tyr Tyr Ala Asp Ser Val Lys
1               5                   10                  15

Gly

<210> SEQ ID NO 14
<211> LENGTH: 4
<212> TYPE: PRT
<213> ORGANISM: Artificial Sequence
<220> FEATURE:

<223> OTHER INFORMATION: Synthetic Construct

<400> SEQUENCE: 14

Asn Asp Asp Tyr
1

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Arg Ala Ser Gln Ser Val Ser Ser Tyr Leu Ala
1 5 10

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Asp Ala Ser Asn Arg Ala Thr
1 5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Gln Gln Ser Ser Asn Trp Pro Arg Thr
1 5

<210> SEQ ID NO 18
<211> LENGTH: 113
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Val Glu Ser Gly Gly Gly Val Val Gln Pro Gly Arg
1 5 10 15

Ser Leu Arg Leu Asp Cys Lys Ala Ser Gly Ile Thr Phe Ser Asn Ser
20 25 30

Gly Met His Trp Val Arg Gln Ala Pro Gly Lys Gly Leu Glu Trp Val
35 40 45

Ala Val Ile Trp Tyr Asp Gly Ser Lys Arg Tyr Tyr Ala Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Ala Glu Asp Thr Ala Val Tyr Tyr Cys
85 90 95

Ala Thr Asn Asp Asp Tyr Trp Gly Gln Gly Thr Leu Val Thr Val Ser
100 105 110

Ser

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Ser Asn Trp Pro Arg
85 90 95

Thr Phe Gly Gln Gly Thr Lys Val Glu Ile Lys
100 105

<210> SEQ ID NO 20
<211> LENGTH: 440
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Val Glu Ser Gly Gly Gly Val Val Gln Pro Gly Arg
1 5 10 15

Ser Leu Arg Leu Asp Cys Lys Ala Ser Gly Ile Thr Phe Ser Asn Ser
20 25 30

Gly Met His Trp Val Arg Gln Ala Pro Gly Lys Gly Leu Glu Trp Val
35 40 45

Ala Val Ile Trp Tyr Asp Gly Ser Lys Arg Tyr Tyr Ala Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Ala Glu Asp Thr Ala Val Tyr Tyr Cys
85 90 95

Ala Thr Asn Asp Asp Tyr Trp Gly Gln Gly Thr Leu Val Thr Val Ser
100 105 110

Ser Ala Ser Thr Lys Gly Pro Ser Val Phe Pro Leu Ala Pro Cys Ser
115 120 125

Arg Ser Thr Ser Glu Ser Thr Ala Ala Leu Gly Cys Leu Val Lys Asp
130 135 140

Tyr Phe Pro Glu Pro Val Thr Val Ser Trp Asn Ser Gly Ala Leu Thr
145 150 155 160

Ser Gly Val His Thr Phe Pro Ala Val Leu Gln Ser Ser Gly Leu Tyr
165 170 175

Ser Leu Ser Ser Val Val Thr Val Pro Ser Ser Ser Leu Gly Thr Lys
180 185 190

Thr Tyr Thr Cys Asn Val Asp His Lys Pro Ser Asn Thr Lys Val Asp
195 200 205

```
Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 21
<211> LENGTH: 439
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125
```

```
Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly
        435


<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Ser Asn Trp Pro Arg
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

Asn Phe Gly Met Thr
1 5

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Gly Ile Ser Gly Gly Gly Arg Asp Thr Tyr Phe Ala Asp Ser Val Lys
1 5 10 15

Gly

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Trp Gly Asn Ile Tyr Phe Asp Tyr
1 5

<210> SEQ ID NO 26
<211> LENGTH: 11
<212> TYPE: PRT

<213> ORGANISM: Artificial Sequence
<220> FEATURE:
<223> OTHER INFORMATION: Synthetic Construct

<400> SEQUENCE: 26

Arg Ala Ser Leu Ser Ile Asn Thr Phe Leu Asn
1 5 10

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Ala Ala Ser Ser Leu His Gly
1 5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gln Gln Ser Ser Asn Thr Pro Phe Thr
1 5

<210> SEQ ID NO 29
<211> LENGTH: 114
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Leu Glu Ser Gly Gly Val Leu Val Gln Pro Gly Gly
1 5 10 15

Ser Leu Arg Leu Ser Cys Ala Ala Ser Gly Phe Thr Phe Ser Asn Phe
20 25 30

Gly Met Thr Trp Val Arg Gln Ala Pro Gly Lys Gly Leu Glu Trp Val
35 40 45

Ser Gly Ile Ser Gly Gly Gly Arg Asp Thr Tyr Phe Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Lys Gly Glu Asp Thr Ala Val Tyr Tyr Cys
85 90 95

Val Lys Trp Gly Asn Ile Tyr Phe Asp Tyr Trp Gly Gln Gly Thr Leu
100 105 110

Val Thr

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Ser Leu Ser Ala Ser Val Gly

```
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105
```

```
<210> SEQ ID NO 31
<211> LENGTH: 444
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
```

```
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 32
<211> LENGTH: 443
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440


<210> SEQ ID NO 33
<211> LENGTH: 214
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
```

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Asn Tyr Gly Val His
1               5


<210> SEQ ID NO 35
<211> LENGTH: 16
<212> TYPE: PRT
<213> ORGANISM: Artificial Sequence
<220> FEATURE:
<223> OTHER INFORMATION: Synthetic Construct

<400> SEQUENCE: 35

Val Ile Trp Ser Gly Gly Asn Thr Asp Tyr Asn Thr Pro Phe Thr Ser
1               5                   10                  15


<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Ala Leu Thr Tyr Tyr Asp Tyr Glu Phe Ala Tyr
1               5                   10


<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

Arg Ala Ser Gln Ser Ile Gly Thr Asn Ile His
1               5                   10


<210> SEQ ID NO 38
<211> LENGTH: 7
<212> TYPE: PRT
```

<213> ORGANISM: Artificial Sequence
<220> FEATURE:
<223> OTHER INFORMATION: Synthetic Construct

<400> SEQUENCE: 38

Tyr Ala Ser Glu Ser Ile Ser
1 5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Gln Gln Asn Asn Asn Trp Pro Thr Thr
1 5

<210> SEQ ID NO 40
<211> LENGTH: 119
<212> TYPE: PRT
<213> ORGANISM: Artificial Sequence
<220> FEATURE:
<223> OTHER INFORMATION: Synthetic Construct

<400> SEQUENCE: 40

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ala
115

<210> SEQ ID NO 41
<211> LENGTH: 107
<212> TYPE: PRT
<213> ORGANISM: Artificial Sequence
<220> FEATURE:
<223> OTHER INFORMATION: Synthetic Construct

<400> SEQUENCE: 41

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser 65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys
100 105

<210> SEQ ID NO 42
<211> LENGTH: 449
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ala Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys

```
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 43
<211> LENGTH: 448
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 44
<211> LENGTH: 214
<212> TYPE: PRT
<213> ORGANISM: Artificial Sequence
<220> FEATURE:
<223> OTHER INFORMATION: Synthetic Construct

<400> SEQUENCE: 44

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 45
<211> LENGTH: 7
<212> TYPE: PRT
<213> ORGANISM: Artificial Sequence
<220> FEATURE:
<223> OTHER INFORMATION: Synthetic Construct

<400> SEQUENCE: 45

Ser Gly Asp Tyr Tyr Trp Thr
1               5


<210> SEQ ID NO 46
<211> LENGTH: 16
<212> TYPE: PRT
<213> ORGANISM: Artificial Sequence
<220> FEATURE:
<223> OTHER INFORMATION: Synthetic Construct

<400> SEQUENCE: 46

His Ile Tyr Tyr Ser Gly Asn Thr Asn Tyr Asn Pro Ser Leu Lys Ser
1               5                   10                  15


<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Asp Arg Val Thr Gly Ala Phe Asp Ile
1               5


<210> SEQ ID NO 48
<211> LENGTH: 11
<212> TYPE: PRT
<213> ORGANISM: Artificial Sequence
<220> FEATURE:
<223> OTHER INFORMATION: Synthetic Construct

<400> SEQUENCE: 48

Gln Ala Ser Gln Asp Ile Ser Asn Tyr Leu Asn
1               5                   10


<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Asp Ala Ser Asn Leu Glu Thr
1               5
```

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Gln His Phe Asp His Leu Pro Leu Ala
1               5

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 52
<211> LENGTH: 107
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 53

<211> LENGTH: 445
<212> TYPE: PRT
<213> ORGANISM: Artificial Sequence
<220> FEATURE:
<223> OTHER INFORMATION: Synthetic Construct

<400> SEQUENCE: 53

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

Pro Glu Asn Asn Tyr Lys Thr Thr Pro Pro Met Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 54
<211> LENGTH: 444
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser Ala Ser Thr Lys Gly Pro Ser Val Phe
115 120 125

Pro Leu Ala Pro Cys Ser Arg Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Asn Phe Gly Thr Gln Thr Tyr Thr Cys Asn Val Asp His Lys Pro
195 200 205

Ser Asn Thr Lys Val Asp Lys Thr Val Glu Arg Lys Cys Cys Val Glu
210 215 220

Cys Pro Pro Cys Pro Ala Pro Pro Val Ala Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Phe Arg Val Val Ser Val Leu
290 295 300

Thr Val Val His Gln Asp Trp Leu Asn Gly Lys Glu Tyr Lys Cys Lys
305 310 315 320

Val Ser Asn Lys Gly Leu Pro Ala Pro Ile Glu Lys Thr Ile Ser Lys
325 330 335

Thr Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Met Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly
435 440

<210> SEQ ID NO 55
<211> LENGTH: 214
<212> TYPE: PRT
<213> ORGANISM: Artificial Sequence
<220> FEATURE:
<223> OTHER INFORMATION: Synthetic Construct

<400> SEQUENCE: 55

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Phe Cys Gln His Phe Asp His Leu Pro Leu
85 90 95

Ala Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 56
<211> LENGTH: 137
<212> TYPE: PRT
<213> ORGANISM: Artificial Sequence
<220> FEATURE:
<223> OTHER INFORMATION: Synthetic Construct

<400> SEQUENCE: 56

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135
```

<210> SEQ ID NO 57
<211> LENGTH: 15
<212> TYPE: PRT
<213> ORGANISM: Artificial Sequence
<220> FEATURE:
<223> OTHER INFORMATION: Synthetic Construct

<400> SEQUENCE: 57

```
Gly Gly Gly Gly Ser Gly Gly Gly Gly Ser Gly Gly Gly Gly Ser
1               5                   10                  15
```

<210> SEQ ID NO 58
<211> LENGTH: 19
<212> TYPE: PRT
<213> ORGANISM: Artificial Sequence
<220> FEATURE:
<223> OTHER INFORMATION: Synthetic Construct

<400> SEQUENCE: 58

```
Gly Gly Gly Gly Ser Gly Gly Gly Gly Ser Gly Gly Gly Gly Ser Gly
1               5                   10                  15

Gly Gly Ser
```

<210> SEQ ID NO 59
<211> LENGTH: 23
<212> TYPE: PRT
<213> ORGANISM: Artificial Sequence
<220> FEATURE:
<223> OTHER INFORMATION: Synthetic Construct

<400> SEQUENCE: 59

```
Gly Gly Gly Gly Ser Gly Gly Gly Gly Ser Gly Gly Gly Gly Ser Gly
1               5                   10                  15
```

Gly Gly Ser Gly Gly Gly Ser
20

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Gly Gly Gly Gly Ser Gly Gly Gly Gly Ser
1 5 10

<210> SEQ ID NO 61
<211> LENGTH: 5
<212> TYPE: PRT
<213> ORGANISM: Artificial Sequence
<220> FEATURE:
<223> OTHER INFORMATION: Synthetic Construct

<400> SEQUENCE: 61

Gly Gly Gly Gly Ser
1 5

<210> SEQ ID NO 62
<211> LENGTH: 366
<212> TYPE: PRT
<213> ORGANISM: Artificial Sequence
<220> FEATURE:
<223> OTHER INFORMATION: Synthetic Construct

<400> SEQUENCE: 62

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Gly Gly Gly Gly Ser

```
    210                 215                 220

Gly Gly Gly Gly Ser Thr Ile Pro Pro His Val Gln Lys Ser Val Asn
225                 230                 235                 240

Asn Asp Met Ile Val Thr Asp Asn Asn Gly Ala Val Lys Phe Pro Gln
                245                 250                 255

Leu Cys Lys Phe Cys Asp Val Arg Phe Ser Thr Cys Asp Asn Gln Lys
            260                 265                 270

Ser Cys Met Ser Asn Cys Ser Ile Thr Ser Ile Cys Glu Lys Pro Gln
        275                 280                 285

Glu Val Cys Val Ala Val Trp Arg Lys Asn Asp Glu Asn Ile Thr Leu
    290                 295                 300

Glu Thr Val Cys His Asp Pro Lys Leu Pro Tyr His Asp Phe Ile Leu
305                 310                 315                 320

Glu Asp Ala Ala Ser Pro Lys Cys Ile Met Lys Glu Lys Lys Lys Pro
                325                 330                 335

Gly Glu Thr Phe Phe Met Cys Ser Cys Ser Ser Asp Glu Cys Asn Asp
            340                 345                 350

Asn Ile Ile Phe Ser Glu Glu Tyr Asn Thr Ser Asn Pro Asp
        355                 360                 365


<210> SEQ ID NO 63
<211> LENGTH: 600
<212> TYPE: PRT
<213> ORGANISM: Artificial Sequence
<220> FEATURE:
<223> OTHER INFORMATION: Synthetic Construct

<400> SEQUENCE: 63

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
```

```
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Gly Ser Gly Gly Gly Gly Ser Thr
    450                 455                 460

Ile Pro Pro His Val Gln Lys Ser Val Asn Asn Asp Met Ile Val Thr
465                 470                 475                 480

Asp Asn Asn Gly Ala Val Lys Phe Pro Gln Leu Cys Lys Phe Cys Asp
                485                 490                 495

Val Arg Phe Ser Thr Cys Asp Asn Gln Lys Ser Cys Met Ser Asn Cys
            500                 505                 510

Ser Ile Thr Ser Ile Cys Glu Lys Pro Gln Glu Val Cys Val Ala Val
        515                 520                 525

Trp Arg Lys Asn Asp Glu Asn Ile Thr Leu Glu Thr Val Cys His Asp
    530                 535                 540

Pro Lys Leu Pro Tyr His Asp Phe Ile Leu Glu Asp Ala Ala Ser Pro
545                 550                 555                 560

Lys Cys Ile Met Lys Glu Lys Lys Lys Pro Gly Glu Thr Phe Phe Met
                565                 570                 575

Cys Ser Cys Ser Ser Asp Glu Cys Asn Asp Asn Ile Ile Phe Ser Glu
            580                 585                 590

Glu Tyr Asn Thr Ser Asn Pro Asp
        595                 600
```

<210> SEQ ID NO 64
<211> LENGTH: 601
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ala Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys Gly Gly Gly Gly Ser Gly Gly Gly Gly Ser Gly Gly Gly Gly Ser
450 455 460

Thr Ile Pro Pro His Val Gln Lys Ser Val Asn Asn Asp Met Ile Val
465 470 475 480

Thr Asp Asn Asn Gly Ala Val Lys Phe Pro Gln Leu Cys Lys Phe Cys
485 490 495

Asp Val Arg Phe Ser Thr Cys Asp Asn Gln Lys Ser Cys Met Ser Asn
500 505 510

Cys Ser Ile Thr Ser Ile Cys Glu Lys Pro Gln Glu Val Cys Val Ala
515 520 525

Val Trp Arg Lys Asn Asp Glu Asn Ile Thr Leu Glu Thr Val Cys His
530 535 540

Asp Pro Lys Leu Pro Tyr His Asp Phe Ile Leu Glu Asp Ala Ala Ser
545 550 555 560

Pro Lys Cys Ile Met Lys Glu Lys Lys Lys Pro Gly Glu Thr Phe Phe
565 570 575

Met Cys Ser Cys Ser Ser Asp Glu Cys Asn Asp Asn Ile Ile Phe Ser
580 585 590

Glu Glu Tyr Asn Thr Ser Asn Pro Asp
595 600

<210> SEQ ID NO 65
<211> LENGTH: 366
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Phe Cys Gln His Phe Asp His Leu Pro Leu
85 90 95

Ala Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Gly Gly Gly Gly Ser
210 215 220

Gly Gly Gly Gly Ser Thr Ile Pro Pro His Val Gln Lys Ser Val Asn
225 230 235 240

Asn Asp Met Ile Val Thr Asp Asn Asn Gly Ala Val Lys Phe Pro Gln
245 250 255

Leu Cys Lys Phe Cys Asp Val Arg Phe Ser Thr Cys Asp Asn Gln Lys
260 265 270

Ser Cys Met Ser Asn Cys Ser Ile Thr Ser Ile Cys Glu Lys Pro Gln
275 280 285

Glu Val Cys Val Ala Val Trp Arg Lys Asn Asp Glu Asn Ile Thr Leu
290 295 300

Glu Thr Val Cys His Asp Pro Lys Leu Pro Tyr His Asp Phe Ile Leu
305 310 315 320

Glu Asp Ala Ala Ser Pro Lys Cys Ile Met Lys Glu Lys Lys Lys Pro
325 330 335

Gly Glu Thr Phe Phe Met Cys Ser Cys Ser Ser Asp Glu Cys Asn Asp
340 345 350

Asn Ile Ile Phe Ser Glu Glu Tyr Asn Thr Ser Asn Pro Asp
355 360 365

<210> SEQ ID NO 66
<211> LENGTH: 597
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser Ala Ser Thr Lys Gly Pro Ser Val Phe
115 120 125

Pro Leu Ala Pro Cys Ser Arg Ser Thr Ser Glu Ser Thr Ala Ala Leu
130 135 140

Gly Cys Leu Val Lys Asp Tyr Phe Pro Glu Pro Val Thr Val Ser Trp
145 150 155 160

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Gly Ser Gly Gly Gly Gly Ser Gly Gly Gly Gly Ser Thr Ile Pro Pro
    450                 455                 460

His Val Gln Lys Ser Val Asn Asn Asp Met Ile Val Thr Asp Asn Asn
465                 470                 475                 480

Gly Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
        515                 520                 525

Asn Asp Glu Asn Ile Thr Leu Glu Thr Val Cys His Asp Pro Lys Leu
    530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
                565                 570                 575
```

```
Ser Ser Asp Glu Cys Asn Asp Asn Ile Ile Phe Ser Glu Glu Tyr Asn
            580                 585                 590

Thr Ser Asn Pro Asp
        595


<210> SEQ ID NO 67
<211> LENGTH: 597
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335
```

-continued

```
Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Gly Ser Gly Gly Gly Gly Ser Gly Gly Gly Gly Ser Thr Ile Pro Pro
    450                 455                 460

His Val Gln Lys Ser Val Asn Asn Asp Met Ile Val Thr Asp Asn Asn
465                 470                 475                 480

Gly Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
        515                 520                 525

Asn Asp Glu Asn Ile Thr Leu Glu Thr Val Cys His Asp Pro Lys Leu
    530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
                565                 570                 575

Ser Ser Asp Glu Cys Asn Asp Asn Ile Ile Phe Ser Glu Glu Tyr Asn
            580                 585                 590

Thr Ser Asn Pro Asp
        595
```

COMBINATION THERAPY FOR THE TREATMENT OF CANCER

CROSS-REFERENCE TO RELATED APPLICATIONS

This application is a U.S. national phase application and claims the benefit of priority under 35U.S.C. § 371 of International Application No. PCT/US2021/010067, filed on Dec. 15, 2021, which claims the priority to and the benefit of Indian Provisional Application No. IN202011054571, filed on Dec. 15, 2020, the entire disclosure of which is incorporated herein by reference.

BACKGROUND

Immune checkpoint inhibitors are a class of cancer therapeutics that function to reverse T cell inhibition and tumor immunoevasion. Immune checkpoint inhibitors include, antibodies that specifically bind to and inhibit immune checkpoint proteins such as programmed cell death protein 1 (PD1) or its ligand programmed cell death-ligand 1 (PDL1) and cytotoxic T lymphocyte associated antigen 4 (CTLA4). However, antibody immune checkpoint inhibitors remain associated with several clinical problems in terms of efficacy and patient-to-patient variability. Combination therapies targeting multiple non-redundant pathways regulating immune responses may enhance immune checkpoint inhibitor efficacy. However, not all combinations provide a synergistic effect over the monotherapy components. Therefore, there is a need for combination therapies with an acceptable safety profile and high efficacy that enhance antitumor immune responses compared to monotherapy and other immunotherapy combinations.

SUMMARY

Provided herein are methods of treating cancer in a subject that comprise administering an agent that specifically binds PD1 in combination with a fusion protein that specifically binds EGFR and binds TGFβ (e.g., fusion proteins described herein). The combination treatments disclosed herein can be particularly useful in the treatment of EGFR driven cancers.

Accordingly, in one aspect the instant disclosure provides a method of treating cancer in a human subject in need thereof, said method comprising: administering to said subject an antibody, or functional fragment or functional variant thereof, that specifically binds programmed cell death protein 1 (PD1); and administering to said subject a fusion protein that comprises a targeting moiety and an immunomodulatory moiety, wherein: i) said targeting moiety specifically binds epidermal growth factor receptor (EGFR); and (ii) said immunomodulatory moiety comprises an amino acid sequence of the extracellular domain of transforming growth factor-beta receptor II (TGFβRII).

In some embodiments, said antibody, or functional fragment or functional variant thereof, that specifically binds PD1 is a full-length antibody, a single chain variable fragment (scFv), a scFv2, a scFv-Fc, a Fab, a Fab', a F(ab')2, or a F(v).

In some embodiments, said antibody, or functional fragment or functional variant thereof, that specifically binds PD1 inhibits binding of PD1 to PDL1. In some embodiments, said antibody, or functional fragment or functional variant thereof, that specifically binds PD1 inhibits signaling of PD1.

In some embodiments, said antibody, or functional fragment or functional variant thereof, that specifically binds PD1 comprises a VH that comprises VH CDR1, VH CDR2, and VH CDR3, wherein VH CDR1 comprises an amino acid sequence at least 95%, 96%, 97%, 98%, 99%, or 100% identical to the amino acid sequence of SEQ ID NO: 1; VH CDR2 comprises an amino acid sequence at least 95%, 96%, 97%, 98%, 99%, or 100% identical to the amino acid sequence of SEQ ID NO: 2; and VH CDR3 comprises an amino acid sequence at least 95%, 96%, 97%, 98%, 99%, or 100% identical to the amino acid sequence of SEQ ID NO: 3.

In some embodiments, said antibody, or functional fragment or functional variant thereof, that specifically binds PD1 comprises a VL that comprises a VL CDR1, a VL CDR2, and a VL CDR3, wherein VL CDR1 comprises an amino acid sequence at least the amino acid sequence of 95%, 96%, 97%, 98%, 99%, or 100% identical to SEQ ID NO: 4; VL CDR2 comprises an amino acid sequence at least the amino acid sequence of 95%, 96%, 97%, 98%, 99%, or 100% identical to SEQ ID NO: 5; and VL CDR3 comprises an amino acid sequence at least 95%, 96%, 97%, 98%, 99%, or 100% identical to the amino acid sequence of SEQ ID NO: 6.

In some embodiments, said antibody, or functional fragment or functional variant thereof, that specifically binds PD1 comprises a VH that comprises an amino acid sequence at least 95%, 96%, 97%, 98%, 99%, or 100% identical to the amino acid sequence of SEQ ID NO: 7.

In some embodiments, said antibody, or functional fragment or functional variant thereof, that specifically binds PD1 comprises a VL that comprises an amino acid sequence at least 95%, 96%, 97%, 98%, 99%, or 100% identical to the amino acid sequence of SEQ ID NO: 8.

In some embodiments, said antibody, or functional fragment or functional variant thereof, that specifically binds PD1 comprises a heavy chain region that comprises an amino acid sequence at least 95%, 96%, 97%, 98%, 99%, or 100% identical to the amino acid sequence of SEQ ID NO: 9.

In some embodiments, said antibody, or functional fragment or functional variant thereof, that specifically binds PD1 comprises a heavy chain region that comprises an amino acid sequence at least 95%, 96%, 97%, 98%, 99%, or 100% identical to the amino acid sequence of SEQ ID NO: 10.

In some embodiments, said antibody, or functional fragment or functional variant thereof, that specifically binds PD1 comprises a light chain region that comprises an amino acid sequence at least 95%, 96%, 97%, 98%, 99%, or 100% identical to the amino acid sequence of SEQ ID NO: 11.

In some embodiments, said antibody, or functional fragment or functional variant thereof, that specifically binds PD1 comprises pembrolizumab, nivolumab, cemiplimab, spartalizumab, camrelizumab, tislelizumab, dostarlimab, cetrelimab, pidilizumab, MEDI0680, SSI-361, AMP-224, PDR001, PF-06801591, BGB-A317, TSR-042, AGEN-2034, A-0001, BGB-108, BI-754091, CBT-501, ENUM-003, ENUM-388D4, IBI-308, JNJ-63723283, JS-001, JTX-4014, JY-034, CLA-134, STIA-1110, 244C8, and 388D4, or a functional fragment or functional variant of any of the foregoing.

In some embodiments, said antibody, or functional fragment or functional variant thereof, that specifically binds PD1 comprises pembrolizumab, or a functional fragment or functional variant of any of the foregoing.

In some embodiments, said targeting moiety that specifically binds EGFR comprises an antibody or functional fragment or functional variant thereof, that specifically binds EGFR. In some embodiments, said antibody, or functional fragment or functional variant thereof, that specifically binds EGFR is a full-length antibody, a single chain variable fragment (scFv), a scFv2, a scFv-Fc, a Fab, a Fab', a F(ab')2, or a F(v).

In some embodiments, said antibody, or functional fragment or functional variant thereof, that specifically binds EGFR comprises a VH that comprises VH CDR1, VH CDR2, and VH CDR3, wherein VH CDR1 comprises an amino acid sequence at least 95%, 96%, 97%, 98%, 99%, or 100% identical to the amino acid sequence of SEQ ID NO: 34; VH CDR2 comprises an amino acid sequence at least 95%, 96%, 97%, 98%, 99%, or 100% identical to the amino acid sequence of SEQ ID NO: 35; and VH CDR3 comprises an amino acid sequence at least 95%, 96%, 97%, 98%, 99%, or 100% identical to the amino acid sequence of SEQ ID NO: 36.

In some embodiments, said antibody, or functional fragment or functional variant thereof, that specifically binds EGFR comprises a VL that comprises a VL CDR1, a VL CDR2, and a VL CDR3, wherein VL CDR1 comprises an amino acid sequence at least 95%, 96%, 97%, 98%, 99%, or 100% identical to the amino acid sequence of SEQ ID NO: 37; VL CDR2 comprises an amino acid sequence at least 95%, 96%, 97%, 98%, 99%, or 100% identical to the amino acid sequence of SEQ ID NO: 38; and VL CDR3 comprises an amino acid sequence at least 95%, 96%, 97%, 98%, 99%, or 100% identical to the amino acid sequence of SEQ ID NO: 39.

In some embodiments, said antibody, or functional fragment or functional variant thereof, that specifically binds EGFR comprises a VH that comprises an amino acid sequence at least 95%, 96%, 97%, 98%, 99%, or 100% identical to the amino acid sequence of SEQ ID NO: 40.

In some embodiments, said antibody, or functional fragment or functional variant thereof, that specifically binds EGFR comprises a VL that comprises an amino acid sequence at least 95%, 96%, 97%, 98%, 99%, or 100% identical to the amino acid sequence of SEQ ID NO: 41.

In some embodiments, said antibody, or functional fragment or functional variant thereof, that specifically binds EGFR comprises a heavy chain that comprises an amino acid sequence at least 95%, 96%, 97%, 98%, 99%, or 100% identical to the amino acid sequence of SEQ ID NO: 42.

In some embodiments, said antibody, or functional fragment or functional variant thereof, that specifically binds EGFR consists of a heavy chain that comprises an amino acid sequence at least 95%, 96%, 97%, 98%, 99%, or 100% identical to the amino acid sequence of SEQ ID NO: 43.

In some embodiments, said antibody, or functional fragment or functional variant thereof, that specifically binds EGFR comprises a heavy chain that consists of an amino acid sequence at least 95%, 96%, 97%, 98%, 99%, or 100% identical to the amino acid sequence of SEQ ID NO: 42.

In some embodiments, said antibody, or functional fragment or functional variant thereof, that specifically binds EGFR consists of a heavy chain that consists of an amino acid sequence at least 95%, 96%, 97%, 98%, 99%, or 100% identical to the amino acid sequence of SEQ ID NO: 43.

In some embodiments, said antibody, or functional fragment or functional variant thereof, that specifically binds EGFR comprises a light chain that comprises an amino acid sequence at least 95%, 96%, 97%, 98%, 99%, or 100% identical to the amino acid sequence of SEQ ID NO: 44.

In some embodiments, said antibody, or functional fragment or functional variant thereof, that specifically binds EGFR consists of a light chain that consists of an amino acid sequence at least 95%, 96%, 97%, 98%, 99%, or 100% identical to the amino acid sequence of SEQ ID NO: 44.

In some embodiments, said antibody, or functional fragment or functional variant thereof, that specifically binds EGFR comprises cetuximab or panitumumab, or a functional fragment or functional variant of any of the foregoing.

In some embodiments, said immunomodulatory moiety comprises an amino acid sequence at least 95%, 96%, 97%, 98%, 99%, or 100% identical to SEQ ID NO: 56. In some embodiments, said immunomodulatory moiety consists of an amino acid sequence at least 95%, 96%, 97%, 98%, 99%, or 100% identical to the amino acid sequence of SEQ ID NO: 56.

In some embodiments, said immunomodulatory moiety is indirectly fused to said targeting moiety. In some embodiments, said immunomodulatory moiety is indirectly fused to said targeting moiety via a peptide linker. In some embodiments, said immunomodulatory moiety is indirectly fused to said targeting moiety via a peptide linker of sufficient length such that said immunomodulatory moiety and said targeting moiety can simultaneously bind the respective targets.

In some embodiments, said linker comprises the amino acid sequence of SEQ ID NO: 57, 58, 59, 60, or 61. In some embodiments, said linker comprises the amino acid sequence of SEQ ID NO: 57. In some embodiments, said linker consists of the amino acid sequence of SEQ ID NO: 57.

In some embodiments, said immunomodulatory moiety is fused to the C terminus of said targeting moiety. In some embodiments, said immunomodulatory moiety is fused to the N terminus of said targeting moiety.

In some embodiments, said targeting moiety is an antibody that comprises a light chain and a heavy chain, and wherein said immunomodulatory moiety is fused to the C terminus of said heavy chain of said targeting moiety. In some embodiments, said targeting moiety is an antibody that comprises a light chain and a heavy chain, and wherein said immunomodulatory moiety is fused to the C terminus of said light chain of said targeting moiety.

In some embodiments, said targeting moiety is an antibody specifically binds epidermal growth factor receptor (EGFR) that comprises a heavy chain that comprises an amino acid sequence at least 95%, 96%, 97%, 98%, 99%, or 100% identical to the amino acid sequence of SEQ ID NO: 43, and a light chain that comprises an amino acid sequence at least 95%, 96%, 97%, 98%, 99%, or 100% identical to the amino acid sequence of SEQ ID NO: 44, and wherein said immunomodulatory moiety comprises an amino acid sequence at least 95%, 96%, 97%, 98%, 99%, or 100% identical to the amino acid sequence of SEQ ID NO: 56, and wherein the N terminus of said immunomodulatory moiety is fused indirectly through a linker to the C terminus of said heavy chain or said light chain, and wherein said linker comprises an amino acid sequence at least 95%, 96%, 97%, 98%, 99%, or 100% identical to the amino acid sequence of SEQ ID NO: 57.

In some embodiments, said targeting moiety is an antibody specifically binds epidermal growth factor receptor (EGFR) that comprises a heavy chain that comprises an amino acid sequence at least 95%, 96%, 97%, 98%, 99%, or 100% identical to the amino acid sequence of SEQ ID NO: 43, and a light chain that comprises an amino acid sequence at least 95%, 96%, 97%, 98%, 99%, or 100% identical to the amino acid sequence of SEQ ID NO: 44, and wherein said immunomodulatory moiety comprises an amino acid sequence at least 95%, 96%, 97%, 98%, 99%, or 100% identical to the amino acid sequence of SEQ ID NO: 56, and wherein the N terminus of said immunomodulatory moiety is fused indirectly through a linker to the C terminus of said light chain, and wherein said linker comprises an amino acid sequence at least 95%, 96%, 97%, 98%, 99%, or 100% identical to the amino acid sequence of SEQ ID NO: 57.

In some embodiments, said targeting moiety comprises an antibody that comprises a heavy chain comprising an amino acid sequence at least 95%, 96%, 97%, 98%, 99%, or 100% identical to the amino acid sequence of SEQ ID NO: 43; and a light chain comprising an amino acid sequence at least 95%, 96%, 97%, 98%, 99%, or 100% identical to the amino acid sequence of SEQ ID NO: 62.

In some embodiments, said cancer is a solid tumor. In some embodiments, said cancer is selected from the group consisting of breast cancer, anal cancer, pancreatic cancer, thyroid cancer, liver cancer, ovarian cancer, lung cancer, skin cancer, brain cancer, spinal cord cancer, head cancer, neck cancer, and head and neck cancer.

In some embodiments, said cancer is head and neck cancer. In some embodiments, said cancer is head and neck squamous cell carcinoma (HNSCC). In some embodiments, said cancer is recurrent HNSCC. In some embodiments, said cancer is metastatic HNSCC. In some embodiments, said cancer is recurrent and metastatic HNSCC.

In some embodiments, said cancer is squamous cell carcinoma of anal canal (SCCAC). In some embodiments, said cancer is recurrent SCCAC. In some embodiments, said cancer is metastatic SCCAC. In some embodiments, said cancer is recurrent and metastatic SCCAC.

In some embodiments, said antibody, or functional fragment or functional variant thereof, that specifically binds PD1 is administered to said human subject at a dose from about 100 mg to 500 mg, 100 mg to 400 mg, 100 mg to 300 mg, or 100 mg to 200 mg.

In some embodiments, said antibody, or functional fragment or functional variant thereof, that specifically binds PD1 is administered to said human subject at a dose of about 100 mg, 200 mg, 300 mg, 400 mg, or 500 mg. In some embodiments, said antibody, or functional fragment or functional variant thereof, that specifically binds PD1 is administered to said human subject at a dose of about 200 mg. In some embodiments, said antibody, or functional fragment or functional variant thereof, that specifically binds PD1 is administered to said human subject at a dose of about 300 mg.

In some embodiments, said antibody, or functional fragment or functional variant thereof, that specifically binds PD1 is administered to said human subject every 1, 2, 3, or 4 weeks. In some embodiments, said antibody, or functional fragment or functional variant thereof, that specifically binds PD1 is administered to said human subject every 3 weeks.

In some embodiments, said fusion protein is administered to said human subject at a dose from about 50 mg to 2000 mg, 100 mg to 2000 mg, 150 mg to 2000 mg, 200 mg to 2000 mg, 300 mg to 2000 mg, 400 mg to 2000 mg, 500 mg to 2000 mg, 600 mg to 2000 mg, 700 mg to 2000 mg, 800 mg to 2000 mg, 9000 mg to 2000 mg, 1000 mg to 2000 mg, 1500 mg to 2000 mg, 50 mg to 100 mg, 50 mg to 500 mg, 50 mg to 400 mg, 50 mg to 300 mg, 50 mg to 200 mg, 50 mg to 100 mg, 100 mg to 500 mg, 100 mg to 400 mg, 100 mg to 300 mg, or 100 mg to 200 mg. In some embodiments, said fusion protein is administered to said human subject at a dose from about 200 mg to 2000 mg. In some embodiments, said fusion protein is administered to said human subject at a dose of about 50 mg, 60 mg, 64 mg, 100 mg, 150 mg, 200 mg, 240 mg, 250 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900, or 2000 mg. In some embodiments, said fusion protein is administered to said human subject at a dose of about 64 mg, 240 mg, 800 mg, or 1600 mg.

In some embodiments, said fusion protein is administered to said human subject every 1, 2, 3, or 4 weeks. In some embodiments, said fusion protein is administered to said human subject every week. In some embodiments, said fusion protein is administered to said human subject 3 weeks.

In some embodiments, said fusion protein is co-administered, administered prior to, or administered after, said antibody, or functional fragment or functional variant thereof, that specifically binds PD1.

BRIEF DESCRIPTION OF THE FIGURES

FIG. 2A is a line graph that shows the individual tumor growth in the isotype control group over 21 days. FIG. 2B is a line graph that shows the individual tumor growth in the cetuximab treatment group over 21 days. FIG. 2C is a line graph that shows the individual tumor growth in the BCA101 treatment group over 21 days. FIG. 2D is a line graph that shows the individual tumor growth in the anti-PD1 (pembrolizumab) treatment group over 21 days. FIG. 2E is a line graph that shows the individual tumor growth in the BCA101+anti-PD1 (pembrolizumab) treatment group over 21 days.

INCORPORATION BY REFERENCE

Figure 1:
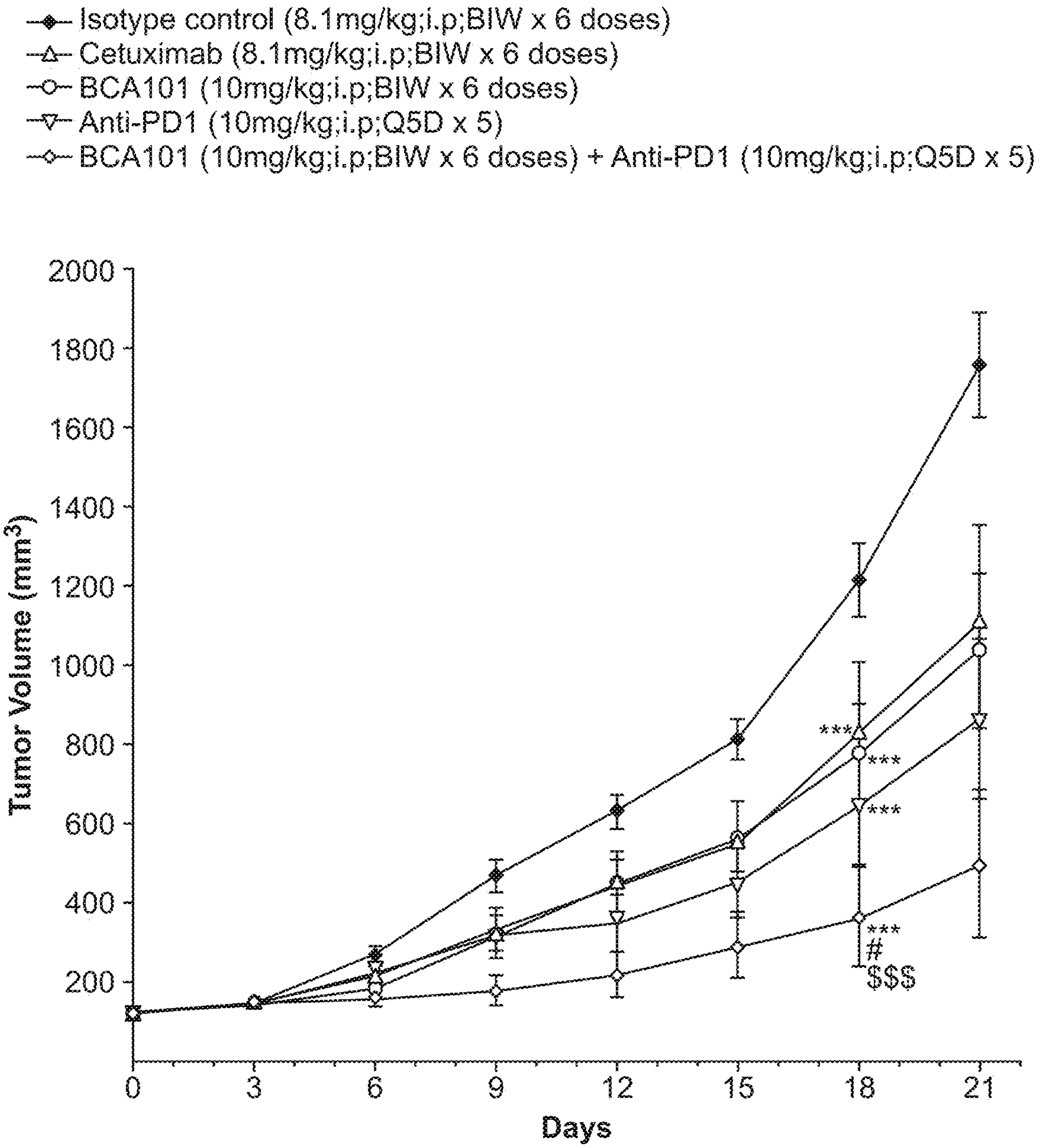
FIG. 1 is a line graph that shows the effect of cetuximab, BCA101(Fusion mAb anti EGFR+TGFβRII ECD), anti-PD1 (pembrolizumab), and BCA101+anti-PD1 (pembrolizumab) in huNOG-EXL mice bearing PC-3 xenograft tumor on tumor volume over the course of 21 days. Values are expressed as Mean±SEM of 8-10 animals in each group. Statistical analysis carried out by Two-way ANOVA followed by Bonferroni post tests using Graph Pad Prism (Version 8.3.0). *** significant ($p<0.001$) difference when respective treatment groups were compared with isotype control group on day 18. $^{\$\$\$}$significant ($p<0.001$) and $^{\#}$significant ($p<0.05$) difference when combination treatment group was compared with BCA101 and pembrolizumab respectively on day 18.
Figure 2A:
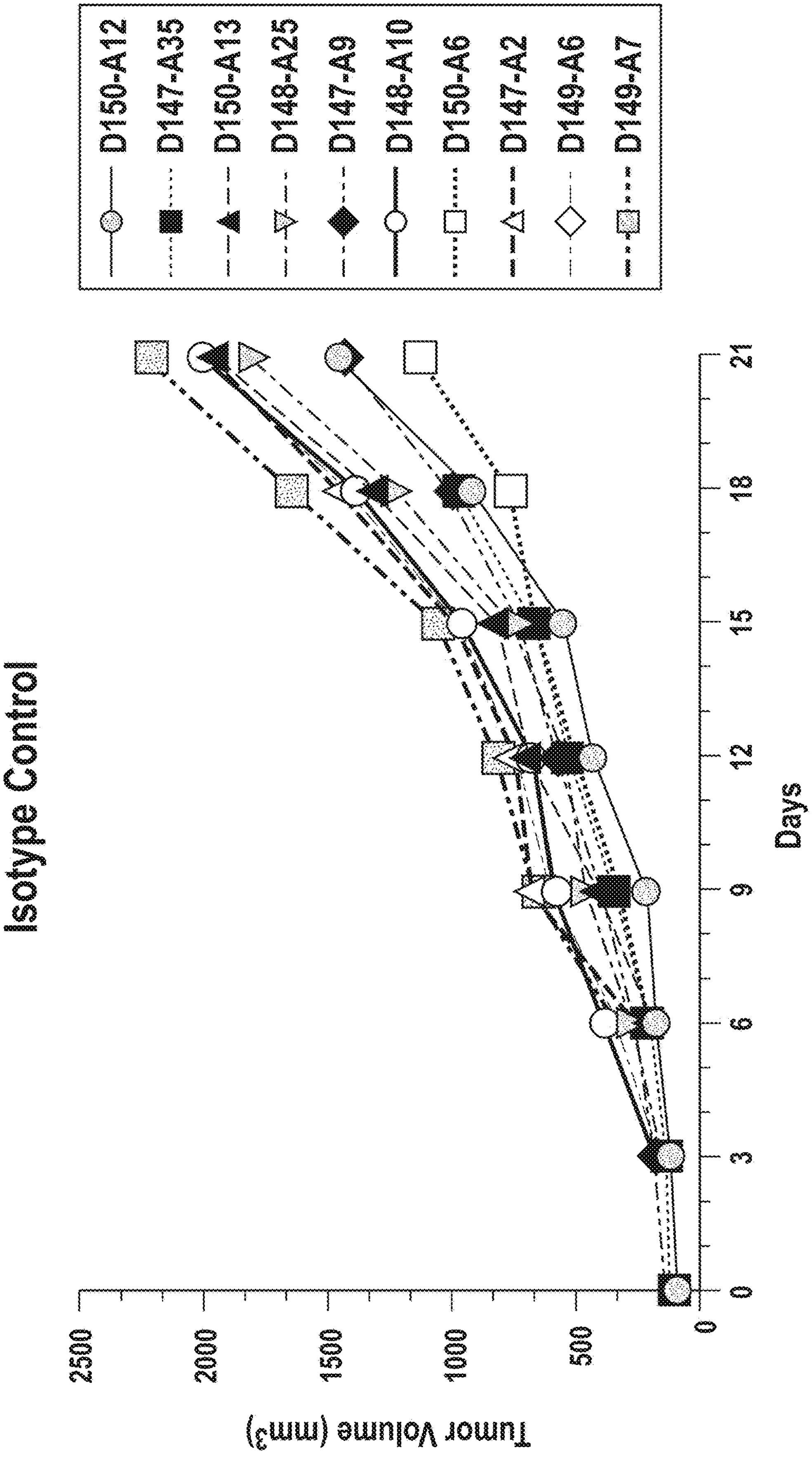
FIGS. 2A-2E are line graphs that show the individual tumor growth curve of huNOG-EXL mice PC-3 tumor xenograft over the course of 21 days.
Figure 2B:
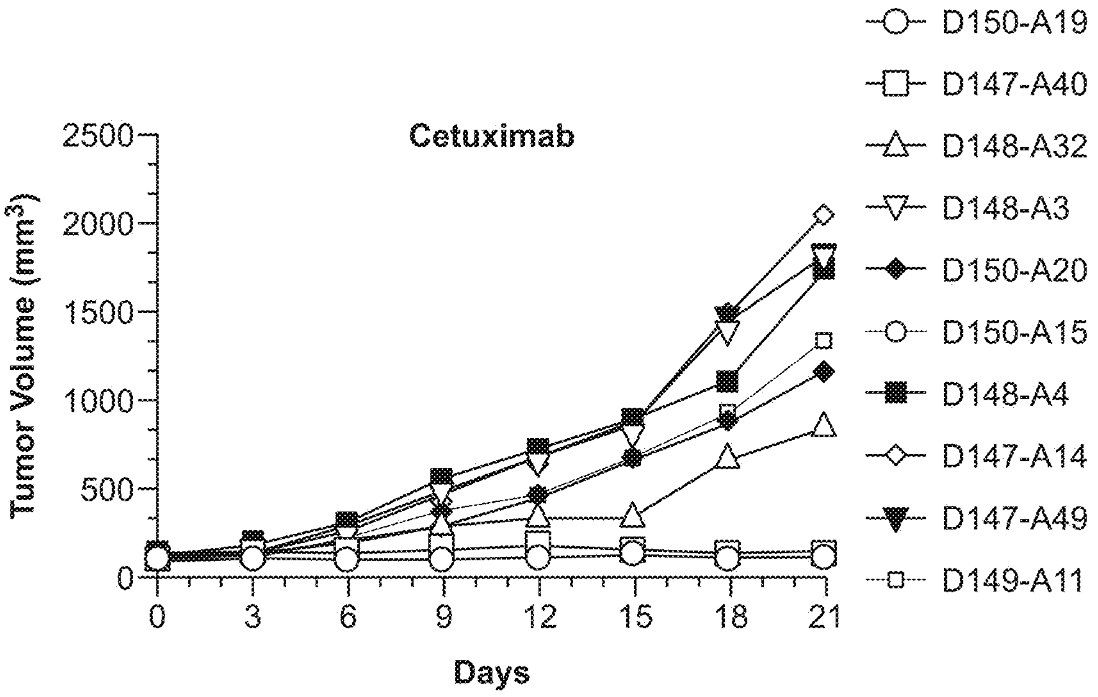
Figure 2C:
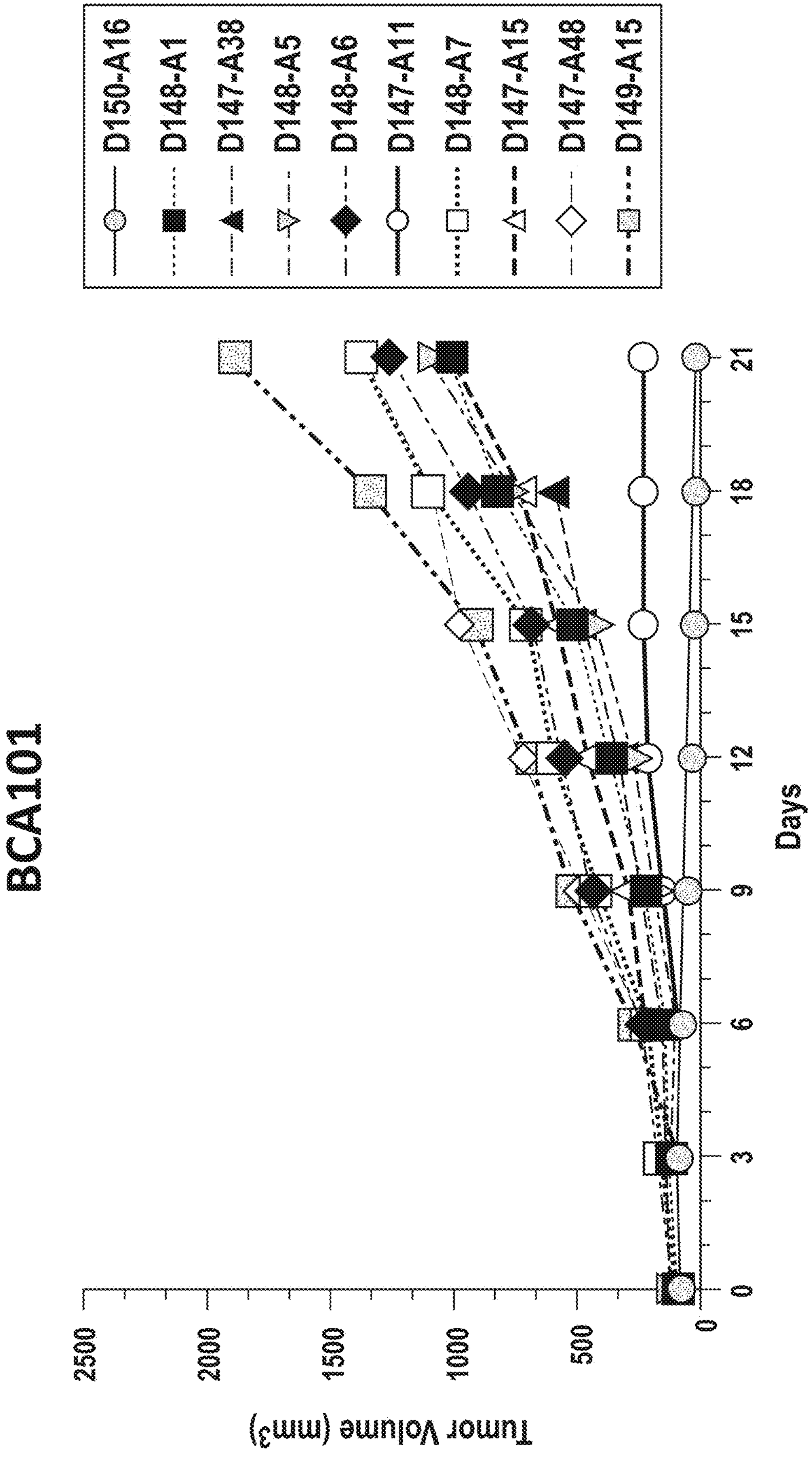
Figure 2D:
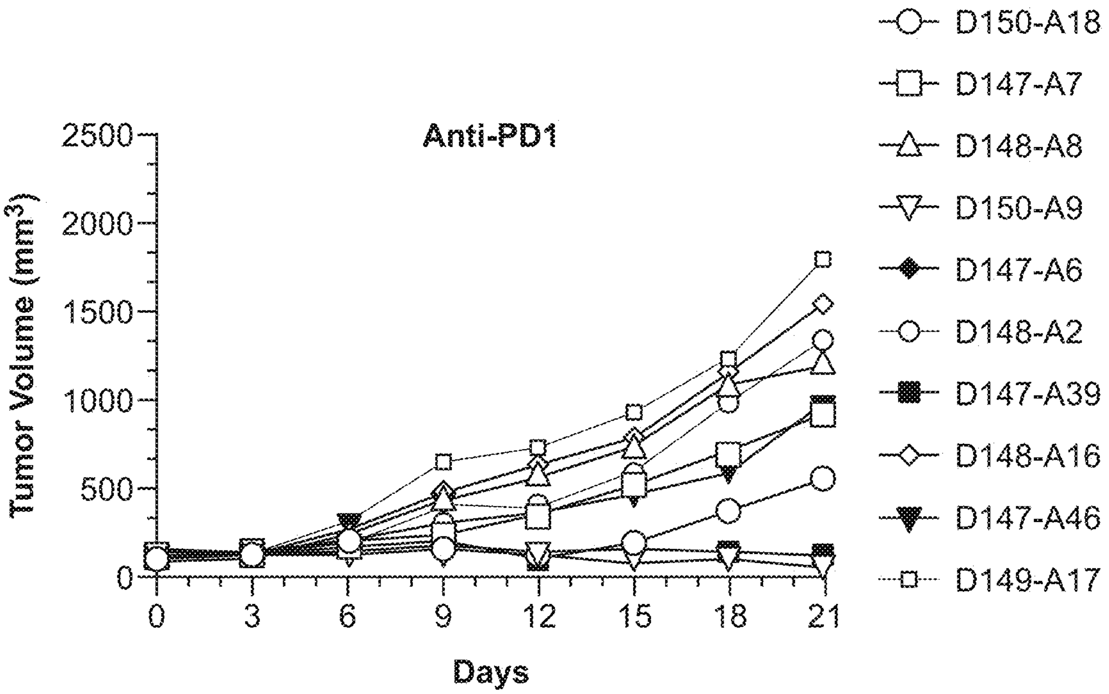
Figure 2E:
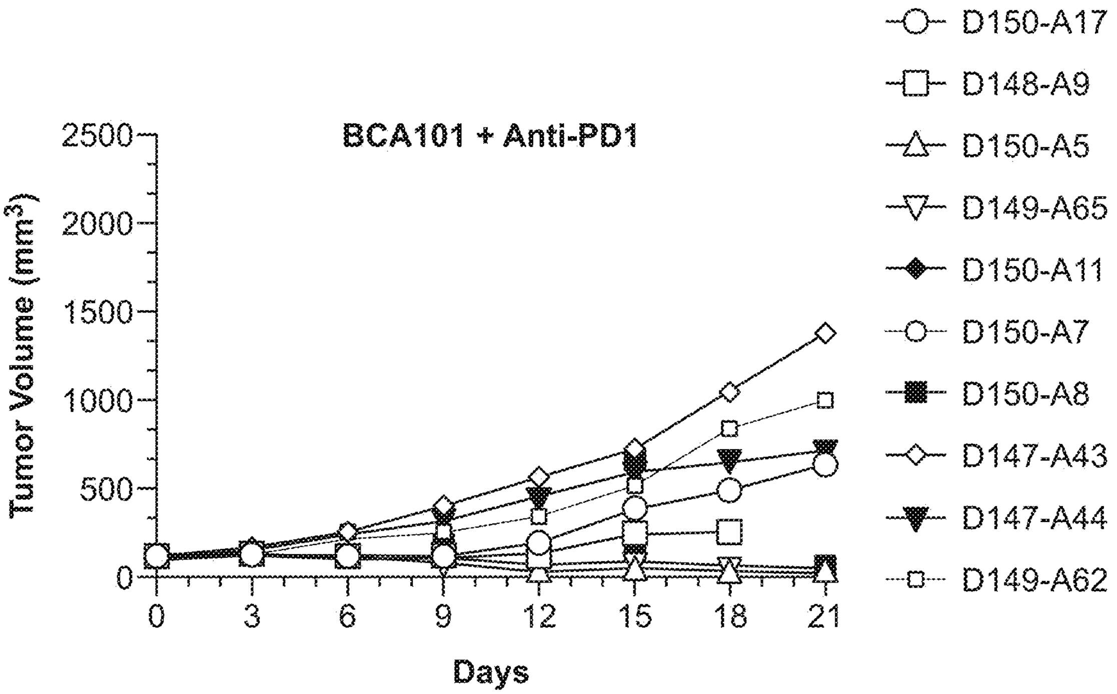

All publications, patents, and patent applications mentioned in this specification are herein incorporated by reference to the same extent as if each individual publication, patent, or patent application was specifically and individually indicated to be incorporated by reference.

DETAILED DESCRIPTION

Overview

The present disclosure provides, inter alia, new combination therapies comprising an agent that specifically binds to and inhibits the function of PD1 and an EGFR targeted immunomodulatory fusion protein that binds TGFβ. The combination therapies described herein provide a synergistic effect and improved efficacy over each of the monotherapies. In some embodiments, the EGFR fusion protein comprises a targeting moiety that specifically binds EGFR and an immunomodulatory moiety that comprises an amino acid sequence of the extracellular domain of transforming growth factor-beta receptor II (TGFβRII). The combination treatments disclosed herein can be particularly useful in the treatment of EGFR driven cancers, such as head and neck cancers and anal cancer.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise.

It must be noted that, as used in the specification and the appended claims, the singular forms "a," "an," and "the" include plural referents unless the context clearly dictates otherwise. Furthermore, use of the term "including" as well as other forms, such as "include," "includes," and "included," is not limiting.

It is understood that wherever aspects are described herein with the language "comprising," otherwise analogous aspects described in terms of "consisting of" and/or "consisting essentially of" are also provided.

The section headings used herein are for organizational purposes only and are not to be construed as limiting the subject matter described.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

As described herein, any concentration range, percentage range, ratio range or integer range is to be understood to include the value of any integer within the recited range and, when appropriate, fractions thereof (such as one tenth and one hundredth of an integer), unless otherwise indicated.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "programmed cell death protein 1" and "PD1" are used interchangeably herein and refer to an immunoinhibitory receptor belonging to the CD28 family. PD1 is expressed predominantly on previously activated T cells in vivo, and binds to two ligands, PDL1 and PDL2. The term PD1 as used herein includes human PD1 (hPD1), variants, isoforms, and species homologs of hPD1, and analogs having at least one common epitope with hPD1. The complete hPD-1 sequence can be found under GenBank Accession No. U64863.

The terms "epidermal growth factor receptor" and "EGFR" are used interchangeably herein and refer to a transmembrane protein that is a receptor for members of the epidermal growth factor family (EGF family) of extracellular protein ligands. The term EGFR as used herein includes human EGFR (hEGFR), variants, isoforms, and species homologs of hEGFR, and analogs having at least one common epitope with EGFR. The complete hEGFR sequence can be found under GenBank Gene ID: 1956.

The terms "subject" and "patient" are used interchangeably herein and include any human or nonhuman animal. The term "nonhuman animal" includes, but is not limited to, vertebrates such as nonhuman primates, sheep, dogs, and rodents such as mice, rats and guinea pigs. In some embodiments, the subject is a human.

As used herein, the term "administering" refers to the physical introduction of a therapeutic agent (or a precursor of the therapeutic agent that is metabolized or altered within the body of the subject to produce the therapeutic agent in vivo) to a subject, using any of the various methods and delivery systems known to those skilled in the art. Exemplary routes of include intravenous, intramuscular, subcutaneous, intraperitoneal, spinal or other parenteral routes of administration, for example by injection or infusion. The term "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent may be administered via a non-parenteral route, or orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The terms "cancer" and "tumor" are used interchangeably herein and refer to a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

A "therapeutically effective amount" or "therapeutically effective dose" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "weight based dose" as used herein refers to a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The term "fixed dose" as used herein refers to two or more different proteins in a single composition (e.g., anti-PD-1 antibody and fusion protein) are present in the composition in particular (fixed) ratios with each other. In some embodiments, the fixed dose is based on the weight (e.g., mg) of the proteins. In certain embodiments, the fixed dose is based on the concentration (e.g., mg/ml) of the proteins.

The term "flat dose" as used herein refers to a dose that is administered to a patient without regard for the weight or body surface area (BSA) of the patient. The flat dose is therefore not provided as a mg/kg dose, but rather as an absolute amount of the agent (e.g., the fusion protein and/or anti-PD-1 antibody). For example, a 60 kg person and a 100 kg person would receive the same dose of an antibody.

The term "antibody" is used herein in the broadest sense and encompasses fully assembled antibodies; functional antibody fragments and functional variants thereof that can bind antigen (e.g., Fab, F(ab')2, Fv, single chain variable fragment (scFv), single domain antibodies (e.g., VHH), diabodies, antibody chimeras, hybrid antibodies, bispecific antibodies, and the like); and non-antibody fragments that bind antigen (e.g., recombinant fibronectin domains) and recombinant polypeptides comprising the forgoing. Unless otherwise specified, references to the numbering of specific amino acid residue positions in an antibody are according to the EU numbering system, as described in Kabat et al., U.S. Dept. of Health and Human Services, Sequences of Proteins of Immunological Interest (1983) ("Kabat").

As used herein, the "variable region" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions and three complementarity determining regions.

As used herein, the term "complementarity determining region" refers to each of the regions of an antibody variable domain which are hypervariable in sequence and form structurally defined loops ("hypervariable loops"). Generally, native four-chain antibodies comprise six CDRs; three in the VH (H1, H2, H3), and three in the VL (L1, L2, L3). The CDRs have been described by Kabat et al., U.S. Dept. of Health and Human Services, Sequences of Proteins of Immunological Interest (1983) ("Kabat") and by Chothia et al., J Mol Biol 196:901-917 (1987), where the definitions include overlapping or subsets of amino acid residues when compared against each other. Nevertheless, application of either definition to refer to a CDR of an antibody is intended to be within the scope of the term as defined and used herein. Those skilled in the art can routinely determine which residues comprise a particular CDR given the variable region amino acid sequence of the antibody. Unless otherwise specified, CDRs are defined according to the Kabat system.

The term "fusion protein" and grammatical equivalents as used herein refers to a protein that comprises an amino acid sequence derived from at least two separate proteins. The amino acid sequence of the at least two separate proteins can be directly connected through a peptide bond; or can be operably connected through an amino acid linker. Therefore, the term fusion protein encompasses embodiments, wherein the amino acid sequence of e.g., Protein A is directly connected to the amino acid sequence of Protein B through a peptide bond (Protein A—Protein B), and embodiments, wherein the amino acid sequence of e.g., Protein A is operably connected to the amino acid sequence of Protein B through an amino acid linker (Protein A—linker—Protein B).

The term "fuse" and grammatical equivalents thereof as used herein refers to the operable connection of an amino acid sequence derived from one protein to the amino acid sequence derived from different protein. The term fuse encompasses both a direct connection of the two amino acid sequences through a peptide bond, and the indirect connection through an amino acid linker.

As used herein, the term "modification," with reference to a nucleic acid sequence, refers to a nucleic acid sequence that comprises at least one substitution, addition, or deletion of nucleotide compared to a reference nucleic acid sequence. As used herein, the term "modification," with reference to an amino acid sequence refers to an amino acid sequence that comprises at least one substitution, addition, or deletion of an amino acid residue compared to a reference nucleic acid sequence. Naturally occurring amino acid derivatives are not considered modified amino acids for purposes of determining percent identity of two amino acid sequences. For example, a naturally occurring modification of a glutamate amino acid residue to a pyroglutamate amino acid residue would not be considered an amino acid modification for purposes of determining percent identity of two amino acid sequences. Further, for example, a naturally occurring modification of a glutamate amino acid residue to a pyroglutamate amino acid residue would not be considered an amino acid "modification" as defined herein. Modifications can include the inclusion of non-naturally occurring amino acid residues.

The term "identical" or "percent identity" with reference to a nucleic acid sequence or amino acid sequence refers to at least two nucleic acid or at least two amino acid sequences or subsequences that have a specified percentage of nucleotides or amino acids, respectively, that are the same, when compared and aligned for maximum correspondence, as measured using a sequence comparison algorithm or by visual inspection. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Examples of algorithms that are suitable for determining percent sequence identity and sequence similarity are the BLAST and BLAST 2.0 algorithms, which are described in Altschuel et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information. The percent identity between two sequences can be determined using techniques similar to those described above, with or without allowing gaps. In calculating percent identity, typically only exact matches are counted. As described above, the percent identity is based on the amino acid matches between the smaller of two proteins.

Anti-PD1 Antibodies

In certain aspects, provided herein are methods of treating cancer comprising administering to a subject having cancer an antibody, or functional fragment or functional variant thereof, that specifically binds programmed death protein 1 (PD1), in combination with a fusion protein described herein. PD-1 is a member of the CD28 family of receptors, which includes CD28, CTLA-4, ICOS, PD-1, and BTLA. Two cell surface glycoprotein ligands for PD1 have been identified, programmed death ligand 1 (PDL1) and programmed death ligand 2 (PDL2), that are expressed on antigen-presenting cells as well as many human cancers and have been shown to down regulate T cell activation and cytokine secretion upon binding to PD1.

In some embodiments, the antibody is a full-length antibody, a single chain variable fragment (scFv), a scFv2, a scFv-Fc, a Fab, a Fab', a F(ab')2, a F(v), a single domain antibody, a single chain antibody, or a VHH.

Exemplary human monoclonal antibodies that bind specifically to PD1 with high affinity have been disclosed in U.S. Pat. No. 8,008,449. Each of the anti-PD-1 human monoclonal antibodies disclosed in U.S. Pat. No. 8,008,449 has been demonstrated to exhibit one or more of the following characteristics: (a) binds to human PD1 with a KD of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PDL1 and/or PDL2 to PD1; (h) stimulates antigen-specific memory responses; (i) stimulates antibody responses; and/or (j) inhibits tumor cell growth in vivo. Anti-PD1 antibodies usable in the present disclosure include monoclonal antibodies that bind specifically to human PD1 and exhibit at least one, at least two, at least three, at least four or at least five of the preceding characteristics. In other embodiments, the anti-PD-1 antibody is chosen from the human antibodies 17D8, 2D3, 4H1, 4A11, 7D3 or 5F4 described in U.S. Pat. No. 8,008,449. Other anti-PD1 monoclonal antibodies have been described in, for example, U.S. Pat. Nos. 6,808,710, 7,488,802, 8,168,757 and 8,354,509, and PCT Publication No. WO 2012/145493.

In some embodiments, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see e.g., WO2008/156712), PDR001 (Novartis; also known as spartalizumab; see e.g., WO 2015/112900), MEDI0680 (AstraZeneca; also known as AMP-514; see e.g., WO2012145493), cemiplimab (Regeneron; also known as REGN-2810; see e.g., WO2015112800), JS001 (Taizhou Junshi Pharma; see e.g., Si-Yang Liu et al., J. Hematol. Oncol. 70: 136 (2017)), BGB-A317 (Tislelizumab Beigene; see e.g., WO201535606 and US20150079109), INCSHR1210 (Jiangsu Hengrui Medicine; also known as SHR-1210; see e.g., WO2015085847; Si-Yang Liu et al., J. Hematol. Oncol. 70: 136 (2017)), TSR-042 (Tesaro Biopharmaceutical; also known as AB011; see e.g., WO2014179664), GLS-010 (Wuxi/Harbin Gloria Pharmaceuticals; also known as WBP3055; see e.g., Si-Yang Liu et al., J. Hematol. Oncol. 70: 136 (2017)), AM-0001 (Armo), STI-1110 (Sorrento Therapeutics; see e.g., WO2014194302), AGEN2034 (Agenus; see e.g., WO 2017/040790), MGA012 (Macrogenics, see e.g., WO201719846), IBI308 (Innovent; see e.g., WO2017024465, WO2017025016, WO2017132825, and WO2017133540), and BCD-100 (Biocad).

In some embodiments, the anti-PD1 antibody is selected from the group consisting of pembrolizumab, nivolumab, cemiplimab, spartalizumab, camrelizumab, tislelizumab, dostarlimab, cetrelimab, pidilizumab, MEDI0680, SSI-361, AMP-224, PDR001, PF-06801591, BGB-A317, TSR-042, AGEN-2034, A-0001, BGB-108, BI-754091, CBT-501, ENUM-003, ENUM-388D4, IBI-308, JNJ-63723283, JS-001, JTX-4014, JY-034, CLA-134, STIA-1110, 244C8, and 388D4.

In some embodiments, the anti-PD1 antibody is a functional fragment of pembrolizumab, nivolumab, spartalizumab, cemiplimab, camrelizumab, tislelizumab, dostarlimab, cetrelimab, pidilizumab, MEDI0680, SSI-361, AMP-224, PDR001, PF-06801591, BGB-A317, TSR-042, AGEN-2034, A-0001, BGB-108, BI-754091, CBT-501, ENUM-003, ENUM-388D4, IBI-308, JNJ-63723283, JS-001, JTX-4014, JY-034, CLA-134, STIA-1110, 244C8, or 388D4.

In some embodiments, the anti-PD1 antibody is a functional variant of pembrolizumab, nivolumab, spartalizumab, cemiplimab, camrelizumab, tislelizumab, dostarlimab, cetrelimab, pidilizumab, MEDI0680, SSI-361, AMP-224, PDR001, PF-06801591, BGB-A317, TSR-042, AGEN-2034, A-0001, BGB-108, BI-754091, CBT-501, ENUM-003, ENUM-388D4, IBI-308, JNJ-63723283, JS-001, JTX-4014, JY-034, CLA-134, STIA-1110, 244C8, or 388D4.

Pembrolizumab

In some embodiments, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD1. Pembrolizumab is described, for example, in U.S. Pat. No. 8,900,587. In some embodiments, the anti-PD1 antibody cross-competes with pembrolizumab. In some embodiments, the anti-PD1 antibody binds to the same epitope as pembrolizumab. In some embodiments, the anti-PD1 antibody has the same CDRs as pembrolizumab.

In some embodiments the anti-PD1 antibody comprises a variable heavy chain (VH) that comprises three complementarity determining regions: VH CDR1, VH CDR2, and VH CDR3. In some embodiments, the anti-PD1 antibody comprises a VH comprising a VH CDR1 that comprises an amino acid sequence of SEQ ID NO: 1, with 0, 1, 2, or 3 amino acid modifications; a VH CDR2 that comprises an amino acid sequence of SEQ ID NO: 2, with 0, 1, 2, or 3 amino acid modifications; and a VH CDR3 that comprises an amino acid sequence of SEQ ID NO: 3, with 0, 1, 2, or 3 amino acid modifications.

In some embodiments, the anti-PD1 antibody comprises a VH comprising a VH CDR1 that comprises the amino acid sequence of SEQ ID NO: 1, or the amino acid sequence of SEQ ID NO: 1 with 1, 2, or 3 amino acid modifications; a VH CDR2 that comprises the amino acid sequence of SEQ ID NO: 2, or the amino acid sequence of SEQ ID NO: 2 with 1, 2, or 3 amino acid modifications; and a VH CDR3 that comprises the amino acid sequence of SEQ ID NO: 3, or the amino acid sequence of SEQ ID NO: 3 with 1, 2, or 3 amino acid modifications.

In some embodiments, the anti-PD1 antibody comprises a VL comprising a VL CDR1 that comprises an amino acid sequence of SEQ ID NO: 4, with 0, 1, 2, or 3 amino acid modifications; a VL CDR2 that comprises an amino acid sequence of SEQ ID NO: 5, with 0, 1, 2, or 3 amino acid modifications; and a VL CDR3 that comprises an amino acid sequence of SEQ ID NO: 6, with 0, 1, 2, or 3 amino acid modifications.

In some embodiments, the anti-PD1 antibody comprises a VL comprising a VL CDR1 that comprises the amino acid sequence of SEQ ID NO: 4, or the amino acid sequence of SEQ ID NO: 4 with 1, 2, or 3 amino acid modifications; a VL CDR2 that comprises the amino acid sequence of SEQ ID NO: 5, or the amino acid sequence of SEQ ID NO: 5 with 1, 2, or 3 amino acid modifications; and a VL CDR3 that comprises the amino acid sequence of SEQ ID NO: 6, or the amino acid sequence of SEQ ID NO: 6 with 1, 2, or 3 amino acid modifications.

In some embodiments, the anti-PD1 antibody comprises a VH comprising a VH CDR1 that comprises an amino acid sequence of SEQ ID NO: 1, with 0, 1, 2, or 3 amino acid modifications; a VH CDR2 that comprises an amino acid sequence of SEQ ID NO: 2, with 0, 1, 2, or 3 amino acid modifications; and a VH CDR3 that comprises an amino acid sequence of SEQ ID NO: 3, with 0, 1, 2, or 3 amino acid modifications; and the anti-PD1 antibody comprises a VL that comprises comprising a VL CDR1 that comprises an amino acid sequence of SEQ ID NO: 4, with 0, 1, 2, or 3 amino acid modifications; a VL CDR2 that comprises an amino acid sequence of SEQ ID NO: 5, with 0, 1, 2, or 3 amino acid modifications; and a VL CDR3 that comprises an amino acid sequence of SEQ ID NO: 6, with 0, 1, 2, or 3 amino acid modifications.

In some embodiments, the anti-PD1 antibody comprises a VH comprising a VH CDR1 that comprises the amino acid sequence of SEQ ID NO: 1, or the amino acid sequence of SEQ ID NO: 1 with 1, 2, or 3 amino acid modifications; a VH CDR2 that comprises the amino acid sequence of SEQ ID NO: 2, or the amino acid sequence of SEQ ID NO: 2 with 1, 2, or 3 amino acid modifications; and a VH CDR3 that comprises the amino acid sequence of SEQ ID NO: 3, or the amino acid sequence of SEQ ID NO: 3 with 1, 2, or 3 amino acid modifications; and the anti-PD1 antibody comprises a VL comprising a VL CDR1 that comprises the amino acid sequence of SEQ ID NO: 4, or the amino acid sequence of SEQ ID NO: 4 with 1, 2, or 3 amino acid modifications; a VL CDR2 that comprises the amino acid sequence of SEQ ID NO: 5, or the amino acid sequence of SEQ ID NO: 5 with 1, 2, or 3 amino acid modifications; and a VL CDR3 that comprises the amino acid sequence of SEQ ID NO: 6, or the amino acid sequence of SEQ ID NO: 6 with 1, 2, or 3 amino acid modifications.

In some embodiments, the anti-PD1 antibody comprises a VH comprising a VH CDR1 that comprises an amino acid sequence at least 95%, 96%, 97%, 98%, 99%, or 100% identical to the amino acid sequence of SEQ ID NO: 1; a VH CDR2 that comprises an amino acid sequence at least 95%, 96%, 97%, 98%, 99%, or 100% of the amino acid sequence of SEQ ID NO: 2; and a VH CDR3 that comprises an amino acid sequence at least 95%, 96%, 97%, 98%, 99%, or 100% identical of the amino acid sequence of SEQ ID NO: 3.

In some embodiments, the anti-PD1 antibody comprises a VL comprising a VL CDR1 that comprises an amino acid sequence at least 95%, 96%, 97%, 98%, 99%, or 100% identical to the amino acid sequence of SEQ ID NO: 4; a VL CDR2 that comprises an amino acid sequence at least 95%, 96%, 97%, 98%, 99%, or 100% of the amino acid sequence of SEQ ID NO: 5; and a VL CDR3 that comprises an amino acid sequence at least 95%, 96%, 97%, 98%, 99%, or 100% identical of the amino acid sequence of SEQ ID NO: 6.

In some embodiments, the anti-PD1 antibody comprises a VH comprising a VH CDR1 that comprises an amino acid sequence at least 95%, 96%, 97%, 98%, 99%, or 100% identical to the amino acid sequence of SEQ ID NO: 1; a VH CDR2 that comprises an amino acid sequence at least 95%, 96%, 97%, 98%, 99%, or 100% identical to the amino acid sequence of SEQ ID NO: 2; and a VH CDR3 that comprises an amino acid sequence at least 95%, 96%, 97%, 98%, 99%, or 100% identical to the amino acid sequence of SEQ ID NO: 3; and the anti-PD1 antibody comprises a VL comprising a VL CDR1 that comprises an amino acid sequence at least 95%, 96%, 97%, 98%, 99%, or 100% identical to the amino acid sequence of SEQ ID NO: 4; a VL CDR2 that comprises an amino acid sequence at least 95%, 96%, 97%, 98%, 99%, or 100% identical to the amino acid sequence of SEQ ID NO: 5; and a VL CDR3 that comprises an amino acid sequence at least 95%, 96%, 97%, 98%, 99%, or 100% identical to the amino acid sequence of SEQ ID NO: 6.

In some embodiments, the anti-PD1 antibody comprises a VH at least 90%, 91%, 92%, 93%, 94%, 95%, 96%, 97%, 98%, 99%, or 100% identical to the amino acid sequence of SEQ ID NO: 7. In some embodiments, the anti-PD1 antibody comprises a VL at least 90%, 91%, 92%, 93%, 94%, 95%, 96%, 97%, 98%, 99%, or 100% identical to the amino acid sequence of SEQ ID NO: 8. In some embodiments, the anti-PD1 antibody comprises a VH at least 90%, 91%, 92%, 93%, 94%, 95%, 96%, 97%, 98%, 99%, or 100% identical to the amino acid sequence of SEQ ID NO: 7; and a VL at least 90%, 91%, 92%, 93%, 94%, 95%, 96%, 97%, 98%, 99%, or 100% identical to the amino acid sequence of SEQ ID NO: 8.

In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 10. In some embodiments, the anti-PD1 antibody comprises a light chain that comprises an amino acid sequence at least 90%, 91%, 92%, 93%, 94%, 95%, 96%, 97%, 98%, 99%, or 100% identical to the amino acid sequence of SEQ ID NO: 11. In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 10; and a light chain that comprises an amino acid sequence at least 90%, 91%, 92%, 93%, 94%, 95%, 96%, 97%, 98%, 99%, or 100% identical to the amino acid sequence of SEQ ID NO: 11.

In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 9. In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 9; and a light chain that comprises an amino acid sequence at least 90%, 91%, 92%, 93%, 94%, 95%, 96%, 97%, 98%, 99%, or 100% identical to the amino acid sequence of SEQ ID NO: 11.

Nivolumab

In some embodiments, the anti-PD1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD1 ligands (PDL1 and PDL2), thereby blocking the down-regulation of antitumor T-cell functions (U.S. Pat. No. 8,008,449; Wang et al., 2014 Cancer Immunol Res. 2(9): 846-56; referred to as 5C4 in WO 2006/121168). In some embodiments, the anti-PD1 antibody cross-competes with nivolumab. In some embodiments, the anti-PD-1 antibody binds to the same epitope as nivolumab. In some embodiments, the anti-PD-1 antibody has the same CDRs as nivolumab.

In some embodiments the anti-PD1 antibody comprises a variable heavy chain (VH) that comprises three complementarity determining regions: VH CDR1, VH CDR2, and VH CDR3. In some embodiments, the anti-PD1 antibody comprises a VH comprising a VH CDR1 that comprises an amino acid sequence of SEQ ID NO: 12, with 0, 1, 2, or 3 amino acid modifications; a VH CDR2 that comprises an amino acid sequence of SEQ ID NO: 13, with 0, 1, 2, or 3 amino acid modifications; and a VH CDR3 that comprises an amino acid sequence of SEQ ID NO: 14, with 0, 1, 2, or 3 amino acid modifications.

In some embodiments, the anti-PD1 antibody comprises a VH comprising a VH CDR1 that comprises the amino acid sequence of SEQ ID NO: 12, or the amino acid sequence of SEQ ID NO: 12 with 1, 2, or 3 amino acid modifications; a VH CDR2 that comprises the amino acid sequence of SEQ ID NO: 13, or the amino acid sequence of SEQ ID NO: 13 with 1, 2, or 3 amino acid modifications; and a VH CDR3 that comprises the amino acid sequence of SEQ ID NO: 14, or the amino acid sequence of SEQ ID NO: 14 with 1, 2, or 3 amino acid modifications.

In some embodiments, the anti-PD1 antibody comprises a VL comprising a VL CDR1 that comprises an amino acid sequence of SEQ ID NO: 15, with 0, 1, 2, or 3 amino acid modifications; a VL CDR2 that comprises an amino acid sequence of SEQ ID NO: 16, with 0, 1, 2, or 3 amino acid modifications; and a VL CDR3 that comprises an amino acid sequence of SEQ ID NO: 17, with 0, 1, 2, or 3 amino acid modifications. In some embodiments, the anti-PD1 antibody comprises a VL comprising a VL CDR1 that comprises the amino acid sequence of SEQ ID NO: 15, or the amino acid sequence of SEQ ID NO: 15 with 1, 2, or 3 amino acid modifications; a VL CDR2 that comprises the amino acid sequence of SEQ ID NO: 16, or the amino acid sequence of SEQ ID NO: 16 with 1, 2, or 3 amino acid modifications; and a VL CDR3 that comprises the amino acid sequence of SEQ ID NO: 17, or the amino acid sequence of SEQ ID NO: 17 with 1, 2, or 3 amino acid modifications.

In some embodiments, the anti-PD1 antibody comprises a VH comprising a VH CDR1 that comprises an amino acid sequence of SEQ ID NO: 12, with 0, 1, 2, or 3 amino acid modifications; a VH CDR2 that comprises an amino acid sequence of SEQ ID NO: 13, with 0, 1, 2, or 3 amino acid modifications; and a VH CDR3 that comprises an amino acid sequence of SEQ ID NO: 14, with 0, 1, 2, or 3 amino acid modifications; and the anti-PD1 antibody comprises a VL that comprises a VL CDR1 that comprises an amino acid sequence of SEQ ID NO: 15, with 0, 1, 2, or 3 amino acid modifications; a VL CDR2 that comprises an amino acid sequence of SEQ ID NO: 16, with 0, 1, 2, or 3 amino acid modifications; and a VL CDR3 that comprises an amino acid sequence of SEQ ID NO: 17, with 0, 1, 2, or 3 amino acid modifications.

In some embodiments, the anti-PD1 antibody comprises a VH comprising a VH CDR1 that comprises the amino acid sequence of SEQ ID NO: 12, or the amino acid sequence of SEQ ID NO: 12 with 1, 2, or 3 amino acid modifications; a VH CDR2 that comprises the amino acid sequence of SEQ ID NO: 13, or the amino acid sequence of SEQ ID NO: 13 with 1, 2, or 3 amino acid modifications; and a VH CDR3 that comprises the amino acid sequence of SEQ ID NO: 14, or the amino acid sequence of SEQ ID NO: 14 with 1, 2, or 3 amino acid modifications; and a VL that comprises a VL CDR1 that comprises an amino acid sequence of SEQ ID NO: 15, or the amino acid sequence of SEQ ID NO: 15 with 1, 2, or 3 amino acid modifications; a VL CDR2 that comprises an amino acid sequence of SEQ ID NO: 16, or the amino acid sequence of SEQ ID NO: 16 with 1, 2, or 3 amino acid modifications; and a VL CDR3 that comprises an amino acid sequence of SEQ ID NO: 17, or the amino acid sequence of SEQ ID NO: 17 with 1, 2, or 3 amino acid modifications.

In some embodiments, the anti-PD1 antibody comprises a VH comprising a VH CDR1 that comprises an amino acid sequence at least 95%, 96%, 97%, 98%, 99%, or 100% identical to the amino acid sequence of SEQ ID NO: 12; a VH CDR2 that comprises an amino acid sequence at least 95%, 96%, 97%, 98%, 99%, or 100% identical to the amino acid sequence of SEQ ID NO: 13; and a VH CDR3 that comprises an amino acid sequence at least 95%, 96%, 97%, 98%, 99%, or 100% identical to the amino acid sequence of SEQ ID NO: 14.

In some embodiments, the anti-PD1 antibody comprises a VL comprising a VL CDR1 that comprises an amino acid sequence at least 95%, 96%, 97%, 98%, 99%, or 100% identical to the amino acid sequence of SEQ ID NO: 15; a VL CDR2 that comprises an amino acid sequence at least 95%, 96%, 97%, 98%, 99%, or 100% identical to the amino acid sequence of SEQ ID NO: 16; and a VL CDR3 that comprises an amino acid sequence at least 95%, 96%, 97%, 98%, 99%, or 100% identical to the amino acid sequence of SEQ ID NO: 17.

In some embodiments, the anti-PD1 antibody comprises a VH comprising a VH CDR1 that comprises an amino acid sequence at least 95%, 96%, 97%, 98%, 99%, or 100% identical to the amino acid sequence of SEQ ID NO: 12; a VH CDR2 that comprises an amino acid sequence at least 95%, 96%, 97%, 98%, 99%, or 100% identical to the amino acid sequence of SEQ ID NO: 13; and a VH CDR3 that comprises an amino acid sequence at least 95%, 96%, 97%, 98%, 99%, or 100% identical to the amino acid sequence of SEQ ID NO: 14; and the anti-PD1 antibody comprises a VL comprising a VL CDR1 that comprises an amino acid sequence at least 95%, 96%, 97%, 98%, 99%, or 100% identical to the amino acid sequence of SEQ ID NO: 15; a VL CDR2 that comprises an amino acid sequence at least 95%, 96%, 97%, 98%, 99%, or 100% identical to the amino acid sequence of SEQ ID NO: 16; and a VL CDR3 that comprises an amino acid sequence at least 95%, 96%, 97%, 98%, 99%, or 100% identical to the amino acid sequence of SEQ ID NO: 17.

In some embodiments, the anti-PD1 antibody comprises a VH at least 90%, 91%, 92%, 93%, 94%, 95%, 96%, 97%, 98%, 99%, or 100% identical to the amino acid sequence of SEQ ID NO: 18. In some embodiments, the anti-PD1 antibody comprises a VL at least 90%, 91%, 92%, 93%, 94%, 95%, 96%, 97%, 98%, 99%, or 100% identical to the amino acid sequence of SEQ ID NO: 19. In some embodiments, the anti-PD1 antibody comprises a VH at least 90%, 91%, 92%, 93%, 94%, 95%, 96%, 97%, 98%, 99%, or 100% identical to the amino acid sequence of SEQ ID NO: 18; and a VL at least 90%, 91%, 92%, 93%, 94%, 95%, 96%, 97%, 98%, 99%, or 100% identical to the amino acid sequence of SEQ ID NO: 19.

In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 21. In some embodiments, the anti-PD1 antibody comprises a light chain that comprises an amino acid sequence at least 90%, 91%, 92%, 93%, 94%, 95%, 96%, 97%, 98%, 99%, or 100% identical to the amino acid sequence of SEQ ID NO: 22. In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 21; and a light chain that comprises an amino acid sequence at least 90%, 91%, 92%, 93%, 94%, 95%, 96%, 97%, 98%, 99%, or 100% identical to the amino acid sequence of SEQ ID NO: 22.

In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 20. In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 20; and a light chain that comprises an amino acid sequence at least 90%, 91%, 92%, 93%, 94%, 95%, 96%, 97%, 98%, 99%, or 100% identical to the amino acid sequence of SEQ ID NO: 22.

Cemiplimab

In some embodiments, the anti-PD1 antibody is cemiplimab, which is a monoclonal antibody against the PD1 receptor. In some embodiments, the anti-PD1 antibody cross-competes with cemiplimab. In some embodiments, the anti-PD-1 antibody binds to the same epitope as cemiplimab. In some embodiments, the anti-PD-1 antibody has the same CDR regions as cemiplimab.

In some embodiments the anti-PD1 antibody comprises a variable heavy chain (VH) that comprises three complementarity determining regions: VH CDR1, VH CDR2, and VH CDR3. In some embodiments, the anti-PD1 antibody comprises a VH comprising a VH CDR1 that comprises an amino acid sequence of SEQ ID NO: 23 with 0, 1, 2, or 3 amino acid modifications; a VH CDR2 that comprises an amino acid sequence of SEQ ID NO: 24, with 0, 1, 2, or 3 amino acid modifications; and a VH CDR3 that comprises an amino acid sequence of SEQ ID NO: 25, with 0, 1, 2, or 3 amino acid modifications. In some embodiments, the anti-PD1 antibody comprises a VH comprising a VH CDR1 that comprises the amino acid sequence of SEQ ID NO: 23, or the amino acid sequence of SEQ ID NO: 23 with 1, 2, or 3 amino acid modifications; a VH CDR2 that comprises the amino acid sequence of SEQ ID NO: 24, or the amino acid sequence of SEQ ID NO: 24 with 1, 2, or 3 amino acid modifications; and a VH CDR3 that comprises the amino acid sequence of SEQ ID NO: 25, or the amino acid sequence of SEQ ID NO: 25 with 1, 2, or 3 amino acid modifications.

In some embodiments the anti-PD1 antibody comprises a variable light chain (VL) that comprises three complementarity determining regions: VL CDR1, VL CDR2, and VL CDR3. In some embodiments, the anti-PD1 antibody comprises a VL comprising a VL CDR1 that comprises an amino acid sequence of SEQ ID NO: 26, with 0, 1, 2, or 3 amino acid modifications; a VL CDR2 that comprises an amino acid sequence of SEQ ID NO: 27, with 0, 1, 2, or 3 amino acid modifications; and a VL CDR3 that comprises an amino acid sequence of SEQ ID NO: 28, with 0, 1, 2, or 3 amino acid modifications. In some embodiments, the anti-PD1 antibody comprises a VL comprising a VL CDR1 that comprises the amino acid sequence of SEQ ID NO: 26, or the amino acid sequence of SEQ ID NO: 26 with 1, 2, or 3 amino acid modifications; a VL CDR2 that comprises the amino acid sequence of SEQ ID NO: 27, or the amino acid sequence of SEQ ID NO: 27 with 1, 2, or 3 amino acid modifications; and a VL CDR3 that comprises the amino acid sequence of SEQ ID NO: 28, or the amino acid sequence of SEQ ID NO: 28 with 1, 2, or 3 amino acid modifications.

In some embodiments, the anti-PD1 antibody comprises a VH comprising a VH CDR1 that comprises an amino acid sequence of SEQ ID NO: 23, with 0, 1, 2, or 3 amino acid modifications; a VH CDR2 that comprises an amino acid sequence of SEQ ID NO: 24, with 0, 1, 2, or 3 amino acid modifications; and a VH CDR3 that comprises an amino acid sequence of SEQ ID NO: 25, with 0, 1, 2, or 3 amino acid modifications; and a VL comprising a VL CDR1 that comprises an amino acid sequence of SEQ ID NO: 26, with 0, 1, 2, or 3 amino acid modifications; a VL CDR2 that comprises an amino acid sequence of SEQ ID NO: 27, with 0, 1, 2, or 3 amino acid modifications; and a VL CDR3 that comprises an amino acid sequence of SEQ ID NO: 28, with 0, 1, 2, or 3 amino acid modifications.

In some embodiments, the anti-PD1 antibody comprises a VH comprising a VH CDR1 that comprises the amino acid sequence of SEQ ID NO: 23, or the amino acid sequence of SEQ ID NO: 26 with 1, 2, or 3 amino acid modifications; a VH CDR2 that comprises the amino acid sequence of SEQ ID NO: 24, or the amino acid sequence of SEQ ID NO: 24 with 1, 2, or 3 amino acid modifications; and a VH CDR3 that comprises the amino acid sequence of SEQ ID NO: 25, or the amino acid sequence of SEQ ID NO: 25 with 1, 2, or 3 amino acid modifications; and a VL comprising a VL CDR1 that comprises the amino acid sequence of SEQ ID NO: 26, or the amino acid sequence of SEQ ID NO: 26 with 1, 2, or 3 amino acid modifications; a VL CDR2 that comprises the amino acid sequence of SEQ ID NO: 27, or the amino acid sequence of SEQ ID NO: 27 with 1, 2, or 3 amino acid modifications; and a VL CDR3 that comprises the amino acid sequence of SEQ ID NO: 28, or the amino acid sequence of SEQ ID NO: 28 with 1, 2, or 3 amino acid modifications.

In some embodiments, the anti-PD1 antibody comprises a VH comprising a VH CDR1 that comprises an amino acid sequence at least 95%, 96%, 97%, 98%, 99%, or 100% identical to the amino acid sequence of SEQ ID NO: 23; a VH CDR2 that comprises an amino acid sequence at least 95%, 96%, 97%, 98%, 99%, or 100% identical to the amino acid sequence of SEQ ID NO: 24; and a VH CDR3 that comprises an amino acid sequence at least 95%, 96%, 97%, 98%, 99%, or 100% identical to the amino acid sequence of SEQ ID NO: 25.

In some embodiments, the anti-PD1 antibody comprises a VL comprising a VL CDR1 that comprises an amino acid sequence at least 95%, 96%, 97%, 98%, 99%, or 100% identical to the amino acid sequence of SEQ ID NO: 26; a VL CDR2 that comprises an amino acid sequence at least 95%, 96%, 97%, 98%, 99%, or 100% identical to the amino acid sequence of SEQ ID NO: 27; and a VL CDR3 that comprises an amino acid sequence at least 95%, 96%, 97%, 98%, 99%, or 100% identical to the amino acid sequence of SEQ ID NO: 28.

In some embodiments, the anti-PD1 antibody comprises a VH comprising a VH CDR1 that comprises an amino acid sequence at least 95%, 96%, 97%, 98%, 99%, or 100% identical to the amino acid sequence of SEQ ID NO: 23; a VH CDR2 that comprises an amino acid sequence at least 95%, 96%, 97%, 98%, 99%, or 100% identical to the amino acid sequence of SEQ ID NO: 24; and a VH CDR3 that comprises an amino acid sequence at least 95%, 96%, 97%, 98%, 99%, or 100% identical to the amino acid sequence of SEQ ID NO: 25; and the anti-PD1 antibody comprises a VL comprising a VL CDR1 that comprises an amino acid sequence at least 95%, 96%, 97%, 98%, 99%, or 100% identical to the amino acid sequence of SEQ ID NO: 26; a VL CDR2 that comprises an amino acid sequence at least 95%, 96%, 97%, 98%, 99%, or 100% identical to the amino acid sequence of SEQ ID NO: 27; and a VL CDR3 that comprises an amino acid sequence at least 95%, 96%, 97%, 98%, 99%, or 100% identical to the amino acid sequence of SEQ ID NO: 28.

In some embodiments, the anti-PD1 antibody comprises a VH at least 90%, 91%, 92%, 93%, 94%, 95%, 96%, 97%, 98%, 99%, or 100% identical to the amino acid sequence of SEQ ID NO: 29. In some embodiments, the anti-PD1 antibody comprises a VL at least 90%, 91%, 92%, 93%, 94%, 95%, 96%, 97%, 98%, 99%, or 100% identical to the amino acid sequence of SEQ ID NO: 30. In some embodiments, the anti-PD1 antibody comprises a VH at least 90%, 91%, 92%, 93%, 94%, 95%, 96%, 97%, 98%, 99%, or 100% identical to the amino acid sequence of SEQ ID NO: 29; and a VL at least 90%, 91%, 92%, 93%, 94%, 95%, 96%, 97%, 98%, 99%, or 100% identical to the amino acid sequence of SEQ ID NO: 30.

In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 32. In some embodiments, the anti-PD1 antibody comprises a light chain that comprises an amino acid sequence at least 90%, 91%, 92%, 93%, 94%, 95%, 96%, 97%, 98%, 99%, or 100% identical to the amino acid sequence of SEQ ID NO: 33. In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 32; and a light chain that comprises an amino acid sequence at least 90%, 91%, 92%, 93%, 94%, 95%, 96%, 97%, 98%, 99%, or 100% identical to the amino acid sequence of SEQ ID NO: 33.

In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 31. In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 31; and a light chain that comprises an amino acid sequence at least 90%, 91%, 92%, 93%, 94%, 95%, 96%, 97%, 98%, 99%, or 100% identical to the amino acid sequence of SEQ ID NO: 33.

In some embodiments, the anti-PD1 antibody comprises an antibody in Table 1. In some embodiments, the anti-PD1 antibody is an antibody in Table 1.

In some embodiments, the anti-PD1 antibody comprises a VH comprising a VH CDR1 that comprises an amino acid sequence at least 95%, 96%, 97%, 98%, 99%, or 100% identical to the amino acid sequence of a VH CDR1 in Table 1; a VH CDR2 that comprises an amino acid sequence at least 95%, 96%, 97%, 98%, 99%, or 100% identical to the amino acid sequence of a VH CDR2 in Table 1; and a VH CDR3 that comprises an amino acid sequence at least 95%, 96%, 97%, 98%, 99%, or 100% identical to the amino acid sequence of a VH CDR3 in Table 1.

In some embodiments, the anti-PD1 antibody comprises a VL comprising a VL CDR1 that comprises an amino acid sequence at least 95%, 96%, 97%, 98%, 99%, or 100% identical to the amino acid sequence of a VL CDR1 in Table 1; a VL CDR2 that comprises an amino acid sequence at least 95%, 96%, 97%, 98%, 99%, or 100% identical to the amino acid sequence of a VL CDR2 in Table 1; and a VL CDR3 that comprises an amino acid sequence at least 95%, 96%, 97%, 98%, 99%, or 100% identical to the amino acid sequence of a VL CDR3 in Table 1.

In some embodiments, the anti-PD1 antibody comprises a VH comprising a VH CDR1 that comprises an amino acid sequence at least 95%, 96%, 97%, 98%, 99%, or 100% identical to the amino acid sequence of a VH CDR1 in Table 1; a VH CDR2 that comprises an amino acid sequence at least 95%, 96%, 97%, 98%, 99%, or 100% identical to the amino acid sequence of a VH CDR2 in Table 1; a VH CDR3 that comprises an amino acid sequence at least 95%, 96%, 97%, 98%, 99%, or 100% identical to the amino acid sequence of a VH CDR3 in Table 1; a VL comprising a VL CDR1 that comprises an amino acid sequence at least 95%, 96%, 97%, 98%, 99%, or 100% identical to the amino acid sequence of a VL CDR1 in Table 1; a VL CDR2 that comprises an amino acid sequence at least 95%, 96%, 97%, 98%, 99%, or 100% identical to the amino acid sequence of a VL CDR2 in Table 1; and a VL CDR3 that comprises an amino acid sequence at least 95%, 96%, 97%, 98%, 99%, or 100% identical to the amino acid sequence of a VL CDR3 in Table 1.

In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of a heavy chain in Table 1. In some embodiments, the anti-PD1 antibody comprises a light chain that comprises an amino acid sequence at least 90%, 91%, 92%, 93%, 94%, 95%, 96%, 97%, 98%, 99%, or 100% identical to the amino acid sequence of a light chain in Table 1. In some embodiments, the anti-PD1 antibody comprises a heavy chain that comprises an amino acid sequence at least 90%, 91%, 92%, 93%, 94%, 95%, 96%, 97%, 98%, 99%, or 100% identical to the amino acid sequence of a heavy chain in Table 1; and a light chain that comprises an amino acid sequence at least 90%, 91%, 92%, 93%, 94%, 95%, 96%, 97%, 98%, 99%, or 100% identical to the amino acid sequence of a light chain in Table 1.

In some embodiments, the anti-PD1 antibody comprises a VH that comprises an amino acid sequence at least 95%, 96%, 97%, 98%, 99%, or 100% identical to the amino acid sequence of a VH of an antibody in Table 1. In some embodiments, the anti-PD1 antibody comprises a VL that comprises an amino acid sequence at least 95%, 96%, 97%, 98%, 99%, or 100% identical to the amino acid sequence of an antibody in Table 1. In some embodiments, the anti-PD1 antibody comprises a VH that comprises an amino acid sequence at least 95%, 96%, 97%, 98%, 99%, or 100% identical to the amino acid sequence of a VH of an antibody in Table 1; and a VL that comprises an amino acid sequence at least 95%, 96%, 97%, 98%, 99%, or 100% identical to the amino acid sequence of an antibody in Table 1.

TABLE 1

Exemplary Anti-PD1 Antibodies

| Antibody | Region | Amino Acid Sequence | SEQ ID NO |
|---|---|---|---|
| Pembrolizumab (CDRs defined according to Kabat) | VH CDR1 | NYYMY | 1 |
| | VH CDR2 | GINPSNGGTNFNEKFKN | 2 |
| | VH CDR3 | RDYRFDMGEDY | 3 |
| | VL CDR1 | RASKGVSTSGYSYLH | 4 |
| | VL CDR2 | LASYLES | 5 |
| | VL CDR3 | QHSRDLPLT | 6 |
| | VH | QVQLVQSGVEVKKPGASVKVSCKASGYTFTNYYMYWVRQAPGQ GLEWMGGINPSNGGTNFNEKFKNRVTLTTDSSTTTAYMELKSL QFDDTAVYYCARRDYRFDMGFDYWGQGTTVTVSS | 7 |
| | VL | EIVLTQSPATLSLSPGERATLSCRASKGVSTSGYSYLHWYQQK PGQAPRLLIYLASYLESGVPARFSGSGSGTDFTLTISSLEPED FAVYYCQHSRDLPLTFGGGTKVEIK | 8 |
| | HC-A | QVQLVQSGVEVKKPGASVKVSCKASGYTFTNYYMYWVRQAPGQ GLEWMGGINPSNGGTNFNEKFKNRVTLTTDSSTTTAYMELKSL QFDDTAVYYCARRDYRFDMGFDYWGQGTTVTVSSASTKGPSVF PLAPCSRSTSESTAALGCLVKDYFPEPVTVSWNSGALTSGVHT FPAVLQSSGLYSLSSVVTVPSSSLGTKTYTCNVDHKPSNTKVD KRVESKYGPPCPPCPAPEFLGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPR EPQVYTLPPSQEEMTKNQVSLTCLVKGFYPSDIAVEWESNGQP ENNYKTTPPVLDSDGSFFLYSRLTVDKSRWQEGNVFSCSVMHE ALHNHYTQKSLSLSLGK | 9 |
| | HC-B (No C-terminal Lysine) | QVQLVQSGVEVKKPGASVKVSCKASGYTFTNYYMYWVRQAPGQ GLEWMGGINPSNGGTNFNEKFKNRVTLTTDSSTTTAYMELKSL QFDDTAVYYCARRDYRFDMGFDYWGQGTTVTVSSASTKGPSVF PLAPCSRSTSESTAALGCLVKDYFPEPVTVSWNSGALTSGVHT FPAVLQSSGLYSLSSVVTVPSSSLGTKTYTCNVDHKPSNTKVD KRVESKYGPPCPPCPAPEFLGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPR EPQVYTLPPSQEEMTKNQVSLTCLVKGFYPSDIAVEWESNGQP ENNYKTTPPVLDSDGSFFLYSRLTVDKSRWQEGNVFSCSVMHE ALHNHYTQKSLSLSLG | 10 |
| | LC | EIVLTQSPATLSLSPGERATLSCRASKGVSTSGYSYLHWYQQK PGQAPRLLIYLASYLESGVPARFSGSGSGTDFTLTISSLEPED FAVYYCQHSRDLPLTFGGGTKVEIKRTVAAPSVFIFPPSDEQL KSGTASVVCLLNNFYPREAKVQWKVDNALQSGNSQESVTEQDS KDSTYSLSSTLTLSKADYEKHKVYACEVTHQGLSSPVTKSENR GEC | 11 |

TABLE 1-continued

| Exemplary Anti-PD1 Antibodies | | | |
|---|---|---|---|
| Antibody | Region | Amino Acid Sequence | SEQ ID NO |
| Nivolumab (CDRs defined according to Kabat) | VH CDR1 | NSGMH | 12 |
| | VH CDR2 | VIWYDGSKRYYADSVKG | 13 |
| | VH CDR3 | NDDY | 14 |
| | VL CDR1 | RASQSVSSYLA | 15 |
| | VL CDR2 | DASNRAT | 16 |
| | VL CDR3 | QQSSNWPRT | 17 |
| | VH | QVQLVESGGGVVQPGRSLRLDCKASGITFSNSGMHWVRQAPGK GLEWVAVIWYDGSKRYYADSVKGRFTISRDNSKNTLFLQMNSL RAEDTAVYYCATNDDYWGQGTLVTVSS | 18 |
| | VL | EIVLTQSPATLSLSPGERATLSCRASQSVSSYLAWYQQKPGQA PRLLIYDASNRATGIPARFSGSGSGTDFTLTISSLEPEDFAVY YCQQSSNWPRTFGQGTKVEIK | 19 |
| | HC-A | QVQLVESGGGVVQPGRSLRLDCKASGITFSNSGMHWVRQAPGK GLEWVAVIWYDGSKRYYADSVKGRFTISRDNSKNTLFLQMNSL RAEDTAVYYCATNDDYWGQGTLVTVSSASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLGK | 20 |
| | HC-B (No C-terminal Lysine) | QVQLVESGGGVVQPGRSLRLDCKASGITFSNSGMHWVRQAPGK GLEWVAVIWYDGSKRYYADSVKGRFTISRDNSKNTLFLQMNSL RAEDTAVYYCATNDDYWGQGTLVTVSSASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG | 21 |
| | LC | EIVLTQSPATLSLSPGERATLSCRASQSVSSYLAWYQQKPGQA PRLLIYDASNRATGIPARFSGSGSGTDFTLTISSLEPEDFAVY YCQQSSNWPRTFGQGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | 22 |
| Cemiplimab (CDRs defined according to Kabat) | VH CDR1 | NFGMT | 23 |
| | VH CDR2 | GISGGGRDTYFADSVKG | 24 |
| | VH CDR3 | WGNIYFDY | 25 |
| | VL CDR1 | RASLSINTFLN | 26 |
| | VL CDR2 | AASSLHG | 27 |
| | VL CDR3 | QQSSNTPFT | 28 |
| | VH | EVQLLESGGVLVQPGGSLRLSCAASGFTFSNFGMTWVRQAPGK GLEWVSGISGGGRDTYFADSVKGRFTISRDNSKNTLYLQMNSL KGEDTAVYYCVKWGNIYFDYWGQGTLVT | 29 |
| | VL | DIQMTQSPSSLSASVGDSITITCRASLSINTFLNWYQQKPGKA PNLLIYAASSLHGGVPSRFSGSGSGTDFTLTIRTLQPEDFATY YCQQSSNTPFTFGPGTVVDFR | 30 |

TABLE 1-continued

| Exemplary Anti-PD1 Antibodies | | | |
|---|---|---|---|
| Antibody | Region | Amino Acid Sequence | SEQ ID NO |
| | HC-A | EVQLLESGGVLVQPGGSLRLSCAASGFTFSNFGMTWVRQAPGK<br>GLEWVSGISGGGRDTYFADSVKGRFTISRDNSKNTLYLQMNSL<br>KGEDTAVYYCVKWGNIYFDYWGQGTLVTVSSASTKGPSVFPLA<br>PCSRSTSESTAALGCLVKDYFPEPVTVSWNSGALTSGVHTFPA<br>VLQSSGLYSLSSVVTVPSSSLGTKTYTCNVDHKPSNTKVDKRV<br>ESKYGPPCPPCPAPEFLGGPSVFLFPPKPKDTLMISRTPEVTC<br>VVVDVSQEDPEVQFNWYVDGVEVHNAKTKPREEQFNSTYRVVS<br>VLTVLHQDWLNGKEYKCKVSNKGLPSSIEKTISKAKGQPREPQ<br>VYTLPPSQEEMTKNQVSLTCLVKGFYPSDIAVEWESNGQPENN<br>YKTTPPVLDSDGSFFLYSRLTVDKSRWQEGNVFSCSVMHEALH<br>NHYTQKSLSLSLGK | 31 |
| | HC-B (No C-terminal Lysine) | EVQLLESGGVLVQPGGSLRLSCAASGFTFSNFGMTWVRQAPGK<br>GLEWVSGISGGGRDTYFADSVKGRFTISRDNSKNTLYLQMNSL<br>KGEDTAVYYCVKWGNIYFDYWGQGTLVTVSSASTKGPSVFPLA<br>PCSRSTSESTAALGCLVKDYFPEPVTVSWNSGALTSGVHTFPA<br>VLQSSGLYSLSSVVTVPSSSLGTKTYTCNVDHKPSNTKVDKRV<br>ESKYGPPCPPCPAPEFLGGPSVFLFPPKPKDTLMISRTPEVTC<br>VVVDVSQEDPEVQFNWYVDGVEVHNAKTKPREEQFNSTYRVVS<br>VLTVLHQDWLNGKEYKCKVSNKGLPSSIEKTISKAKGQPREPQ<br>VYTLPPSQEEMTKNQVSLTCLVKGFYPSDIAVEWESNGQPENN<br>YKTTPPVLDSDGSFFLYSRLTVDKSRWQEGNVFSCSVMHEALH<br>NHYTQKSLSLSLG | 32 |
| | LC | DIQMTQSPSSLSASVGDSITITCRASLSINTFLNWYQQKPGKA<br>PNLLIYAASSLHGGVPSRFSGSGSGTDFTLTIRTLQPEDFATY<br>YCQQSSNTPFTFGPGTVVDFRRTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVTKSENRGEC | 33 |

Methods of Making Anti-PD1 Antibodies

Anti-PD1 antibodies described herein can be made by any conventional technique known in the art, for example, recombinant techniques or chemical synthesis (e.g., solid phase peptide synthesis). In one embodiments, the anti-PD1 antibody is made through recombinant expression in a cell. Briefly, the anti-PD1 antibody can be made by synthesizing the DNA encoding the anti-PD1 antibody and cloning the DNA into any suitable expression vector. Numerous cloning vectors are known to those of skill in the art, and the selection of an appropriate cloning vector is a matter of choice. The gene can be placed under the control of a promoter, ribosome binding site (for bacterial expression) and, optionally, an operator, so that the DNA sequence encoding the fusion protein is transcribed into RNA in the host cell transformed by a vector containing this expression construction. The coding sequence may or may not contain a signal peptide or leader sequence. Heterologous leader sequences can be added to the coding sequence that causes the secretion of the expressed polypeptide from the host organism. Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

The expression vector may then used to transform an appropriate host cell. A number of mammalian cell lines are known in the art and include immortalized cell lines available from the American Type Culture Collection (ATCC), such as, but not limited to, Chinese hamster ovary (CHO) cells, CHO-suspension cells (CHO-S), HeLa cells, HEK293, baby hamster kidney (BHK) cells, monkey kidney cells (COS), VERO, HepG2, MadinDarby bovine kidney (MDBK) cells, NOS, U2OS, A549, HT1080, CAD, P19, NIH3T3, L929, N2a, MCF-7, Y79, SO-Rb50, DUKX-X11, and J558L. In some embodiments, the anti-PD1 antibody is produced in CHO or CHO-S cells.

Depending on the expression system and host selected, the anti-PD1 antibody is produced by growing host cells transformed by an expression vector described above under conditions whereby the anti-PD1 antibody is expressed. The anti-PD1 antibody is then isolated from the host cells and purified. If the expression system secretes the anti-PD1 antibody into growth media, the anti-PD1 antibody can be purified directly from the media. If the anti-PD1 antibody is not secreted, it is isolated from cell lysates. The selection of the appropriate growth conditions and recovery methods are within the skill of the art. Once purified, the amino acid sequences of the anti-PD1 antibody can be determined, i.e., by repetitive cycles of Edman degradation, followed by amino acid analysis by HPLC. Other methods of amino acid sequencing are also known in the art. Once purified, the functionality of the anti-PD1 antibody can be assessed by any conventional method known in the art, e.g., ELISA.

Fusion Proteins

In certain aspects, provided herein are methods of treating cancer comprising administering to a subject having cancer an antibody, or functional fragment or functional variant thereof, that specifically binds programmed death protein 1 (PD1) e.g., described herein, in combination with a fusion protein that comprises a targeting moiety and an immunomodulatory moiety, wherein: i) said targeting moiety specifically binds epidermal growth factor receptor (EGFR); and (ii) said immunomodulatory moiety comprises an amino acid sequence of the extracellular domain of transforming growth factor-beta receptor II (TGFβRII).

EGFR Targeting Moieties

In some embodiments, the EGFR targeting moiety comprises an antibody, or a functional fragment or functional variant thereof. In some embodiments, the antibody is a full-length antibody, a single chain variable fragment (scFv), a scFv2, a scFv-Fc, a Fab, a Fab', a F(ab')2, a F(v), a single domain antibody, a single chain antibody, or a VHH. In some embodiments, the EGFR targeting moiety binds EGFR and inhibits downstream signaling through the bound EGF receptor.

In some embodiments, the anti-EGFR antibody is selected from the group consisting of cetuximab and panitumumab. In some embodiments, the anti-EGFR antibody is a functional fragment of cetuximab and panitumumab. In some embodiments, the anti-EGFR antibody is a functional variant of cetuximab and panitumumab.

Cetuximab

In some embodiments, the anti-EGFR antibody is cetuximab. In some embodiments, the anti-EGFR antibody cross-competes with cetuximab. In some embodiments, the anti-EGFR antibody binds to the same epitope as cetuximab. In some embodiments, the anti-EGFR antibody has the same CDRs as cetuximab.

In some embodiments the anti-EGFR antibody comprises a variable heavy chain (VH) that comprises three complementarity determining regions: VH CDR1, VH CDR2, and VH CDR3. In some embodiments, the anti-EGFR antibody comprises a VH comprising a VH CDR1 that comprises an amino acid sequence of SEQ ID NO: 34, with 0, 1, 2, or 3 amino acid modifications; a VH CDR2 that comprises an amino acid sequence of SEQ ID NO: 35, with 0, 1, 2, or 3 amino acid modifications; and a VH CDR3 that comprises an amino acid sequence of SEQ ID NO: 36, with 0, 1, 2, or 3 amino acid modifications. In some embodiments, the anti-EGFR antibody comprises a VH comprising a VH CDR1 that comprises the amino acid sequence of SEQ ID NO: 34, or the amino acid sequence of SEQ ID NO: 34 with 1, 2, or 3 amino acid modifications; a VH CDR2 that comprises the amino acid sequence of SEQ ID NO: 35, or the amino acid sequence of SEQ ID NO: 35 with 1, 2, or 3 amino acid modifications; and a VH CDR3 that comprises the amino acid sequence of SEQ ID NO: 36, or the amino acid sequence of SEQ ID NO: 35 with 1, 2, or 3 amino acid modifications.

In some embodiments the anti-EGFR antibody comprises a variable light chain (VL) that comprises three complementarity determining regions: VL CDR1, VL CDR2, and VL CDR3. In some embodiments, the anti-EGFR antibody comprises a VL comprising a VL CDR1 that comprises an amino acid sequence of SEQ ID NO: 37, with 0, 1, 2, or 3 amino acid modifications; a VL CDR2 that comprises an amino acid sequence of SEQ ID NO: 38, with 0, 1, 2, or 3 amino acid modifications; and a VL CDR3 that comprises an amino acid sequence of SEQ ID NO: 39, with 0, 1, 2, or 3 amino acid modifications. In some embodiments, the anti-EGFR antibody comprises a VL comprising a VL CDR1 that comprises the amino acid sequence of SEQ ID NO: 37, or the amino acid sequence of SEQ ID NO: 37 with 1, 2, or 3 amino acid modifications; a VL CDR2 that comprises the amino acid sequence of SEQ ID NO: 38, or the amino acid sequence of SEQ ID NO: 38 with 1, 2, or 3 amino acid modifications; and a VL CDR3 that comprises the amino acid sequence of SEQ ID NO: 39, or the amino acid sequence of SEQ ID NO: 39 with 1, 2, or 3 amino acid modifications.

In some embodiments, the anti-EGFR antibody comprises a VH comprising a VH CDR1 that comprises an amino acid sequence of SEQ ID NO: 34, with 0, 1, 2, or 3 amino acid modifications; a VH CDR2 that comprises an amino acid sequence of SEQ ID NO: 35, with 0, 1, 2, or 3 amino acid modifications; and a VH CDR3 that comprises an amino acid sequence of SEQ ID NO: 36, with 0, 1, 2, or 3 amino acid modifications; and a VL comprising a VL CDR1 that comprises an amino acid sequence of SEQ ID NO: 37, with 0, 1, 2, or 3 amino acid modifications; a VL CDR2 that comprises an amino acid sequence of SEQ ID NO: 38, with 0, 1, 2, or 3 amino acid modifications; and a VL CDR3 that comprises an amino acid sequence of SEQ ID NO: 39, with 0, 1, 2, or 3 amino acid modifications.

In some embodiments, the anti-EGFR antibody comprises a VH comprising a VH CDR1 that comprises the amino acid sequence of SEQ ID NO: 34, or the amino acid sequence of SEQ ID NO: 34 with 1, 2, or 3 amino acid modifications; a VH CDR2 that comprises the amino acid sequence of SEQ ID NO: 35, or the amino acid sequence of SEQ ID NO: 35 with 1, 2, or 3 amino acid modifications; and a VH CDR3 that comprises the amino acid sequence of SEQ ID NO: 36, or the amino acid sequence of SEQ ID NO: 36 with 1, 2, or 3 amino acid modifications; and a VL comprising a VL CDR1 that comprises the amino acid sequence of SEQ ID NO: 37, or the amino acid sequence of SEQ ID NO: 37 with 1, 2, or 3 amino acid modifications; a VL CDR2 that comprises the amino acid sequence of SEQ ID NO: 38, or the amino acid sequence of SEQ ID NO: 38 with 1, 2, or 3 amino acid modifications; and a VL CDR3 that comprises the amino acid sequence of SEQ ID NO: 39, or the amino acid sequence of SEQ ID NO: 39 with 1, 2, or 3 amino acid modifications.

In some embodiments, the anti-EGFR antibody comprises a VH comprising a VH CDR1 that comprises an amino acid sequence at least 95%, 96%, 97%, 98%, 99%, or 100% identical to the amino acid sequence of SEQ ID NO: 34; a VH CDR2 that comprises an amino acid sequence at least 95%, 96%, 97%, 98%, 99%, or 100% identical to the amino acid sequence of SEQ ID NO: 35; and a VH CDR3 that comprises an amino acid sequence at least 95%, 96%, 97%, 98%, 99%, or 100% identical to the amino acid sequence of SEQ ID NO: 36.

In some embodiments, the anti-EGFR antibody comprises a VL comprising a VL CDR1 that comprises an amino acid sequence at least 95%, 96%, 97%, 98%, 99%, or 100% identical to the amino acid sequence of SEQ ID NO: 37; a VL CDR2 that comprises an amino acid sequence at least 95%, 96%, 97%, 98%, 99%, or 100% identical to the amino acid sequence of SEQ ID NO: 38; and a VL CDR3 that comprises an amino acid sequence at least 95%, 96%, 97%, 98%, 99%, or 100% identical to the amino acid sequence of SEQ ID NO: 39.

In some embodiments, the anti-EGFR antibody comprises a VH comprising a VH CDR1 that comprises an amino acid sequence at least 95%, 96%, 97%, 98%, 99%, or 100% identical to the amino acid sequence of SEQ ID NO: 34; a VH CDR2 that comprises an amino acid sequence at least 95%, 96%, 97%, 98%, 99%, or 100% identical to the amino acid sequence of SEQ ID NO: 35; and a VH CDR3 that comprises an amino acid sequence at least 95%, 96%, 97%, 98%, 99%, or 100% identical to the amino acid sequence of SEQ ID NO: 36; and the anti-EGFR antibody comprises a VL comprising a VL CDR1 that comprises an amino acid sequence at least 95%, 96%, 97%, 98%, 99%, or 100% identical to the amino acid sequence of SEQ ID NO: 37; a VL CDR2 that comprises an amino acid sequence at least 95%, 96%, 97%, 98%, 99%, or 100% identical to the amino acid sequence of SEQ ID NO: 38; and a VL CDR3 that comprises an amino acid sequence at least 95%, 96%, 97%, 98%, 99%, or 100% identical to the amino acid sequence of SEQ ID NO: 39.

In some embodiments, the anti-EGFR antibody comprises a VH at least 90%, 91%, 92%, 93%, 94%, 95%, 96%, 97%, 98%, 99%, or 100% identical to the amino acid sequence of SEQ ID NO: 40. In some embodiments, the anti-EGFR antibody comprises a VL at least 90%, 91%, 92%, 93%, 94%, 95%, 96%, 97%, 98%, 99%, or 100% identical to the amino acid sequence of SEQ ID NO: 41. In some embodiments, the anti-EGFR antibody comprises a VH at least 90%, 91%, 92%, 93%, 94%, 95%, 96%, 97%, 98%, 99%, or 100% identical to the amino acid sequence of SEQ ID NO: 40; and a VL at least 90%, 91%, 92%, 93%, 94%, 95%, 96%, 97%, 98%, 99%, or 100% identical to the amino acid sequence of SEQ ID NO: 41.

In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 43. In some embodiments, the anti-EGFR antibody comprises a light chain that comprises an amino acid sequence at least 90%, 91%, 92%, 93%, 94%, 95%, 96%, 97%, 98%, 99%, or 100% identical to the amino acid sequence of SEQ ID NO: 44. In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 43; and a light chain that comprises an amino acid sequence at least 90%, 91%, 92%, 93%, 94%, 95%, 96%, 97%, 98%, 99%, or 100% identical to the amino acid sequence of SEQ ID NO: 44.

In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 42. In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 42; and a light chain that comprises an amino acid sequence at least 90%, 91%, 92%, 93%, 94%, 95%, 96%, 97%, 98%, 99%, or 100% identical to the amino acid sequence of SEQ ID NO: 44.

Panitumumab

In some embodiments, the anti-EGFR antibody is panitumumab. In some embodiments, the anti-EGFR antibody cross-competes with panitumumab. In some embodiments, the anti-EGFR antibody binds to the same epitope as panitumumab. In some embodiments, the anti-EGFR antibody has the same CDRs as panitumumab.

In some embodiments the anti-EGFR antibody comprises a variable heavy chain (VH) that comprises three complementarity determining regions: VH CDR1, VH CDR2, and VH CDR3. In some embodiments, the anti-EGFR antibody comprises a VH comprising a VH CDR1 that comprises an amino acid sequence of SEQ ID NO: 45, with 0, 1, 2, or 3 amino acid modifications; a VH CDR2 that comprises an amino acid sequence of SEQ ID NO: 46, with 0, 1, 2, or 3 amino acid modifications; and a VH CDR3 that comprises an amino acid sequence of SEQ ID NO: 47, with 0, 1, 2, or 3 amino acid modifications. In some embodiments, the anti-EGFR antibody comprises a VH comprising a VH CDR1 that comprises the amino acid sequence of SEQ ID NO: 45, or the amino acid sequence of SEQ ID NO: 45 with 1, 2, or 3 amino acid modifications; a VH CDR2 that comprises the amino acid sequence of SEQ ID NO: 46, or the amino acid sequence of SEQ ID NO: 46 with 1, 2, or 3 amino acid modifications; and a VH CDR3 that comprises the amino acid sequence of SEQ ID NO: 47, or the amino acid sequence of SEQ ID NO: 47 with 1, 2, or 3 amino acid modifications.

In some embodiments the anti-EGFR antibody comprises a variable light chain (VL) that comprises three complementarity determining regions: VL CDR1, VL CDR2, and VL CDR3. In some embodiments, the anti-EGFR antibody comprises a VL comprising a VL CDR1 that comprises an amino acid sequence of SEQ ID NO: 48, with 0, 1, 2, or 3 amino acid modifications; a VL CDR2 that comprises an amino acid sequence of SEQ ID NO: 49, with 0, 1, 2, or 3 amino acid modifications; and a VL CDR3 that comprises an amino acid sequence of SEQ ID NO: 50, with 0, 1, 2, or 3 amino acid modifications. In some embodiments, the anti-EGFR antibody comprises a VL comprising a VL CDR1 that comprises the amino acid sequence of SEQ ID NO: 48, or the amino acid sequence of SEQ ID NO: 48 with 1, 2, or 3 amino acid modifications; a VL CDR2 that comprises the amino acid sequence of SEQ ID NO: 49, or the amino acid sequence of SEQ ID NO: 49 with 1, 2, or 3 amino acid modifications; and a VL CDR3 that comprises the amino acid sequence of SEQ ID NO: 50, or the amino acid sequence of SEQ ID NO: 50 with 1, 2, or 3 amino acid modifications.

In some embodiments, the anti-EGFR antibody comprises a VH comprising a VH CDR1 that comprises an amino acid sequence of SEQ ID NO: 45, with 0, 1, 2, or 3 amino acid modifications; a VH CDR2 that comprises an amino acid sequence of SEQ ID NO: 46, with 0, 1, 2, or 3 amino acid modifications; and a VH CDR3 that comprises an amino acid sequence of SEQ ID NO: 47, with 0, 1, 2, or 3 amino acid modifications; and a VL comprising a VL CDR1 that comprises an amino acid sequence of SEQ ID NO: 48, with 0, 1, 2, or 3 amino acid modifications; a VL CDR2 that comprises an amino acid sequence of SEQ ID NO: 49, with 0, 1, 2, or 3 amino acid modifications; and a VL CDR3 that comprises an amino acid sequence of SEQ ID NO: 50, with 0, 1, 2, or 3 amino acid modifications.

In some embodiments, the anti-EGFR antibody comprises a VH comprising a VH CDR1 that comprises the amino acid sequence of SEQ ID NO: 45, or the amino acid sequence of SEQ ID NO: 45 with 1, 2, or 3 amino acid modifications; a VH CDR2 that comprises the amino acid sequence of SEQ ID NO: 46, or the amino acid sequence of SEQ ID NO: 46 with 1, 2, or 3 amino acid modifications; and a VH CDR3 that comprises the amino acid sequence of SEQ ID NO: 47, or the amino acid sequence of SEQ ID NO: 47 with 1, 2, or 3 amino acid modifications; and a VL comprising a VL CDR1 that comprises the amino acid sequence of SEQ ID NO: 48, or the amino acid sequence of SEQ ID NO: 48 with 1, 2, or 3 amino acid modifications; a VL CDR2 that comprises the amino acid sequence of SEQ ID NO: 49, or the amino acid sequence of SEQ ID NO: 49 with 1, 2, or 3 amino acid modifications; and a VL CDR3 that comprises an amino acid sequence of SEQ ID NO: 50, or the amino acid sequence of SEQ ID NO: 50 with 1, 2, or 3 amino acid modifications.

In some embodiments, the anti-EGFR antibody comprises a VH comprising a VH CDR1 that comprises an amino acid sequence at least 95%, 96%, 97%, 98%, 99%, or 100% identical to the amino acid sequence of SEQ ID NO: 45; a VH CDR2 that comprises an amino acid sequence at least 95%, 96%, 97%, 98%, 99%, or 100% identical to the amino acid sequence of SEQ ID NO: 46; and a VH CDR3 that comprises an amino acid sequence at least 95%, 96%, 97%, 98%, 99%, or 100% identical to the amino acid sequence of SEQ ID NO: 47.

In some embodiments, the anti-EGFR antibody comprises a VL comprising a VL CDR1 that comprises an amino acid sequence at least 95%, 96%, 97%, 98%, 99%, or 100% identical to the amino acid sequence of SEQ ID NO: 48; a VL CDR2 that comprises an amino acid sequence at least 95%, 96%, 97%, 98%, 99%, or 100% identical to the amino acid sequence of SEQ ID NO: 49; and a VL CDR3 that comprises an amino acid sequence at least 95%, 96%, 97%, 98%, 99%, or 100% identical to the amino acid sequence of SEQ ID NO: 50.

In some embodiments, the anti-EGFR antibody comprises a VH comprising a VH CDR1 that comprises an amino acid sequence at least 95%, 96%, 97%, 98%, 99%, or 100% identical to the amino acid sequence of SEQ ID NO: 45; a VH CDR2 that comprises an amino acid sequence at least 95%, 96%, 97%, 98%, 99%, or 100% identical to the amino acid sequence of SEQ ID NO: 46; and a VH CDR3 that comprises an amino acid sequence at least 95%, 96%, 97%, 98%, 99%, or 100% identical to the amino acid sequence of SEQ ID NO: 47; and the anti-EGFR antibody comprises a VL comprising a VL CDR1 that comprises an amino acid sequence at least 95%, 96%, 97%, 98%, 99%, or 100% identical to the amino acid sequence of SEQ ID NO: 48; a VL CDR2 that comprises an amino acid sequence at least 95%, 96%, 97%, 98%, 99%, or 100% identical to the amino acid sequence of SEQ ID NO: 49; and a VL CDR3 that comprises an amino acid sequence at least 95%, 96%, 97%, 98%, 99%, or 100% identical to the amino acid sequence of SEQ ID NO: 50.

In some embodiments, the anti-EGFR antibody comprises a VH at least 90%, 91%, 92%, 93%, 94%, 95%, 96%, 97%, 98%, 99%, or 100% identical to the amino acid sequence of SEQ ID NO: 51. In some embodiments, the anti-EGFR antibody comprises a VL at least 90%, 91%, 92%, 93%, 94%, 95%, 96%, 97%, 98%, 99%, or 100% identical to the amino acid sequence of SEQ ID NO: 52. In some embodiments, the anti-EGFR antibody comprises a VH at least 90%, 91%, 92%, 93%, 94%, 95%, 96%, 97%, 98%, 99%, or 100% identical to the amino acid sequence of SEQ ID NO: 51; and a VL at least 90%, 91%, 92%, 93%, 94%, 95%, 96%, 97%, 98%, 99%, or 100% identical to the amino acid sequence of SEQ ID NO: 52.

In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 54. In some embodiments, the anti-EGFR antibody comprises a light chain that comprises an amino acid sequence at least 90%, 91%, 92%, 93%, 94%, 95%, 96%, 97%, 98%, 99%, or 100% identical to the amino acid sequence of SEQ ID NO: 55. In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 54; and a light chain that comprises an amino acid sequence at least 90%, 91%, 92%, 93%, 94%, 95%, 96%, 97%, 98%, 99%, or 100% identical to the amino acid sequence of SEQ ID NO: 55.

In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 53. In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of SEQ ID NO: 53; and a light chain that comprises an amino acid sequence at least 90%, 91%, 92%, 93%, 94%, 95%, 96%, 97%, 98%, 99%, or 100% identical to the amino acid sequence of SEQ ID NO: 55.

In some embodiments, the anti-EGFR antibody comprises an antibody in Table 2. In some embodiments, the anti-EGFR antibody is an antibody in Table 2.

In some embodiments, the anti-EGFR antibody comprises a VH comprising a VH CDR1 that comprises an amino acid sequence at least 95%, 96%, 97%, 98%, 99%, or 100% identical to the amino acid sequence of a VH CDR1 in Table 2; a VH CDR2 that comprises an amino acid sequence at least 95%, 96%, 97%, 98%, 99%, or 100% identical to the amino acid sequence of a VH CDR2 in Table 2; and a VH CDR3 that comprises an amino acid sequence at least 95%, 96%, 97%, 98%, 99%, or 100% identical to the amino acid sequence of a VH CDR3 in Table 2.

In some embodiments, the anti-EGFR antibody comprises a VL comprising a VL CDR1 that comprises an amino acid sequence at least 95%, 96%, 97%, 98%, 99%, or 100% identical to the amino acid sequence of a VL CDR1 in Table 2; a VL CDR2 that comprises an amino acid sequence at least 95%, 96%, 97%, 98%, 99%, or 100% identical to the amino acid sequence of a VL CDR2 in Table 2; and a VL CDR3 that comprises an amino acid sequence at least 95%, 96%, 97%, 98%, 99%, or 100% identical to the amino acid sequence of a VL CDR3 in Table 2.

In some embodiments, the anti-EGFR antibody comprises a VH comprising a VH CDR1 that comprises an amino acid sequence at least 95%, 96%, 97%, 98%, 99%, or 100% identical to the amino acid sequence of a VH CDR1 in Table 2; a VH CDR2 that comprises an amino acid sequence at least 95%, 96%, 97%, 98%, 99%, or 100% identical to the amino acid sequence of a VH CDR2 in Table 2; a VH CDR3 that comprises an amino acid sequence at least 95%, 96%, 97%, 98%, 99%, or 100% identical to the amino acid sequence of a VH CDR3 in Table 2; a VL comprising a VL CDR1 that comprises an amino acid sequence at least 95%, 96%, 97%, 98%, 99%, or 100% identical to the amino acid sequence of a VL CDR1 in Table 2; a VL CDR2 that comprises an amino acid sequence at least 95%, 96%, 97%, 98%, 99%, or 100% identical to the amino acid sequence of a VL CDR2 in Table 2; and a VL CDR3 that comprises an amino acid sequence at least 95%, 96%, 97%, 98%, 99%, or 100% identical to the amino acid sequence of a VL CDR3 in Table 2.

In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of a heavy chain in Table 2. In some embodiments, the anti-EGFR antibody comprises a light chain that comprises an amino acid sequence at least 90%, 91%, 92%, 93%, 94%, 95%, 96%, 97%, 98%, 99%, or 100% identical to the amino acid sequence of a light chain in Table 2. In some embodiments, the anti-EGFR antibody comprises a heavy chain that comprises an amino acid sequence at least 90%, 91%, 92%, 93%, 94%, 95%, 96%, 97%, 98%, 99%, or 100% identical to the amino acid sequence of a heavy chain in Table 2; and a light chain that comprises an amino acid sequence at least 90%, 91%, 92%, 93%, 94%, 95%, 96%, 97%, 98%, 99%, or 100% identical to the amino acid sequence of a light chain in Table 2.

In some embodiments, the anti-EGFR antibody comprises a VH that comprises an amino acid sequence at least 95%, 96%, 97%, 98%, 99%, or 100% identical to the amino acid sequence of a VH of an antibody in Table 2. In some embodiments, the anti-EGFR antibody comprises a VL that comprises an amino acid sequence at least 95%, 96%, 97%, 98%, 99%, or 100% identical to the amino acid sequence of an antibody in Table 2. In some embodiments, the anti-EGFR antibody comprises a VH that comprises an amino acid sequence at least 95%, 96%, 97%, 98%, 99%, or 100% identical to the amino acid sequence of a VH of an antibody in Table 2; and a VL that comprises an amino acid sequence at least 95%, 96%, 97%, 98%, 99%, or 100% identical to the amino acid sequence of an antibody in Table 2.

TABLE 2

Exemplary Anti-EGFR Antibodies

| Antibody | Region | Amino Acid Sequence | SEQ ID NO |
|---|---|---|---|
| Cetuximab (CDRs defined according to Kabat) | VH CDR1 | NYGVH | 34 |
| | VH CDR2 | VIWSGGNTDYNTPFTS | 35 |
| | VH CDR3 | ALTYYDYEFAY | 36 |
| | VL CDR1 | RASQSIGTNIH | 37 |
| | VL CDR2 | YASESIS | 38 |
| | VL CDR3 | QQNNNWPTT | 39 |
| | VH | QVQLKQSGPGLVQPSQSLSITCTVSGFSLT**NYGVH**WVRQSP<br>GKGLEWLG**VIWSGGNTDYNTPFTS**RLSINKDNSKSQVFFKM<br>NSLQSNDTAIYYCAR**ALTYYDYEFAY**WGQGTLVTVSA | 40 |
| | VL | DILLTQSPVILSVSPGERVSFSC**RASQSIGTNIH**WYQQRTN<br>GSPRLLIK**YASESIS**GIPSRFSGSGSGTDFTLSINSVESED<br>IADYYC**QQNNNWPTT**FGAGTKLELK | 41 |
| | HC-A<br>VH<br>Underlined<br>CDRs<br>Underlined<br>& Bold | QVQLKQSGPGLVQPSQSLSITCTVSGFSLT**NYGVH**WVRQSP<br>GKGLEWLG**VIWSGGNTDYNTPFTS**RLSINKDNSKSQVFFKM<br>NSLQSNDTAIYYCAR**ALTYYDYEFAY**WGQGTLVTVSAASTK<br>GPSVFPLAPSSKSTSGGTAALGCLVKDYFPEPVTVSWNSGA<br>LTSGVHTFPAVLQSSGLYSLSSVVTVPSSSLGTQTYICNVN<br>HKPSNTKVDKRVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSNK<br>ALPAPIEKTISKAKGQPREPQVYTLPPSRDELTKNQVSLTC<br>LVKGFYPSDIAVEWESNGQPENNYKTTPPVLDSDGSFFLYS<br>KLTVDKSRWQQGNVFSCSVMHEALHNHYTQKSLSLSPGK | 42 |
| | HC-B-<br>Modified<br>Cetuximab<br>(No C-terminal<br>Lysine)<br>VH<br>Underlined<br>CDRs<br>Underlined<br>& Bold | QVQLKQSGPGLVQPSQSLSITCTVSGFSLT**NYGVH**WVRQSP<br>GKGLEWLG**VIWSGGNTDYNTPFTS**RLSINKDNSKSQVFFKM<br>NSLQSNDTAIYYCAR**ALTYYDYEFAY**WGQGTLVTVSAASTK<br>GPSVFPLAPSSKSTSGGTAALGCLVKDYFPEPVTVSWNSGA<br>LTSGVHTFPAVLQSSGLYSLSSVVTVPSSSLGTQTYICNVN<br>HKPSNTKVDKRVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSNK<br>ALPAPIEKTISKAKGQPREPQVYTLPPSRDELTKNQVSLTC<br>LVKGFYPSDIAVEWESNGQPENNYKTTPPVLDSDGSFFLYS<br>KLTVDKSRWQQGNVFSCSVMHEALHNHYTQKSLSLSPG | 43 |
| | LC<br>VL<br>Underlined<br>CDRs<br>Underlined<br>& Bold | DILLTQSPVILSVSPGERVSFSC**RASQSIGTNIH**WYQQRTN<br>GSPRLLIK**YASESIS**GIPSRFSGSGSGTDFTLSINSVESED<br>IADYYC**QQNNNWPTT**FGAGTKLELKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPV<br>TKSENRGEC | 44 |
| Panitumumab (CDRs defined according to Kabat) | VH CDR1 | SGDYYWT | 45 |
| | VH CDR2 | HIYYSGNTNYNPSLKS | 46 |
| | VH CDR3 | DRVTGAFDI | 47 |

TABLE 2-continued

| Exemplary Anti-EGFR Antibodies | | | |
|---|---|---|---|
| Antibody | Region | Amino Acid Sequence | SEQ ID NO |
| | VL CDR1 | QASQDISNYLN | 48 |
| | VL CDR2 | DASNLET | 49 |
| | VL CDR3 | QHFDHLPLA | 50 |
| | VH | QVQLQESGPGLVKPSETLSLTCTVSGGSVS**SGDYYWT**WIRQ<br>SPGKGLEWIG**HIYYSGNTNYNPSLKS**RLTISIDTSKTQFSL<br>KLSSVTAADTAIYYCVR**DRVTGAFDI**WGQGTMVTVSS | 51 |
| | VL | DIQMTQSPSSLSASVGDRVTITC**QASQDISNYLN**WYQQKPG<br>KAPKLLIY**DASNLET**GVPSRFSGSGSGTDFTFTISSLQPED<br>IATYFC**QHFDHLPLA**FGGGTKVEIK | 52 |
| | HC-A<br>VH<br>Underlined<br>CDRs<br>Underlined<br>& Bold | QVQLQESGPGLVKPSETLSLTCTVSGGSVS**SGDYYWT**WIRQ<br>SPGKGLEWIG**HIYYSGNTNYNPSLKS**RLTISIDTSKTQFSL<br>KLSSVTAADTAIYYCVR**DRVTGAFDI**WGQGTMVTVSSASTK<br>GPSVFPLAPCSRSTSESTAALGCLVKDYFPEPVTVSWNSGA<br>LTSGVHTFPAVLQSSGLYSLSSVVTVPSSNFGTQTYTCNVD<br>HKPSNTKVDKTVERKCCVECPPCPAPPVAGPSVFLFPPKPK<br>DTLMISRTPEVTCVVVDVSHEDPEVQFNWYVDGVEVHNAKT<br>KPREEQFNSTFRVVSVLTVVHQDWLNGKEYKCKVSNKGLPA<br>PIEKTISKTKGQPREPQVYTLPPSREEMTKNQVSLTCLVKG<br>FYPSDIAVEWESNGQPENNYKTTPPMLDSDGSFFLYSKLTV<br>DKSRWQQGNVFSCSVMHEALHNHYTQKSLSLSPGK | 53 |
| | HC-B-<br>Modified<br>Panitumumab<br>(No C-terminal<br>Lysine)<br>VH<br>Underlined<br>CDRs<br>Underlined<br>& Bold | QVQLQESGPGLVKPSETLSLTCTVSGGSVS**SGDYYWT**WIRQ<br>SPGKGLEWIG**HIYYSGNTNYNPSLKS**RLTISIDTSKTQFSL<br>KLSSVTAADTAIYYCVR**DRVTGAFDI**WGQGTMVTVSSASTK<br>GPSVFPLAPCSRSTSESTAALGCLVKDYFPEPVTVSWNSGA<br>LTSGVHTFPAVLQSSGLYSLSSVVTVPSSNFGTQTYTCNVD<br>HKPSNTKVDKTVERKCCVECPPCPAPPVAGPSVFLFPPKPK<br>DTLMISRTPEVTCVVVDVSHEDPEVQFNWYVDGVEVHNAKT<br>KPREEQFNSTFRVVSVLTVVHQDWLNGKEYKCKVSNKGLPA<br>PIEKTISKTKGQPREPQVYTLPPSREEMTKNQVSLTCLVKG<br>FYPSDIAVEWESNGQPENNYKTTPPMLDSDGSFFLYSKLTV<br>DKSRWQQGNVFSCSVMHEALHNHYTQKSLSLSPG | 54 |
| | LC<br>VL<br>Underlined<br>CDRs<br>Underlined<br>& Bold | DIQMTQSPSSLSASVGDRVTITC**QASQDISNYLN**WYQQKPG<br>KAPKLLIY**DASNLET**GVPSRFSGSGSGTDFTFTISSLQPED<br>IATYFC**QHFDHLPLA**FGGGTKVEIKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPV<br>TKSENRGEC | 55 |

TGFβ TRAP

In certain aspects, provided herein are methods of treating cancer comprising administering to a subject having cancer an antibody, or functional fragment or functional variant thereof, that specifically binds programmed death protein 1 (PD1) e.g., described herein, in combination with a fusion protein that comprises a targeting moiety and an immunomodulatory moiety, wherein: i) said targeting moiety specifically binds epidermal growth factor receptor (EGFR); and (ii) said immunomodulatory moiety comprises an amino acid sequence of the extracellular domain (ECD) of transforming growth factor-beta receptor II (TGFβRII).

In some embodiments, the TGFβRII ECD binds to at least one TGFβ isoform. In some embodiments, the TGFβRII ECD binds to TGFβ1. In some embodiments, the TGFβRII ECD binds to TGFβ3. In some embodiments, the TGFβRII ECD does not bind to TGFβ2.

In some embodiments, the TGFβRII ECD comprises sufficient sequence of a naturally occurring TGFβRII ECD to enable the protein to bind TGFβ. In some embodiments, the TGFβRII ECD comprises sufficient sequence of a naturally occurring TGFβRII ECD to enable the protein to bind TGFβ1. In some embodiments, the TGFβRII ECD comprises sufficient sequence of a naturally occurring TGFβRII ECD to enable the protein to bind TGFβ3.

In some embodiments, the extracellular domain of TGFβRII comprises a truncated portion of SEQ ID NO: 56, that is capable of binding TGFβ. The extracellular domain of TGFβRII may be truncated on the N-terminus, the C-terminus, or both the N and C terminus. The truncation may comprise the deletion of 1-10 amino acids. The truncation may comprise the deletion of 1, 2, 3, 4, 5, 6, 7, 8, 9, or 10 amino acids. The truncation may comprise the deletion of 1, 2, 3, 4, 5 amino acids from the N terminus, the C terminus, or both the N and C terminus.

In some embodiments, the extracellular domain of TGFβRII comprises an amino acid sequence at least 90%, 91%, 92%, 93%, 94%, 95%, 96%, 97%, 98%, 99%, or 100% identical to the amino acid sequence of SEQ ID NO: 56. In some embodiments, the extracellular domain of TGFβRII consists essentially of an amino acid sequence at least 90%, 91%, 92%, 93%, 94%, 95%, 96%, 97%, 98%, 99%, or 100% identical to the amino acid sequence of SEQ ID NO: 56. In some embodiments, the extracellular domain of TGFβRII consists of an amino acid sequence at least 90%, 91%, 92%, 93%, 94%, 95%, 96%, 97%, 98%, 99%, or 100% identical to the amino acid sequence of SEQ ID NO: 56.

TABLE 3

| Exemplary TGFβRII ECD | | |
|---|---|---|
| | Amino Acid Sequence | SEQ ID NO |
| TGFβRII ECD | TIPPHVQKSVNNDMIVTDNNGA VKFPQLCKFCDVRFSTCDNQKS CMSNCSITSICEKPQEVCVAVW RKNDENITLETVCHDPKLPYHD FILEDAASPKCIMKEKKKPGET FFMCSCSSDECNDNIIFSEEYN TSNPD | 56 |

Orientation

In some embodiments, the immunomodulatory moiety is operably connected to the C terminus of the targeting moiety. In some embodiments, the immunomodulatory moiety is operably connected to the N terminus of the targeting moiety.

In some embodiments, the targeting moiety is an antibody (or functional fragment or variant thereof) that comprises 1) a VH or a heavy chain, and 2) a VL or a light chain. In some embodiments, the immunomodulatory moiety is operably connected to the C terminus of the VH or heavy chain. In some embodiments, the immunomodulatory moiety is operably connected to the C terminus of the VL or light chain. In some embodiments, the immunomodulatory moiety is operably connected to the C terminus of the constant region of the heavy chain. In some embodiments, the immunomodulatory moiety is operably connected to the C terminus of the constant region of the light chain. In some embodiments, the immunomodulatory moiety is operably connected to the N terminus of the VH or heavy chain. In some embodiments, the immunomodulatory moiety is operably connected to the N terminus of the VL or light chain.

Linkers

In some embodiments, the targeting moiety and an immunomodulatory moiety of the fusion protein are directly operably connected. In some embodiments, the targeting moiety and an immunomodulatory moiety of the fusion protein are indirectly operably connected. In some embodiments, the targeting moiety and an immunomodulatory moiety of the fusion protein are indirectly operably connected via a linker. In some embodiments, the linker is a peptide linker.

Any suitable peptide linker known in the art can be used that enables the immunomodulatory moiety and the targeting moiety to bind their respective antigens. Exemplary peptide linkers comprising glycine and serine amino acids are provided in Table 4.

In some embodiments, the linker comprises an amino acid sequence at least 95%, 96%, 97%, 98%, 99%, or 100% identical to the amino acid sequence of any one of SEQ ID NOS: 57-61. In some embodiments, the linker comprises the amino acid sequence of any one of SEQ ID NOS: 57-61, or the amino acid sequence of any one of SEQ ID NOS: 57-61 with 1, 2, or 3 amino acid modifications.

In some embodiments, the linker comprises an amino acid sequence at least 95%, 96%, 97%, 98%, 99%, or 100% identical to the amino acid sequence of SEQ ID NO: 57. In some embodiments, the linker comprises an amino acid sequence 100% identical to the amino acid sequence of SEQ ID NO: 57. In some embodiments, the linker comprises the amino acid sequence of SEQ ID NO: 57, or the amino acid sequence of SEQ ID NO: 57 with 1, 2, or 3 amino acid modifications. In some embodiments, the linker consists essentially of an amino acid sequence 100% identical to the amino acid sequence of SEQ ID NO: 57. In some embodiments, the linker consists of an amino acid sequence 100% identical to the amino acid sequence of SEQ ID NO: 57. In some embodiments, the linker consists of the amino acid sequence of SEQ ID NO: 57, or the amino acid sequence of SEQ ID NO: 57 with 1, 2, or 3 amino acid modifications.

In some embodiments, the linker comprises an amino acid sequence at least 95%, 96%, 97%, 98%, 99%, or 100% identical to the amino acid sequence of SEQ ID NO: 58. In some embodiments, the linker comprises an amino acid sequence 100% identical to the amino acid sequence of SEQ ID NO: 58. In some embodiments, the linker comprises the amino acid sequence of SEQ ID NO: 58, or the amino acid sequence of SEQ ID NO: 28 with 1, 2, or 3 amino acid modifications. In some embodiments, the linker consists essentially of an amino acid sequence 100% identical to the amino acid sequence of SEQ ID NO: 58. In some embodiments, the linker consists of an amino acid sequence 100% identical to the amino acid sequence of SEQ ID NO: 58. In some embodiments, the linker consists of the amino acid sequence of SEQ ID NO: 58, or the amino acid sequence of SEQ ID NO: 58 with 1, 2, or 3 amino acid modifications.

In some embodiments, the linker comprises an amino acid sequence at least 95%, 96%, 97%, 98%, 99%, or 100% identical to the amino acid sequence of SEQ ID NO: 59. In some embodiments, the linker comprises an amino acid sequence 100% identical to the amino acid sequence of SEQ ID NO: 59. In some embodiments, the linker comprises the amino acid sequence of SEQ ID NO: 59, or the amino acid sequence of SEQ ID NO: 59 with 1, 2, or 3 amino acid modifications. In some embodiments, the linker consists essentially of an amino acid sequence 100% identical to the amino acid sequence of SEQ ID NO: 59. In some embodiments, the linker consists of an amino acid sequence 100% identical to the amino acid sequence of SEQ ID NO: 59. In some embodiments, the linker consists of the amino acid sequence of SEQ ID NO: 59, or the amino acid sequence of SEQ ID NO: 59 with 1, 2, or 3 amino acid modifications.

In some embodiments, the linker comprises an amino acid sequence at least 95%, 96%, 97%, 98%, 99%, or 100% identical to the amino acid sequence of SEQ ID NO: 60. In some embodiments, the linker comprises an amino acid sequence 100% identical to the amino acid sequence of SEQ ID NO: 60. In some embodiments, the linker comprises the amino acid sequence of SEQ ID NO: 60, or the amino acid sequence of SEQ ID NO: 60 with 1, 2, or 3 amino acid modifications. In some embodiments, the linker consists essentially of an amino acid sequence 100% identical to the amino acid sequence of SEQ ID NO: 60. In some embodiments, the linker consists of an amino acid sequence 100% identical to the amino acid sequence of SEQ ID NO: 60. In some embodiments, the linker consists of the amino acid sequence of SEQ ID NO: 60, or the amino acid sequence of SEQ ID NO: 60 with 1, 2, or 3 amino acid modifications.

In some embodiments, the linker comprises an amino acid sequence at least 95%, 96%, 97%, 98%, 99%, or 100% identical to the amino acid sequence of SEQ ID NO: 61. In some embodiments, the linker comprises an amino acid sequence 100% identical to the amino acid sequence of SEQ ID NO: 61. In some embodiments, the linker comprises the amino acid sequence of SEQ ID NO: 61, or the amino acid sequence of SEQ ID NO: 61 with 1, 2, or 3 amino acid modifications. In some embodiments, the linker consists essentially of an amino acid sequence 100% identical to the amino acid sequence of SEQ ID NO: 61. In some embodiments, the linker consists of an amino acid sequence 100% identical to the amino acid sequence of SEQ ID NO: 61. In some embodiments, the linker consists of the amino acid sequence of SEQ ID NO: 61, or the amino acid sequence of SEQ ID NO: 61 with 1, 2, or 3 amino acid modifications.

TABLE 4

Exemplary Linkers

| Linker | Amino Acid Sequence | SEQ ID NO |
|---|---|---|
| $(GGGS)_3$ | GGGGSGGGGSGGGGS | 57 |
| $(GGGS)_4$ | GGGGSGGGGSGGGGSGGGS | 58 |
| $(GGGS)_5$ | GGGGSGGGGSGGGGSGGGSGGGS | 59 |
| $(GGGS)_2$ | GGGGSGGGGS | 60 |
| $(GGGS)_1$ | GGGGS | 61 |

Exemplary Fusion Proteins

Exemplary fusion proteins of the present disclosure are provided in Table 5. In one embodiment, the fusion protein comprises BCA101. BCA101, is a bifunctional fusion protein that comprises an anti-EGFR antibody and the extracellular domain of TGFβRII fused to the C-terminus of the anti-EGFR antibody light chain.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 43. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 62. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 43; and a light chain that comprises an amino acid sequence at least 90%, 91%, 92%, 93%, 94%, 95%, 96%, 97%, 98%, 99%, or 100% identical to the amino acid sequence of SEQ ID NO: 62.

In some embodiments, the fusion protein comprises a heavy chain that comprises an amino acid sequence 100% identical to the amino acid sequence of SEQ ID NO: 43. In some embodiments, the fusion protein comprises a light chain that comprises an amino acid sequence 100% identical to the amino acid sequence of SEQ ID NO: 62. In some embodiments, the fusion protein comprises a heavy chain that comprises an amino acid sequence 100% identical to the amino acid sequence of SEQ ID NO: 43; and a light chain that comprises an amino acid sequence 100% identical to the amino acid sequence of SEQ ID NO: 62.

In some embodiments, the fusion protein comprises a heavy chain, wherein the amino acid sequence of the heavy chain comprises the amino acid sequence of SEQ ID NO: 43. In some embodiments, the fusion protein comprises a light chain, wherein the amino acid sequence of the light chain comprises the amino acid sequence of SEQ ID NO: 62. In some embodiments, the fusion protein comprises a heavy chain, wherein the amino acid sequence of the heavy chain comprises the amino acid sequence of SEQ ID NO: 43; and a light chain, wherein the amino acid sequence of the light chain comprises the amino acid sequence of SEQ ID NO: 62.

In some embodiments, the fusion protein comprises a heavy chain that comprises the amino acid sequence of SEQ ID NO: 43, with 1, 2, or 3 amino acid modifications. In some embodiments, the fusion protein comprises a light chain that comprises the amino acid sequence of SEQ ID NO: 62 with 1, 2, or 3 amino acid modifications. In some embodiments, the fusion protein comprises a heavy chain that comprises the amino acid sequence of SEQ ID NO: 43, with 1, 2, or 3 amino acid modifications; and a light chain that comprises the amino acid sequence of SEQ ID NO: 62 with 1, 2, or 3 amino acid modifications.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 43. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 62. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 43; and a light chain that consists of an amino acid sequence at least 90%, 91%, 92%, 93%, 94%, 95%, 96%, 97%, 98%, 99%, or 100% identical to the amino acid sequence of SEQ ID NO: 62.

In some embodiments, the fusion protein comprises a heavy chain that consists of an amino acid sequence 100% identical to the amino acid sequence of SEQ ID NO: 43. In some embodiments, the fusion protein comprises a light chain that consists of an amino acid sequence 100% identical to the amino acid sequence of SEQ ID NO: 62. In some embodiments, the fusion protein comprises a heavy chain that consists of an amino acid sequence 100% identical to the amino acid sequence of SEQ ID NO: 43; and a light chain that comprises an amino acid sequence 100% identical to the amino acid sequence of SEQ ID NO: 62.

In some embodiments, the fusion protein comprises a heavy chain that consists of the amino acid sequence of SEQ ID NO: 43, with 1, 2, or 3 amino acid modifications. In some embodiments, the fusion protein comprises a light chain that consists of the amino acid sequence of SEQ ID NO: 62, with 1, 2, or 3 amino acid modifications. In some embodiments, the fusion protein comprises a heavy chain that consists of the amino acid sequence of SEQ ID NO: 43, with 1, 2, or 3 amino acid modifications; and a light chain that consists of the amino acid sequence of SEQ ID NO: 62, with 1, 2, or 3 amino acid modifications.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 63. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 44. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 63; and a light chain that comprises an amino acid sequence at least 90%, 91%, 92%, 93%, 94%, 95%, 96%, 97%, 98%, 99%, or 100% identical to the amino acid sequence of SEQ ID NO: 44.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 63. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 44. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 63; and a light chain that consists of an amino acid sequence at least 90%, 91%, 92%, 93%, 94%, 95%, 96%, 97%, 98%, 99%, or 100% identical to the amino acid sequence of SEQ ID NO: 44.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 42. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 62. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 42; and a light chain that comprises an amino acid sequence at least 90%, 91%, 92%, 93%, 94%, 95%, 96%, 97%, 98%, 99%, or 100% identical to the amino acid sequence of SEQ ID NO: 62.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 42. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 62. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO:42; and a light chain that consists of an amino acid sequence at least 90%, 91%, 92%, 93%, 94%, 95%, 96%, 97%, 98%, 99%, or 100% identical to the amino acid sequence of SEQ ID NO: 62.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 64. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 44. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 64; and a light chain that comprises an amino acid sequence at least 90%, 91%, 92%, 93%, 94%, 95%, 96%, 97%, 98%, 99%, or 100% identical to the amino acid sequence of SEQ ID NO: 44.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 64. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 44. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 64; and a light chain that consists of an amino acid sequence at least 90%, 91%, 92%, 93%, 94%, 95%, 96%, 97%, 98%, 99%, or 100% identical to the amino acid sequence of SEQ ID NO: 44.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 53. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 65. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 53; and a light chain that comprises an amino acid sequence at least 90%, 91%, 92%, 93%, 94%, 95%, 96%, 97%, 98%, 99%, or 100% identical to the amino acid sequence of SEQ ID NO: 65.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 53. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 65. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 53; and a light chain that consists of an amino acid sequence at least 90%, 91%, 92%, 93%, 94%, 95%, 96%, 97%, 98%, 99%, or 100% identical to the amino acid sequence of SEQ ID NO: 65.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 66. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 55. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 66; and a light chain that comprises an amino acid sequence at least 90%, 91%, 92%, 93%, 94%, 95%, 96%, 97%, 98%, 99%, or 100% identical to the amino acid sequence of SEQ ID NO: 55.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 66. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 55. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 66; and a light chain that consists of an amino acid sequence at least 90%, 91%, 92%, 93%, 94%, 95%, 96%, 97%, 98%, 99%, or 100% identical to the amino acid sequence of SEQ ID NO: 55.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 54. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 65. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 54; and a light chain that comprises an amino acid sequence at least 90%, 91%, 92%, 93%, 94%, 95%, 96%, 97%, 98%, 99%, or 100% identical to the amino acid sequence of SEQ ID NO: 65.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 54. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 65. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 54; and a light chain that consists of an amino acid sequence at least 90%, 91%, 92%, 93%, 94%, 95%, 96%, 97%, 98%, 99%, or 100% identical to the amino acid sequence of SEQ ID NO: 65.

In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 67. In some embodiments, the fusion protein comprises a light chain that comprises an amino acid sequence at least 90%, 91%, 92%, 93%, 94%, 95%, 96%, 97%, 98%, 99%, or 100% identical to the amino acid sequence of SEQ ID NO: 55. In some embodiments, the fusion protein comprises a heavy chain that comprises an amino acid sequence at least 90%, 91%, 92%, 93%, 94%, 95%, 96%, 97%, 98%, 99%, or 100% identical to the amino acid sequence of SEQ ID NO: 67; and a light chain that comprises an amino acid sequence at least 90%, 91%, 92%, 93%, 94%, 95%, 96%, 97%, 98%, 99%, or 100% identical to the amino acid sequence of SEQ ID NO: 55.

In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 67. In some embodiments, the fusion protein comprises a light chain that consists of an amino acid sequence at least 90%, 91%, 92%, 93%, 94%, 95%, 96%, 97%, 98%, 99%, or 100% identical to the amino acid sequence of SEQ ID NO: 55. In some embodiments, the fusion protein comprises a heavy chain that consists of an amino acid sequence at least 90%, 91%, 92%, 93%, 94%, 95%, 96%, 97%, 98%, 99%, or 100% identical to the amino acid sequence of SEQ ID NO: 67; and a light chain that consists of an amino acid sequence at least 90%, 91%, 92%, 93%, 94%, 95%, 96%, 97%, 98%, 99%, or 100% identical to the amino acid sequence of SEQ ID NO: 55.

TABLE 5

Exemplary Fusion Proteins

| Fusion | Component | Amino Acid Sequence | SEQ ID NO |
|---|---|---|---|
| BCA101 | Heavy Chain<br>Anti-EGFR heavy chain<br>VH Underlined<br>CDRs Underlined & Bold | QVQLKQSGPGLVQPSQSLSITCTVSGFSLT**NYGVH**WVRQS<br>PGKGLEWLG**VIWSGGNTDYNTPFTS**RLSINKDNSKSQVFF<br>KMNSLQSNDTAIYYCAR**ALTYYDYEFAY**WGQGTLVTVSAA<br>STKGPSVFPLAPSSKSTSGGTAALGCLVKDYFPEPVTVSW<br>NSGALTSGVHTFPAVLQSSGLYSLSSVVTVPSSSLGTQTY<br>ICNVNHKPSNTKVDKRVEPKSCDKTHTCPPCPAPELLGGP<br>SVFLFPPKPKDTLMISRTPEVTCVVVDVSHEDPEVKENWY<br>VDGVEVHNAKTKPREEQYNSTYRVVSVLTVLHQDWLNGKE<br>YKCKVSNKALPAPIEKTISKAKGQPREPQVYTLPPSRDEL<br>TKNQVSLTCLVKGFYPSDIAVEWESNGQPENNYKTTPPVL<br>DSDGSFFLYSKLTVDKSRWQQGNVFSCSVMHEALHNHYTQ<br>KSLSLSPG | 43 |
| | Light Chain<br>Anti-EGFR light chain<br>VL Underlined<br>CDRs Underlined & Bold<br>Linker italicized<br>TGFβR ECD Bold | DILLTQSPVILSVSPGERVSFSC**RASQSIGTNI**HWYQQRT<br>NGSPRLLIK**YASESIS**GIPSRFSGSGSGTDFTLSINSVES<br>EDIADYYC**QQNNNWPTT**FGAGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC*GGGGSGGGGSGGGGS***TIPPHVQKSVN**<br>**NDMIVTDNNGAVKFPQLCKFCDVRFSTCDNQKSCMSNCSI**<br>**TSICEKPQEVCVAVWRKNDENITLETVCHDPKLPYHDFIL**<br>**EDAASPKCIMKEKKKPGETFFMCSCSSDECNDNIIFSEEY**<br>**NTSNPD** | 62 |

TABLE 5-continued

| Exemplary Fusion Proteins | | | |
|---|---|---|---|
| Fusion | Component | Amino Acid Sequence | SEQ ID NO |
| Heavy Chain Fusion | Heavy Chain<br>Anti-EGFR heavy chain<br>VH Underlined<br>CDRs Underlined & Bold<br>Linker italicized<br>TGFβR ECD Bold | QVQLKQSGPGLVQPSQSLSITCTVSGFSLT**NYGVH**WVRQS<br>PGKGLEWLG**VIWSGGNTDYNTPFTS**RLSINKDNSKSQVFF<br>KMNSLQSNDTAIYYCAR**ALTYYDYEFAY**WGQGTLVTVSAA<br>STKGPSVFPLAPSSKSTSGGTAALGCLVKDYFPEPVTVSW<br>NSGALTSGVHTFPAVLQSSGLYSLSSVVTVPSSSLGTQTY<br>ICNVNHKPSNTKVDKRVEPKSCDKTHTCPPCPAPELLGGP<br>SVFLFPPKPKDTLMISRTPEVTCVVVDVSHEDPEVKENWY<br>VDGVEVHNAKTKPREEQYNSTYRVVSVLTVLHQDWLNGKE<br>YKCKVSNKALPAPIEKTISKAKGQPREPQVYTLPPSRDEL<br>TKNQVSLTCLVKGFYPSDIAVEWESNGQPENNYKTTPPVL<br>DSDGSFFLYSKLTVDKSRWQQGNVFSCSVMHEALHNHYTQ<br>KSLSLSP*GGGGGSGGGGSGGGGS*TIPPHVQKSVNNDMIVT<br>**DNNGAVKFPQLCKFCDVRFSTCDNQKSCMSNCSITSICEK**<br>**PQEVCVAVWRKNDENITLETVCHDPKLPYHDFILEDAASP**<br>**KCIMKEKKKPGETFFMCSCSSDECNDNIIFSEEYNTSNPD** | 63 |
| | Light Chain<br>Anti-EGFR light chain<br>VL Underlined<br>CDRs Underlined & Bold | DILLTQSPVILSVSPGERVSFSC**RASQSIGTNI**HWYQQRT<br>NGSPRLLIK**YASESIS**GIPSRFSGSGSGTDFTLSINSVES<br>EDIADYYC**QQNNNWPTT**FGAGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSENRGEC | 44 |
| Cetuximab Light Chain Fusion | Heavy Chain<br>Anti-EGFR heavy chain<br>VH Underlined<br>CDRs Underlined & Bold | QVQLKQSGPGLVQPSQSLSITCTVSGFSLT**NYGVH**WVRQS<br>PGKGLEWLG**VIWSGGNTDYNTPFTS**RLSINKDNSKSQVFF<br>KMNSLQSNDTAIYYCAR**ALTYYDYEFAY**WGQGTLVTVSAA<br>STKGPSVFPLAPSSKSTSGGTAALGCLVKDYFPEPVTVSW<br>NSGALTSGVHTFPAVLQSSGLYSLSSVVTVPSSSLGTQTY<br>ICNVNHKPSNTKVDKRVEPKSCDKTHTCPPCPAPELLGGP<br>SVFLFPPKPKDTLMISRTPEVTCVVVDVSHEDPEVKENWY<br>VDGVEVHNAKTKPREEQYNSTYRVVSVLTVLHQDWLNGKE<br>YKCKVSNKALPAPIEKTISKAKGQPREPQVYTLPPSRDEL<br>TKNQVSLTCLVKGFYPSDIAVEWESNGQPENNYKTTPPVL<br>DSDGSFFLYSKLTVDKSRWQQGNVFSCSVMHEALHNHYTQ<br>KSLSLSPGK | 42 |
| | Light Chain<br>Anti-EGFR light chain<br>VL Underlined<br>CDRs Underlined & Bold<br>Linker italicized<br>TGFβR ECD Bold | DILLTQSPVILSVSPGERVSFSC**RASQSIGTNI**HWYQQRT<br>NGSPRLLIK**YASESIS**GIPSRFSGSGSGTDETLSINSVES<br>EDIADYYC**QQNNNWPTT**FGAGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC*GGGGSGGGGSGGGGS*TIPPHVQKSVN<br>NDMIVTDNNGAVKFPQLCKFCDVRFSTCDNQKSCMSNCSI<br>**TSICEKPQEVCVAVWRKNDENITLETVCHDPKLPYHDFIL**<br>**EDAASPKCIMKEKKKPGETFFMCSCSSDECNDNIIFSEEY**<br>**NTSNPD** | 62 |
| Cetuximab Heavy Chain Fusion | Heavy Chain<br>Anti-EGFR heavy chain<br>VH Underlined<br>CDRs Underlined & Bold<br>Linker italicized<br>TGEβR ECD Bold | QVQLKQSGPGLVQPSQSLSITCTVSGFSLT**NYGVH**WVRQS<br>PGKGLEWLG**VIWSGGNTDYNTPFT**SRLSINKDNSKSQVFF<br>KMNSLQSNDTAIYYCAR**ALTYYDYEFAY**WGQGTLVTVSAA<br>STKGPSVFPLAPSSKSTSGGTAALGCLVKDYFPEPVTVSW<br>NSGALTSGVHTFPAVLQSSGLYSLSSVVTVPSSSLGTQTY<br>ICNVNHKPSNTKVDKRVEPKSCDKTHTCPPCPAPELLGGP<br>SVFLFPPKPKDTLMISRTPEVTCVVVDVSHEDPEVKENWY<br>VDGVEVHNAKTKPREEQYNSTYRVVSVLTVLHQDWLNGKE<br>YKCKVSNKALPAPIEKTISKAKGQPREPQVYTLPPSRDEL<br>TKNQVSLTCLVKGFYPSDIAVEWESNGQPENNYKTTPPVL<br>DSDGSFFLYSKLTVDKSRWQQGNVFSCSVMHEALHNHYTQ<br>KSLSLSPGK*GGGGSGGGGSGGGGS*TIPPHVQKSVNNDMIV<br>**TDNNGAVKFPQLCKFCDVRESTCDNQKSCMSNCSITSICE**<br>**KPQEVCVAVWRKNDENITLETVCHDPKLPYHDFILEDAAS**<br>**PKCIMKEKKKPGETFFMCSCSSDECNDNIIFSEEYNTSNP**<br>**D** | 64 |
| | Light Chain<br>Anti-EGFR light chain<br>VL Underlined<br>CDRs Underlined & Bold | DILLTQSPVILSVSPGERVSFSC**RASQSIGTNI**HWYQQRT<br>NGSPRLLIK**YASESIS**GIPSRFSGSGSGTDFTLSINSVES<br>EDIADYYC**QQNNNWPTT**FGAGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSENRGEC | 44 |
| Panitumumab Light Chain Fusion (with | Heavy Chain<br>Anti-EGFR heavy chain | QVQLQESGPGLVKPSETLSLTCTVSGGSVS**SGDYYWT**WIR<br>QSPGKGLEWIG**HIYYSGNTNYNPSLKS**RLTISIDTSKTQF<br>SLKLSSVTAADTAIYYCVR**DRVTGAFDI**WGQGTMVTVSSA | 53 |

TABLE 5-continued

Exemplary Fusion Proteins

| Fusion | Component | Amino Acid Sequence | SEQ ID NO |
|---|---|---|---|
| HC C terminal Lysine) | VH Underlined CDRs Underlined & Bold | STKGPSVFPLAPCSRSTSESTAALGCLVKDYFPEPVTVSW<br>NSGALTSGVHTFPAVLQSSGLYSLSSVVTVPSSNFGTQTY<br>TCNVDHKPSNTKVDKTVERKCCVECPPCPAPPVAGPSVEL<br>FPPKPKDTLMISRTPEVTCVVVDVSHEDPEVQFNWYVDGV<br>EVHNAKTKPREEQFNSTFRVVSVLTVVHQDWLNGKEYKCK<br>VSNKGLPAPIEKTISKTKGQPREPQVYTLPPSREEMTKNQ<br>VSLTCLVKGFYPSDIAVEWESNGQPENNYKTTPPMLDSDG<br>SFFLYSKLTVDKSRWQQGNVFSCSVMHEALHNHYTQKSLS<br>LSPGK | |
| | Light Chain Anti-EGFR light chain VL Underlined CDRs Underlined & Bold Linker italicized TGFβR ECD Bold | DIQMTQSPSSLSASVGDRVTITC**QASQDISNYLN**WYQQKP<br>GKAPKLLIY**DASNLET**GVPSRFSGSGSGTDFTFTISSLQP<br>EDIATYFC**QHFDHLPLA**FGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC*GGGGSGGGGSGGGGS***TIPPHVQKSVN**<br>**NDMIVTDNNGAVKFPQLCKFCDVRFSTCDNQKSCMSNCSI**<br>**TSICEKPQEVCVAVWRKNDENITLETVCHDPKLPYHDFIL**<br>**EDAASPKCIMKEKKKPGETFFMCSCSSDECNDNIIFSEEY**<br>**NTSNPD** | 65 |
| Panitumumab Heavy Chain fusion (with HC C terminal Lysine) | Heavy Chain Anti-EGFR heavy chain VH Underlined CDRs Underlined & Bold Linker italicized TGFβR ECD Bold | QVQLQESGPGLVKPSETLSLTCTVSGGSVS**SGDYYWT**WIR<br>QSPGKGLEWIG**HIYYSGNTNYNPSLKS**RLTISIDTSKTQF<br>SLKLSSVTAADTAIYYCVR**DRVTGAFDI**WGQGTMVTVSSA<br>STKGPSVFPLAPCSRSTSESTAALGCLVKDYFPEPVTVSW<br>NSGALTSGVHTFPAVLQSSGLYSLSSVVTVPSSNFGTQTY<br>TCNVDHKPSNTKVDKTVERKCCVECPPCPAPPVAGPSVEL<br>FPPKPKDTLMISRTPEVTCVVVDVSHEDPEVQFNWYVDGV<br>EVHNAKTKPREEQFNSTFRVVSVLTVVHQDWLNGKEYKCK<br>VSNKGLPAPIEKTISKTKGQPREPQVYTLPPSREEMTKNQ<br>VSLTCLVKGFYPSDIAVEWESNGQPENNYKTTPPMLDSDG<br>SFFLYSKLTVDKSRWQQGNVFSCSVMHEALHNHYTQKSLS<br>LSPGK*GGGGSGGGGSGGGGS***TIPPHVQKSVNNDMIVTDNN**<br>**GAVKFPQLCKFCDVRFSTCDNQKSCMSNCSITSICEKPQE**<br>**VCVAVWRKNDENITLETVCHDPKLPYHDFILEDAASPKCI**<br>**MKEKKKPGETFFMCSCSSDECNDNIIFSEEYNTSNPD** | 66 |
| | Light Chain Anti-EGFR light chain VL Underlined CDRs Underlined & Bold | DIQMTQSPSSLSASVGDRVTITC**QASQDISNYLN**WYQQKP<br>GKAPKLLIY**DASNLET**GVPSRFSGSGSGTDFTFTISSLQP<br>EDIATYFC**QHFDHLPLA**FGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSENRGEC | 55 |
| Panitumumab Light Chain Fusion (with HC C terminal Lysin) | Heavy Chain Anti-EGFR heavy chain VH Underlined CDRs Underlined & Bold | QVQLQESGPGLVKPSETLSLTCTVSGGSVS**SGDYYWT**WIR<br>QSPGKGLEWIG**HIYYSGNTNYNPSLKS**RLTISIDTSKTQF<br>SLKLSSVTAADTAIYYCVR**DRVTGAFDI**WGQGTMVTVSSA<br>STKGPSVFPLAPCSRSTSESTAALGCLVKDYFPEPVTVSW<br>NSGALTSGVHTFPAVLQSSGLYSLSSVVTVPSSNFGTQTY<br>TCNVDHKPSNTKVDKTVERKCCVECPPCPAPPVAGPSVFL<br>FPPKPKDTLMISRTPEVTCVVVDVSHEDPEVQFNWYVDGV<br>EVHNAKTKPREEQFNSTFRVVSVLTVVHQDWLNGKEYKCK<br>VSNKGLPAPIEKTISKTKGQPREPQVYTLPPSREEMTKNQ<br>VSLTCLVKGFYPSDIAVEWESNGQPENNYKTTPPMLDSDG<br>SFFLYSKLTVDKSRWQQGNVFSCSVMHEALHNHYTQKSLS<br>LSPG | 54 |
| | Light Chain Anti-EGFR light chain VL Underlined CDRs Underlined & Bold Linker italicized TGFβR ECD Bold | DIQMTQSPSSLSASVGDRVTITC**QASQDISNYLN**WYQQKP<br>GKAPKLLIY**DASNLET**GVPSRFSGSGSGTDFTFTISSLQP<br>EDIATYFC**QHFDHLPLA**FGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC*GGGGSGGGGSGGGGS***TIPPHVQKSVN**<br>**NDMIVTDNNGAVKFPQLCKFCDVRFSTCDNQKSCMSNCSI**<br>**TSICEKPQEVCVAVWRKNDENITLETVCHDPKLPYHDFIL**<br>**EDAASPKCIMKEKKKPGETFFMCSCSSDECNDNIIFSEEY**<br>**NTSNPD** | 65 |
| Panitumumab Heavy Chain fusion (with HC C terminal Lysine) | Heavy Chain Anti-EGFR heavy chain VH Underlined CDRs Underlined & Bold Linker | QVQLQESGPGLVKPSETLSLTCTVSGGSVS**SGDYYW**TWIR<br>QSPGKGLEWIG**HIYYSGNTNYNPSLKS**RLTISIDTSKTQF<br>SLKLSSVTAADTAIYYCVR**DRVTGAFDI**WGQGTMVTVSSA<br>STKGPSVFPLAPCSRSTSESTAALGCLVKDYFPEPVTVSW<br>NSGALTSGVHTFPAVLQSSGLYSLSSVVTVPSSNFGTQTY<br>TCNVDHKPSNTKVDKTVERKCCVECPPCPAPPVAGPSVFL<br>FPPKPKDTLMISRTPEVTCVVVDVSHEDPEVQFNWYVDGV | 67 |

TABLE 5-continued

Exemplary Fusion Proteins

| Fusion | Component | Amino Acid Sequence | SEQ ID NO |
|---|---|---|---|
| | italicized TGFβR ECD Bold | EVHNAKTKPREEQFNSTFRVVSVLTVVHQDWLNGKEYKCK VSNKGLPAPIEKTISKTKGQPREPQVYTLPPSREEMTKNQ VSLTCLVKGFYPSDIAVEWESNGQPENNYKTTPPMLDSDG SFFLYSKLTVDKSRWQQGNVFSCSVMHEALHNHYTQKSLS LSPGG*GGGGSGGGGSGGGGS***TIPPHVQKSVNNDMIVTDNN GAVKFPQLCKFCDVRFSTCDNQKSCMSNCSITSICEKPQE VCVAVWRKNDENITLETVCHDPKLPYHDFILEDAASPKCI MKEKKKPGETFFMCSCSSDECNDNIIFSEEYNTSNPD** | |
| | Light Chain Anti-EGFR light chain VL Underlined CDRs Underlined & Bold | DIQMTQSPSSLSASVGDRVTITC**QASQDISNYLN**WYQQKP GKAPKLLIY**DASNLET**GVPSRFSGSGSGTDFTFTISSLQP EDIATYFC**QHFDHLPLA**FGGGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSENRGEC | 55 |

Methods of Making Fusion Proteins

Fusion proteins described herein can be made by any conventional technique known in the art, for example, recombinant techniques or chemical synthesis (e.g., solid phase peptide synthesis). In one embodiments, the fusion protein is made through recombinant expression in a cell. Briefly, the fusion protein can be made by synthesizing the DNA encoding the fusion protein and cloning the DNA into any suitable expression vector. Numerous cloning vectors are known to those of skill in the art, and the selection of an appropriate cloning vector is a matter of choice. The gene can be placed under the control of a promoter, ribosome binding site (for bacterial expression) and, optionally, an operator, so that the DNA sequence encoding the fusion protein is transcribed into RNA in the host cell transformed by a vector containing this expression construction. The coding sequence may or may not contain a signal peptide or leader sequence. Heterologous leader sequences can be added to the coding sequence that causes the secretion of the expressed polypeptide from the host organism. Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

The expression vector may then used to transform an appropriate host cell. A number of mammalian cell lines are known in the art and include immortalized cell lines available from the American Type Culture Collection (ATCC), such as, but not limited to, Chinese hamster ovary (CHO) cells, CHO-suspension cells (CHO-S), HeLa cells, HEK293, baby hamster kidney (BHK) cells, monkey kidney cells (COS), VERO, HepG2, MadinDarby bovine kidney (MDBK) cells, NOS, U2OS, A549, HT1080, CAD, P19, NIH3T3, L929, N2a, MCF-7, Y79, SO-Rb50, DUKX-X11, and J558L. In some embodiments, the fusion protein is produced in CHO or CHO-S cells.

Depending on the expression system and host selected, the fusion protein is produced by growing host cells transformed by an expression vector described above under conditions whereby the fusion protein is expressed. The fusion protein is then isolated from the host cells and purified. If the expression system secretes the fusion protein into growth media, the fusion protein can be purified directly from the media. If the fusion protein is not secreted, it is isolated from cell lysates. The selection of the appropriate growth conditions and recovery methods are within the skill of the art. Once purified, the amino acid sequences of the fusion proteins can be determined, i.e., by repetitive cycles of Edman degradation, followed by amino acid analysis by HPLC. Other methods of amino acid sequencing are also known in the art. Once purified, the functionality of the fusion protein can be assessed, e.g., as described herein, e.g., utilizing a bifunctional ELISA.

As described above, functionality of the fusion protein can be tested by any method known in the art, e.g., ELISA. Each functionality can be measured in a separate assay, e.g., TGFβ binding and EGFR binding can be measured in two separate ELISAs. For example, an ELISA plate can be coated with EGFR Fc chimera, and used to evaluate EGFR binding; and a separate ELISA plate can be coated with TGFβ-1 to evaluate TGFβ-1 binding. Both functionalities can also be evaluated in a bifunctional ELISA. For example, an anti-idiotype mAb against cetuximab (for use with BCA101 fusion protein) can be used to capture BCA101 and the bound BCA101 can be detected by an enzyme-labeled polyclonal antibody against TGFβRIIECD. The concentration of BCA101 in samples can be back-calculated from a BCA101 calibration curve. Target binding can also be evaluated via Biocore, wherein EGFR and TGFβ1 targets are immobilized on activated CM5 chips and then incubated with serial concentrations of the fusion protein. Additional in vitro functional assays can also be performed to evaluate the fusion proteins, including for example, cell surface binding by flow cytometry, inhibition of cell proliferation, ADCC assay, neutralization of TGFβ1 induced IL-11 release; neutralization of TGFβ1 induced SMAD signaling.

Methods of Use

In one aspect, provided herein are methods of treating cancer in a subject by administering to the subject having cancer an agent that specifically binds PD1 (e.g., an agent described herein) and a fusion protein that comprises a targeting moiety and an immunomodulatory moiety, wherein: i) said targeting moiety specifically binds epidermal growth factor receptor (EGFR); and (ii) said immunomodulatory moiety comprises an amino acid sequence of the extracellular domain of transforming growth factor-beta receptor II (TGFβRII).

In some embodiments, the methods disclosed herein are used in place of standard of care therapies. In certain embodiments, a standard of care therapy is used in combination with any method disclosed herein. Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers. In some embodiments, the methods disclosed herein are used after standard of care therapy has failed.

In some embodiments, the fusion protein is co-administered, administered prior to, or administered after, the antibody, or functional fragment or functional variant thereof, that specifically binds PD1.

In some embodiments, the fusion protein is co-administered with the antibody, or functional fragment or functional variant thereof, that specifically binds PD1. In some embodiments, the fusion protein is administered simultaneously with the antibody, or functional fragment or functional variant thereof, that specifically binds PD1. In some embodiments, the fusion protein is administered within 30 minutes, 1 hour, 2 hours, 3 hours, 4 hours, 5 hours, 6 hours, 7 hours, 8 hours, 9 hours, 10 hours, 11 hours, or 12 hours of administration of the antibody, or functional fragment or functional variant thereof, that specifically binds PD1.

In some embodiments, the fusion protein is administered prior to administration of the antibody, or functional fragment or functional variant thereof, that specifically binds PD1. In some embodiments, the fusion protein is administered at least 30 minutes, 1 hour, 3 hours, 6 hours, 12 hours, 24 hours, 48 hours, 72 hours, 4 days, 5 days, 6 days, 7 days, or 14 days prior to administration of the antibody, or functional fragment or functional variant thereof, that specifically binds PD1.

In some embodiments, the fusion protein is administered after administration of the antibody, or functional fragment or functional variant thereof, that specifically binds PD1. In some embodiments, the fusion protein is administered at least 30 minutes, 1 hour, 3 hours, 6 hours, 12 hours, 24 hours, 48 hours, 72 hours, 4 days, 5 days, 6 days, 7 days, or 14 days after administration of the antibody, or functional fragment or functional variant thereof, that specifically binds PD1.

Exemplary Cancers

In some embodiments, the cancer is metastatic. In some embodiments, the cancer is recurrent. In some embodiments, the cancer is metastatic and recurrent. In some embodiments, the cancer is refractory to the approved standard of care. In some embodiments, the cancer is refractory to at least one approved standard of care. In some embodiments, the cancer is refractory to at least all approved standard of care therapeutics.

In some embodiments, the cancer is EGFR-driven. In some embodiments, the cancer is a solid tumor. In some embodiments, the cancer is a hematological malignancy. In some embodiments, the cancer is selected from the group consisting of breast cancer, anal cancer, pancreatic cancer, thyroid cancer, liver cancer, ovarian cancer, lung cancer, skin cancer, brain cancer, spinal cord cancer, head cancer, neck cancer, and head and neck cancer.

In some embodiments, the cancer is head and neck cancer. In some embodiments, the cancer is head and neck squamous cell carcinoma (HNSCC). In some embodiments, the cancer is recurrent HNSCC. In some embodiments, the cancer is metastatic HNSCC. In some embodiments, the cancer is metastatic and recurrent HNSCC. In some embodiments, the cancer is anal canal. In some embodiments, the cancer is squamous cell carcinoma of anal canal (SCCAC). In some embodiments, the cancer is recurrent SCCAC. In some embodiments, the cancer is metastatic SCCAC. In some embodiments, the cancer is metastatic and recurrent SCCAC.

Dosing Regimens and Schedules

Anti-PD1 Antibodies

In some embodiments, the antibody, or functional fragment or functional variant thereof, that specifically binds PD1 is administered to the subject having cancer at a therapeutically effective dose. In some embodiments, the antibody, or functional fragment or functional variant thereof, that specifically binds PD1 is administered to the subject having cancer at a fixed dose. In some embodiments, the antibody, or functional fragment or functional variant thereof, that specifically binds PD1 is administered to the subject having cancer at a flat dose. In some embodiments, the antibody, or functional fragment or functional variant thereof, that specifically binds PD1 is administered to the subject having cancer at a weight based dose.

In some embodiments, the antibody, or functional fragment or functional variant thereof, that specifically binds PD1 is administered to the subject having cancer at a dose from about 100 mg to 500 mg, 100 mg to 400 mg, 100 mg to 300 mg, or 100 mg to 200 mg. In some embodiments, the antibody, or functional fragment or functional variant thereof, that specifically binds PD1 is administered to the subject having cancer at a dose of about 100 mg, 200 mg, 300 mg, 400 mg, or 500 mg. In some embodiments, the antibody, or functional fragment or functional variant thereof, that specifically binds PD1 is administered to the subject having cancer at a dose of about 200 mg. In some embodiments, the antibody, or functional fragment or functional variant thereof, that specifically binds PD1 is administered to the subject having cancer at a dose of about 300 mg.

In some embodiments, the antibody, or functional fragment or functional variant thereof, that specifically binds PD1 is administered to the subject having cancer about every 1, 2, 3, 4, 5, 6, 7, or 8 weeks. In some embodiments, the antibody, or functional fragment or functional variant thereof, that specifically binds PD1 is administered to the subject having cancer about every 1 week. In some embodiments, the antibody, or functional fragment or functional variant thereof, that specifically binds PD1 is administered to the subject having cancer about every 2 weeks. In some embodiments, the antibody, or functional fragment or functional variant thereof, that specifically binds PD1 is administered to the subject having cancer about every 3 weeks.

In some embodiments, the antibody, or functional fragment or functional variant thereof, that specifically binds PD1 is pembrolizumab. In some embodiments, pembrolizumab is administered to the subject at a dose of from about 100 mg to 500 mg, 100 mg to 400 mg, 100 mg to 300 mg, or 100 mg to 200 mg. In some embodiments, pembrolizumab is administered at a dose of about 100 mg, 200 mg, 300 mg, 400 mg, or 500 mg. In some embodiments, pembrolizumab is administered at a dose of about 200 mg. In some embodiments, pembrolizumab is administered at a dose of about 300 mg. In some embodiments, pembrolizumab is administered at a dose of about 400 mg.

In some embodiments, pembrolizumab is administered to the subject about every 1, 2, 3, 4, 5, 6, 7, or 8 weeks. In some embodiments, pembrolizumab is administered to the subject about every 2 weeks. In some embodiments, pembrolizumab is administered to the subject about every 3 weeks. In some embodiments, pembrolizumab is administered to the subject about every 4 weeks. In some embodiments, pembrolizumab is administered to the subject about every 5 weeks. In some embodiments, pembrolizumab is administered to the subject about every 6 weeks.

In some embodiments, pembrolizumab is administered to the subject at a dose of about 200 mg every 3 weeks. In some embodiments, pembrolizumab is administered to the subject at a dose of about 400 mg every 6 weeks.

In some embodiments, the antibody, or functional fragment or functional variant thereof, that specifically binds PD1 is nivolumab. In some embodiments, nivolumab is administered to the subject at a dose of from about 100 mg to 500 mg, 100 mg to 400 mg, 100 mg to 300 mg, or 100 mg to 200 mg. In some embodiments, nivolumab is administered at a dose of about 100 mg, 200 mg, 300 mg, 400 mg, or 500 mg. In some embodiments, nivolumab is administered at a dose of about 200 mg. In some embodiments, nivolumab is administered at a dose of about 240 mg. In some embodiments, nivolumab is administered at a dose of about 300 mg. In some embodiments, nivolumab is administered at a dose of about 360 mg. In some embodiments, nivolumab is administered at a dose of about 400 mg. In some embodiments, nivolumab is administered at a dose of about 480 mg. In some embodiments, nivolumab is administered at a dose of about 500 mg.

In some embodiments, nivolumab is administered to the subject at a dose of from about 1 mg/kg to 5 mg/kg, 1 mg/kg to 4 mg/kg, 1 mg/kg to 3 mg/kg, or 1 mg/kg to 2 mg/kg. In some embodiments, nivolumab is administered at a dose of about 1 mg/kg, 2 mg/kg, 3 mg/kg, 4 mg/kg, or 5 mg/kg. In some embodiments, nivolumab is administered at a dose of about 1 mg/kg. In some embodiments, nivolumab is administered at a dose of about 2 mg/kg. In some embodiments, nivolumab is administered at a dose of about 3 mg/kg.

In some embodiments, nivolumab is administered to the subject about every 1, 2, 3, 4, 5, 6, 7, or 8 weeks. In some embodiments, nivolumab is administered to the subject about every 2 weeks. In some embodiments, nivolumab is administered to the subject about every 3 weeks. In some embodiments, nivolumab is administered to the subject about every 4 weeks. In some embodiments, nivolumab is administered to the subject about every 5 weeks. In some embodiments, nivolumab is administered to the subject about every 6 weeks.

In some embodiments, nivolumab is administered to the subject at a dose of about 240 mg every 2 weeks. In some embodiments, nivolumab is administered to the subject at a dose of about 480 mg every 4 weeks. In some embodiments, nivolumab is administered at a dose of about 360 mg every 3 weeks. In some embodiments, nivolumab is administered to the subject at a dose of about 1 mg/kg every 3 weeks. In some embodiments, nivolumab is administered to the subject at a dose of about 3 mg/kg every 2 weeks.

Fusion Proteins

In some embodiments, the fusion protein (i.e. fusion protein that comprises a targeting moiety and an immunomodulatory moiety, wherein: i) said targeting moiety specifically binds epidermal growth factor receptor (EGFR); and (ii) said immunomodulatory moiety comprises an amino acid sequence of the extracellular domain of transforming growth factor-beta receptor II (TGFβRII)), is administered to the subject having cancer at a therapeutically effective dose. In some embodiments, the fusion protein is administered to the subject having cancer at a fixed dose. In some embodiments, the fusion protein is administered to the subject having cancer at a flat dose. In some embodiments, the fusion protein is administered to the subject having cancer at a weight based dose.

In some embodiments, the fusion protein is administered to the subject at a dose from about 50 mg to 2000 mg, 100 mg to 2000 mg, 150 mg to 2000 mg, 200 mg to 2000 mg, 300 mg to 2000 mg, 400 mg to 2000 mg, 500 mg to 2000 mg, 600 mg to 2000 mg, 700 mg to 2000 mg, 800 mg to 2000 mg, 9000 mg to 2000 mg, 1000 mg to 2000 mg, 1500 mg to 2000 mg, 50 mg to 100 mg, 50 mg to 500 mg, 50 mg to 400 mg, 50 mg to 300 mg, 50 mg to 200 mg, 50 mg to 100 mg, 100 mg to 500 mg, 100 mg to 400 mg, 100 mg to 300 mg, or 100 mg to 200 mg. In some embodiments, the fusion protein is administered to the subject at a dose of from about 200 mg to 2000 mg. In some embodiments, the fusion protein is administered to the subject at a dose of about 50 mg, 60 mg, 64 mg, 100 mg, 150 mg, 200 mg, 240 mg, 250 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900, or 2000 mg. In some embodiments, the fusion protein is administered to the subject at a dose of about 64 mg, 240 mg, 800 mg, or 1600 mg. In some embodiments, the fusion protein is administered to the subject at a dose of about 64 mg. In some embodiments, the fusion protein is administered to the subject at a dose of about 240 mg. In some embodiments, the fusion protein is administered to the subject at a dose of about 800 mg. In some embodiments, the fusion protein is administered to the subject at a dose of about 1600 mg.

In some embodiments, the fusion protein is administered to the subject every 1, 2, 3, 4, 5, or 6 weeks. In some embodiments, the fusion protein is administered to the subject every week. In some embodiments, the fusion protein is administered to the subject every 2 weeks. In some embodiments, the fusion protein is administered to the subject every 3 weeks. In some embodiments, the fusion protein is administered to the subject every 4 weeks. In some embodiments, the fusion protein is administered to the subject 5 weeks. In some embodiments, the fusion protein is administered to the subject every 6 weeks.

Kits

In one aspect, provided herein are kits comprising an anti-PD-1 antibody and a fusion protein described herein for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) a dosage of an anti-PD-1 antibody; and (b) a dosage of a fusion protein described herein and (c) instructions for using the anti-PD-1 antibody and the fusion protein in any of the combination therapy methods disclosed herein. In certain embodiments, the anti-PD-1 antibody, the fusion protein can be co-packaged in unit dosage form. In certain embodiments for treating human patients, the kit comprises an anti-human PD-1 antibody disclosed herein, e.g., pembrolizumab.

The present invention is further illustrated by the following examples which should not be construed as further limiting. The contents of all references cited throughout this application are expressly incorporated herein by reference.

EXAMPLES

Example 1. Evaluation of the Anti-Cancer Activity of BCA101 in Combination with an Anti-PD1 Antibody in huNOG-EXL Mice Bearing Subcutaneous PC-3 Tumor Xenograft The objective of this study was to evaluate the anti-cancer activity of BCA101 alone and in combination with anti-PD1 antibody pembrolizumab in vivo.

Materials and Methods

Mice

The study utilized immunodeficient hGM-CSF/hIL3 transgenic-NOG mice which upon engraftment with human hematopoietic stem cells, exhibit in a human-like immune system (lymphoid & myeloid lineage of human origin). This model enabled the study of key innate mechanisms involved in the efficacy of immuno-therapy related agents and provided a suitable model for establishment of human xenografts.

Male hGM-CSF/hIL3 NOG mice were obtained from Taconic Biosciences. hGM-CSF/hIL3 NOG mice engrafted with human CD34+ hematopoietic stem cells (HSCs) stably developed extensive cell lineages as early as 6 to 8 weeks' post-injection. Both myeloid and lymphoid lineage cells were present in peripheral blood, bone marrow, thymus and spleen and non-lymphoid tissue including lung and liver. huNOG-EXL mice with greater than 25% hCD45+ in peripheral blood were used. The age of the mice at the start of each study was 13-14 weeks, with a mean body weight of the animals per group of approximately 26 g.

Preparation and Subcutaneous Injection of Tumor Cells

All procedures were performed in a laminar flow hood following sterile techniques. PC-3 (Human prostate adenocarcinoma) cells with a viability of >90% were utilized. Around $5\times10^6$ cells were re-suspended in 2001A1 of serum free media containing 50% of matrigel kept in ice.

PC-3 cell line was propagated in male huNOG-EXL mice by injecting the cells subcutaneously in the right flank region of the mice. The implanted area was monitored for tumor growth. Once the tumor attained palpable stage and required volume, the mice were randomized based on tumor volume (Mean tumor volume≈119 $mm^3$) and dosing was initiated. The study schedule is described in Table 6.

TABLE 6

Study Schedule

| Groups | No. of Animals | Tumor Type | Tumor Volume (at initiation of study) | Dose, Route and Dosing Schedule | Treatment Period |
|---|---|---|---|---|---|
| Group I Isotype Control | 10 | PC-3 | ~119 $mm^3$ | 8.1 mg/kg; intraperitoneal; Biweekly × 6 doses | 21 days |
| Group II Cetuximab | 10 | PC-3 | ~119 $mm^3$ | 8.1 mg/kg; intraperitoneal; Biweekly × 6 doses | 21 days |
| Group III BCA101 | 10 | PC-3 | ~119 $mm^3$ | 10 mg/kg; intraperitoneal; Biweekly × 6 doses | 21 days |
| Group IV Anti-PD1 (pembrolizumab) | 10 | PC-3 | ~119 $mm^3$ | 10 mg/kg; intraperitoneal; Q5D × 5 doses | 21 days |
| Group V BCA101 + Anti-PD1 (pembrolizumab) | 10 | PC-3 | ~119 $mm^3$ | BCA101: 10 mg/kg; intraperitoneal; Biweekly × 6 doses Anti-PD1: 10 mg/kg; intraperitoneal; Q5D × 5 doses | 21 days |

Formulation of Antibody Doses

Required quantities of human IgG1 isotype control, cetuximab, BCA101, and pembrolizumab were diluted in diluent buffer to obtain an appropriate working concentration to deliver the intended dose. The dose volume of 10 mL/kg intraperitoneally was maintained for all the animals. Whereas, in combination treatment (Group V) on day 0, dose volume of 5 mL/kg was used for both BCA101 and pembrolizumab dosing to maintain the total dose volume of 10 mL/kg per mouse.

Observations

Body Weight and Clinical Sign

Individual body weight was measured every third day during experimental period. The % change in body weight of individual mice was calculated and recorded. Mice were observed for visible clinical sign and recorded every third day during experimental period.

Tumor Volume

The tumor volume was determined by two-dimensional measurement of length (L) and width (W) of the tumor with a digital Vernier caliper on the day of randomization (Day 0) and then every third day during the experimental period. Tumor volume (TV) was calculated using the following formula: Tumor Volume (mm3)=$(L\times W^2)/2$, wherein L=length (mm) and W=width (mm). Mean, Standard Deviation (SD) or Standard Error of Mean (SEM) were calculated for individual groups.

Antitumor Activity

Antitumor activity was evaluated as maximum tumor growth inhibition versus the isotype control group. Data evaluation was performed using standard calculations in Microsoft Excel.

Test/Control Value in % (% T/C)

Tumor inhibition on a particular day (T/C in %) was calculated by using the below formula: % T/C Day X=((Mean TV of test group on day x−Mean TV of test group on day 0)/(Mean TV of control group on day x−Mean TV of control group on day 0))×100%; wherein TV=tumor volume in $mm^3$. The minimum (or optimum) % T/C value recorded for a particular test group during an experiment represents the maximum antitumor activity for the respective treatment.

Tumor Growth Inhibition (TGI)

TGI was calculated using the following formula: TGI=(1−T/C)×100%; wherein T=(Mean TV of the test group on Day X−Mean TV of the test group on Day 0; and C=(Mean TV of the control group on Day X−Mean TV of the control group on Day 0).

Statistical Analysis

For the evaluation of the statistical significance of tumor inhibition, a Two-way ANOVA followed by Bonferroni post hoc test was performed using Graph Pad Prism V 8.3.0. p values <0.05 indicate statistically significant differences between groups.

Necropsy

Based on ethical reasons and tumor end points animals showing tumor necrosis/ulcerated and tumor burden (Tumor volume >1500 mm3) were humanely euthanized on day 21 and necropsy was performed.

Collection of Samples

On day 21, blood sampling was carried out from remaining animals of all the treatment groups. After collection, the blood was allowed to clot for 20 minutes at room temperature. Further, the serum was separated by centrifugation at 2,000×g for 10 minutes and stored at −80° C. for further use. All animals were humanely euthanized and tumor (as per tumor availability) was harvested and divided into two parts One part of the tumor was snap frozen and the second part was fixed in 10% Neutral buffered formalin (NBF).

Results

Cetuximab, BCA101, and pembrolizumab were evaluated either as a standalone therapy or as a combination therapy (BCA101+pembrolizumab) for antitumor activity against PC-3 tumor xenografts. Cetuximab, BCA101 and pembrolizumab were administered intraperitoneally at a dose of 8.1, 10 and 10 mg/kg, respectively. Combination therapy of BCA101+pembrolizumab were tested with the same dose and regimen. All animals from all the treatment groups were alive at day 18.A such, day 18 was chosen for efficacy evaluation. Treatment with cetuximab, BCA101, pembrolizumab, and BCA101+pembrolizumab demonstrated 65%, 60%, 48% and 22% of % T/C, respectively against hu IgG1 (Isotype control) treatment group (Table 7).

TABLE 7

Effect of cetuximab, BCA101 and pembrolizumab in huNOG-EXL bearing PC-3 tumor xenograft.

| Group | Number of Animals | % Test/Control Day 18 | Statistical Analysis Day 18 | Mean % Body Weight Change Day 18 | Mortality |
|---|---|---|---|---|---|
| Group I Isotype Control | 10 | NA | — | −10% | 2/10 (Day 19-D147-A35 and day 21-D147-A2) |
| Group II Cetuximab | 10 | 65 | *** ($p < 0.001$) | −9% | — |
| Group III BCA101 | 10 | 60 | *** ($p < 0.001$) | −11% | 1/10 (Day 19-D147-A38) |
| Group IV Anti-PD1 (pembrolizumab) | 10 | 48 | *** ($p < 0.001$) | −8% | — |
| Group V BCA101 + Anti-PD1 (pembrolizumab) | 10 | 22 | *** ($p < 0.001$) | −7% | 2/10 (Day 20-D148-A9 and day 21-D149-A65) |

*** Statistically significant ($p < 0.001$) difference when respective treatment groups were compared with isotype control group. Statistical analysis carried out by Two-way ANOVA followed by Bonferroni post tests using Graph Pad Prism (Version 8.3.0).

Figure 3A:
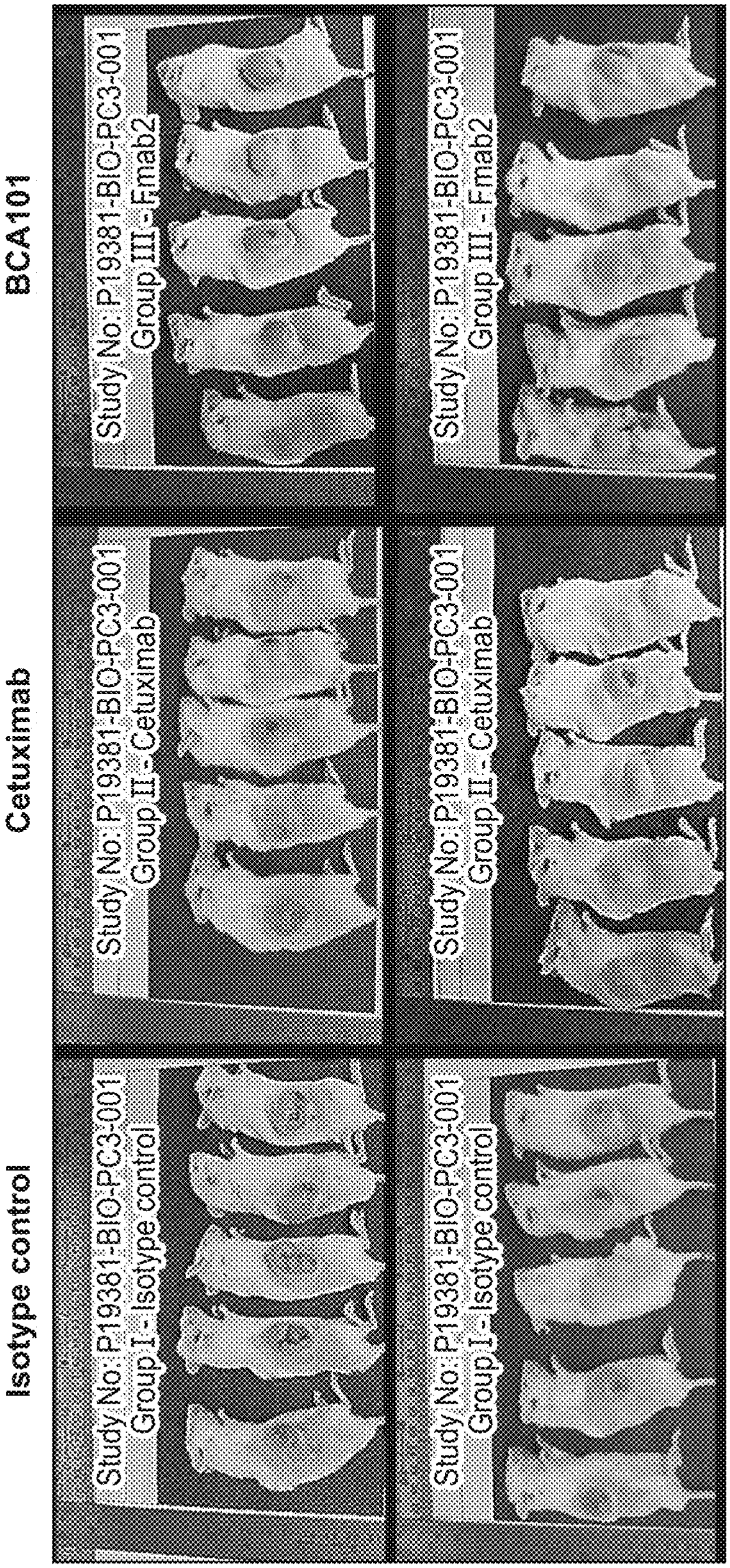
FIG. 3A shows photographs of huNOG-EXL mice bearing PC-3 tumors, from the control group (isotype control), the cetuximab treatment group, and the BCA101 treatment group. Photograph were captured on day 19 of the study.
Figure 3B:
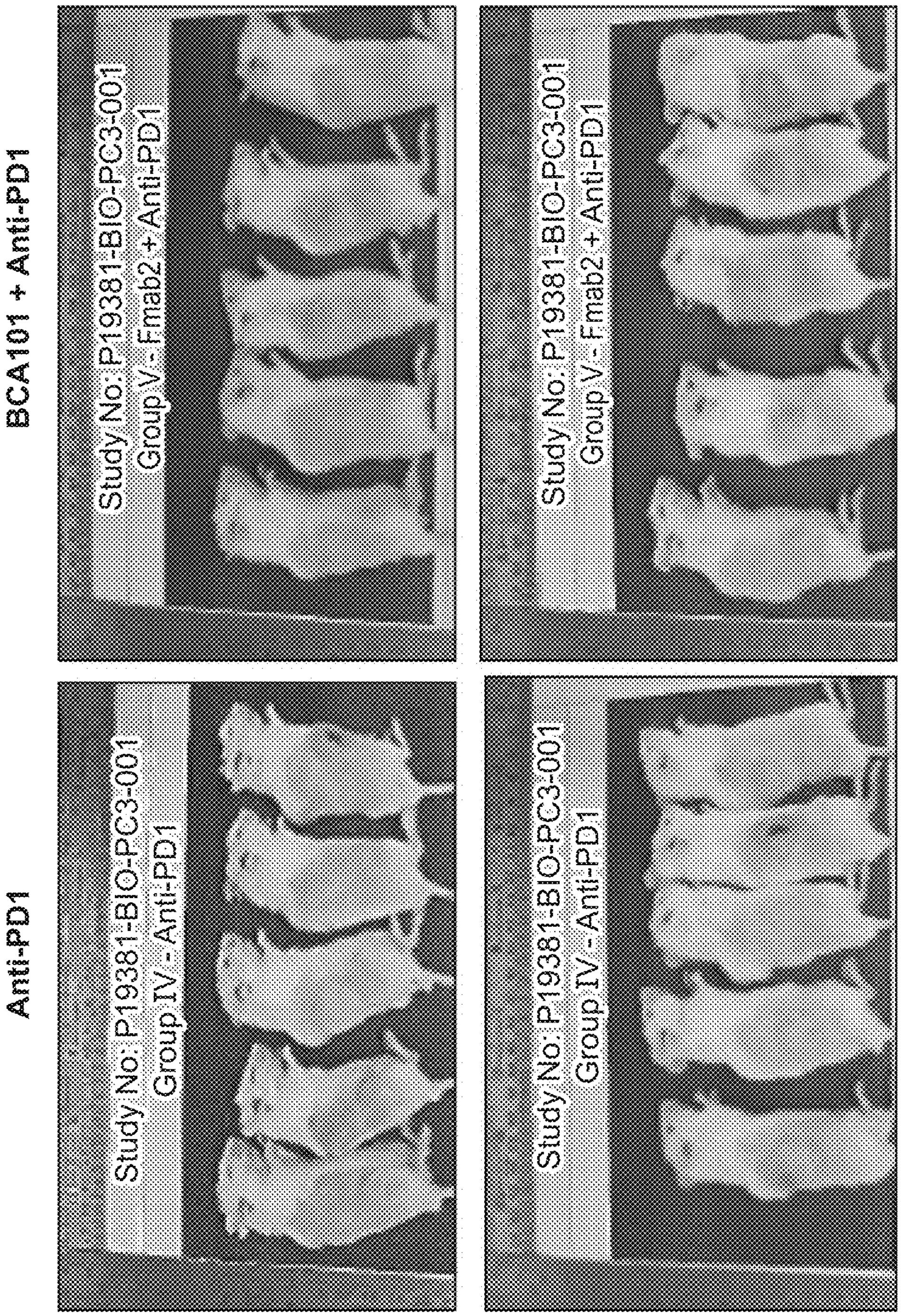
FIG. 3B shows photographs of huNOG-EXL mice bearing PC-3 tumors, from the anti-PD1 (pembrolizumab) treatment group and the BCA101+anti-PD1 (pembrolizumab) treatment group. Photograph were captured on day 19 of the study.

The isotype control group showed progressive tumor growth throughout the experiment with mean tumor volume of 1216±89 $mm^3$ on day 18 (Table 8). The mean tumor volume of cetuximab, BCA101, pembrolizumab and BCA101+pembrolizumab treated groups were recorded as 834±175, 776±127, 647±145 and 362±120 $mm^3$, respectively on day 18 respectively (Table 8). The tumor growth profile and individual tumor growth curve during this period are shown in FIG. 1 and FIGS. 2A-2E, respectively. Animals bearing PC-3 tumors were photographed on day 19 (FIG. 3A and FIG. 3B).

TABLE 8

| Mean tumor volume of animals bearing PC-3 xenograft tumors. | | | | | | | | | |
|---|---|---|---|---|---|---|---|---|---|
| | | Mean Tumor Volume ($mm^3$)* | | | | | | | |
| Group | Days | 0 | 3 | 6 | 9 | 12 | 15 | 18 | 21 |
| Group I | Mean | 119 | 155 | 270 | 473 | 630 | 814 | 1216 | 1759 |
| Isotype Control | S.E.M. | 3 | 8 | 23 | 47 | 41 | 51 | 89 | 131 |
| Group II | Mean | 119 | 143 | 220 | 333 | 450 | 551 | 834 | 1113 |
| Cetuximab | S.E.M. | 4 | 8 | 23 | 52 | 75 | 99 | 175 | 242 |
| Group III | Mean | 119 | 147 | 186 | 316 | 438 | 563 | 776 | 1041 |
| BCA101 | S.E.M. | 3 | 5 | 20 | 49 | 69 | 90 | 127 | 193 |
| Group IV | Mean | 119 | 149 | 225 | 317 | 351 | 452 | 647 | 862 |
| Anti-PD1 (pembrolizumab) | S.E.M. | 3 | 4 | 20 | 54 | 74 | 96 | 145 | 200 |
| Group V | Mean | 119 | 143 | 159 | 180 | 218 | 290 | 362 | 497 |
| BCA101 + Anti-PD1 (pembrolizumab) | S.E.M. | 2 | 4 | 22 | 36 | 57 | 82 | 120 | 185 |

*Values are expressed as mean of 8-10 animals in each group.

The % TGI values for cetuximab, BCA101, pembrolizumab and BCA101+pembrolizumab groups were calculated as 35%, 40%, 52% and 78% (Day 18), respectively (Table 9) with respect to the isotype control group. The treatment groups cetuximab, BCA101, pembrolizumab and BCA101+pembrolizumab showed significant decrease in the tumor growth ($p<0.001$; day 18) as compared to isotype control group. Partial tumor growth regression was observed in BCA101 (1/10 mouse), pembrolizumab (2/10 mice) and BCA101+pembrolizumab (4/10 mice) treatment groups. Based on tumor end points (tumor burden; tumor volume >1500 $mm^3$) and ethical reasons (tumor necrosis/ulceration), the study was terminated on day 21 and all animals were humanely euthanized.

TABLE 9

| Percentage tumor growth inhibition (% TGI) by delta of test compounds in huNOG-EXL mice bearing PC-3 tumor xenograft. | | | | | | | | |
|---|---|---|---|---|---|---|---|---|
| | % Tumor Growth Inhibition (% TGI) by delta | | | | | | | |
| Group | Day 0 | Day 3 | Day 6 | Day 9 | Day 12 | Day 15 | Day 18 | Day 21 |
| Group II Cetuximab | 0 | 35 | 34 | 40 | 35 | 38 | 35 | 39 |
| Group III BCA101 | 0 | 23 | 56 | 45 | 38 | 36 | 40 | 44 |
| Group IV Anti-PD1 (pembrolizumab) | 0 | 17 | 30 | 44 | 55 | 52 | 52 | 55 |
| Group V BCA101 + Anti-PD1 (pembrolizumab) | 0 | 33 | 73 | 83 | 81 | 75 | 78 | 77 |

Mortality and Body Weight Changes

Figure 4:
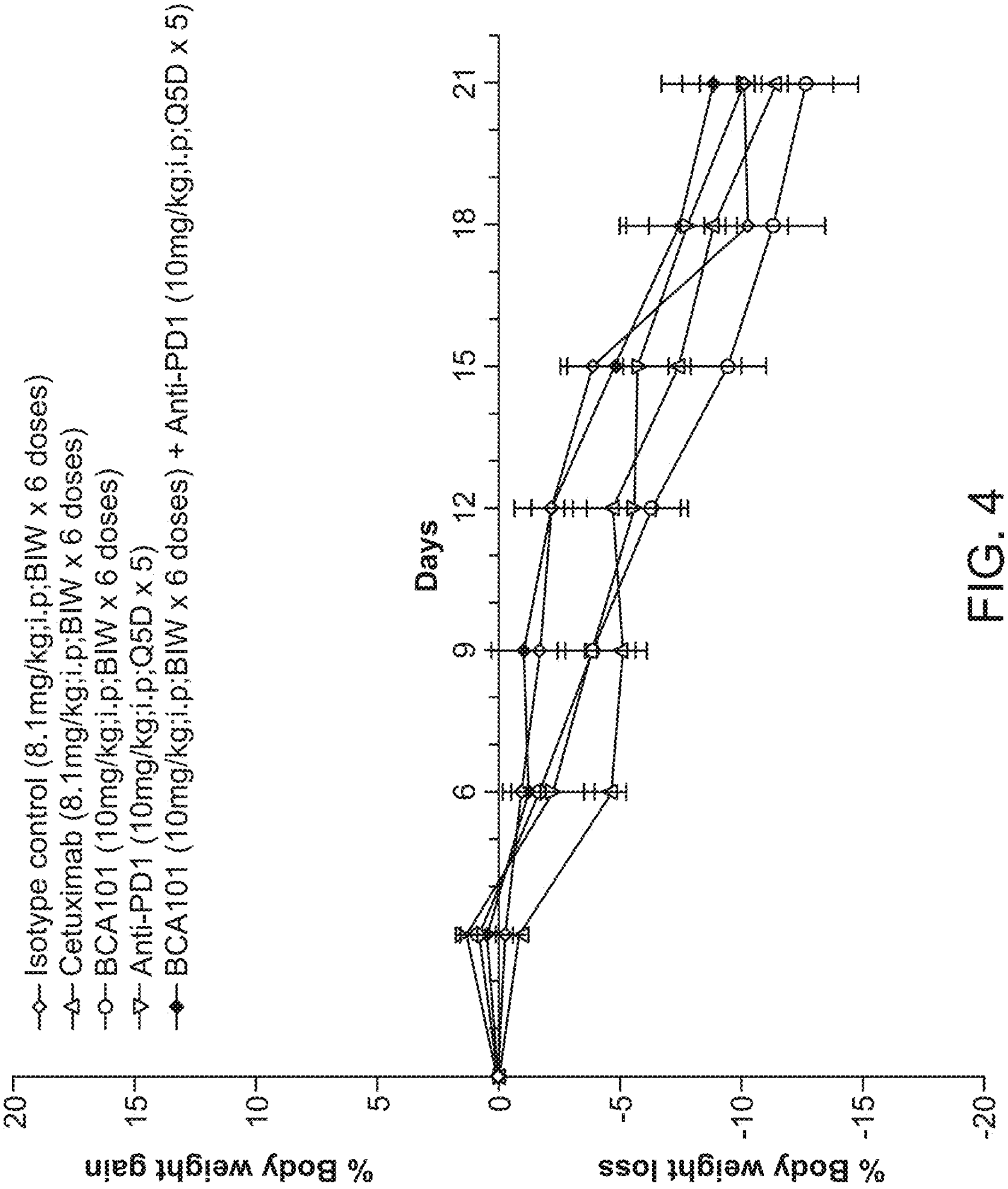
FIG. 4 is a line graph that shows the effect of cetuximab, BCA101, anti-PD1 (pembrolizumab), and BCA101+anti-PD1 (pembrolizumab) on the percentage change in body weight of huNOG-EXL mice bearing PC-3 tumor xenografts. Values are expressed as Mean±SEM of 8-10 animals in each group. There was gradual body weight loss in all the groups. There were no visible clinical signs or abnormal behavior in any of the treated groups.

Animal mortalities were observed from isotype control (Day 19-D147-A35 and day 21-D147-A2), BCA101 (Day 19-D147-A38), combination treatment BCA101+pembrolizumab (Day 20-D148-A9 and day 21-D149-A65) during the experimental period. There were no visible clinical signs of abnormal behavior observed in any of the treatment groups. Moreover, gradual decrease in body weight was observed in all the treatment groups. At the end of the study on day 21, severe weight loss (greater than −10%) was observed in all the treatment animals. The percentage change in body weight of animals for all the groups are summarized in Table 10 and FIG. 4.

TABLE 10

Mean body weight and % change in body weight of animals during PC-3 Xenograft study.

| Group | | Mean Body Weight (g) | | | | | | | |
|---|---|---|---|---|---|---|---|---|---|
| | Days | 0 | 3 | 6 | 9 | 12 | 15 | 18 | 21 |
| Group I | Mean | 25.9 | 25.8 | 25.6 | 25.4 | 25.2 | 24.8 | 23.1 | 22.8 |
| Isotype Control | S.E.M. | 1.0 | 0.9 | 0.9 | 0.8 | 0.8 | 0.8 | 0.7 | 0.6 |
| | % BWC | 0.0 | −0.3 | −1.0 | −1.8 | −2.2 | −3.8 | −10.3 | −10.2 |
| Group II | Mean | 26.9 | 26.7 | 25.7 | 25.5 | 25.6 | 24.8 | 24.4 | 23.8 |
| Cetuximab | S.E.M. | 1.1 | 1.1 | 1.0 | 1.0 | 1.0 | 0.9 | 1.0 | 0.9 |
| | % BWC | 0.0 | −0.8 | −4.6 | −5.1 | −4.6 | −7.4 | −8.8 | −11.4 |
| Group III | Mean | 26.9 | 27.0 | 26.4 | 25.8 | 25.2 | 24.3 | 23.8 | 23.7 |
| BCA101 | S.E.M. | 0.7 | 0.6 | 0.6 | 0.7 | 0.6 | 0.7 | 0.8 | 0.9 |
| | % BWC | 0.0 | 0.6 | −1.7 | −4.0 | −6.3 | −9.5 | −11.4 | −12.7 |
| Group IV | Mean | 25.1 | 25.4 | 24.5 | 24.1 | 23.6 | 23.6 | 23.1 | 22.5 |
| Anti-PD1 | S.E.M. | 0.8 | 0.7 | 0.9 | 0.9 | 0.8 | 0.8 | 0.9 | 0.9 |
| (pembrolizumab) | % BWC | 0.0 | 1.2 | −2.3 | −3.9 | −5.6 | −5.8 | −7.8 | −10.1 |
| Group V | Mean | 25.2 | 25.4 | 24.8 | 24.8 | 24.6 | 23.9 | 23.2 | 23.3 |
| BCA101 + Anti-PD1 | S.E.M. | 0.8 | 0.8 | 0.6 | 0.5 | 0.5 | 0.5 | 0.6 | 0.5 |
| (pembrolizumab) | % BWC | 0.0 | 0.8 | −1.3 | −1.1 | −2.1 | −4.9 | −7.5 | −8.9 |

* % BWC = Body weight change with respect to initial body weight of animals.

**Values are expressed as mean of 8-10 animals in each group.

CONCLUSIONS

In this PC-3 tumor xenograft model, treatment with cetuximab, BCA101, pembrolizumab and BCA101+pembrolizumab at given dose and regimen showed significant reduction in tumor growth compared to isotype control group. Among the tested dose and regimen, combination treatment (BCA101+pembrolizumab) exhibited maximum tumor growth inhibition with more number of partial tumor regression (4/10 mice) when compared to standalone treatment of pembrolizumab (partial regression-2/10 mice) and BCA101 (partial regression-1/10 mouse) followed by cetuximab (no partial tumor regression). Severe body weight loss might be attributed greatly to the tumor burden in isotype control and tested dose of treatment groups. In conclusion, BCA101 is a candidate for cancer treatment and might exhibit better efficacy in combination with immune-check point inhibitors (e.g., anti-PD1 antibodies) against various xenograft models.

Example 2. A Phase 1a/1b Dose Escalation and Cohort Expansion Study of Safety and Tolerability of BCA101 Alone and in Combination with Anti-PD1 Antibody (Pembrolizumab) in Patients with EGFR-Driven Advanced Solid Tumors Generally, this study aims to evaluate the safety, tolerability, PK, pharmacodynamics, and efficacy of BCA101 alone and in combination with pembrolizumab in patients with EGFR-driven advanced solid tumors. This is a Phase 1/1b, open-label study, which consists of dose escalation parts (Part A) followed by expansion cohorts (Part B) for both single agent BCA101 and combination BCA101 plus pembrolizumab.

Objectives

The primary objective of the dose escalation (Part A) of the study is to 1) assess the safety and tolerability of single agent BCA101 in patients with select EGFR-driven advanced solid tumors refractory to standard of care or for whom no standard of care is available; 2) assess the safety and tolerability of BCA101 in combination with pembrolizumab in patients with either squamous cell carcinoma of the head and neck (HNSCC) or squamous cell carcinoma of the anal canal (SCCAC) whose tumors are refractory to standard of care or for whom no standard of care is available; and 3) identify dose limiting toxicities (DLTs) during the first cycle of treatment with BCA101 monotherapy or the combination of BCA101 and pembrolizumab. Patients will be enrolled as per a sequential “3+3” design.

Once the maximum tolerated dose (MTD)/recommended dose (RD) is determined, the primary objective of dose expansion (Part B) is to further assess 1) the safety and tolerability of single agent BCA101 in patients with select cancers; and 2) the safety and tolerability of BCA101 in combination with pembrolizumab in patients with HNSCC and SCCAC. The patient cohorts for assessment of single agent BCA101 include 1) PD-L1 negative, EGFR-amplified Squamous Cell Lung Cancer (SqCLC); 2) RAS wild-type, microsatellite stable Colorectal Carcinoma (RAS wt, MSS CRC); 3) EGFR-amplified Triple Negative Breast Cancer; and 4) any solid tumor with either a KRAS G12D or G13D mutation.

BCA101 will be administered intravenously every 7 days at the MTD or RD based upon the results from Part A of the study. Pembrolizumab will be administered according to approved product label for use in the specific indication. The decision to proceed with each cohort will be based on the review of the cumulative safety, PK, clinical data, and any PD data, if available, and will aim to ensure that the risk-benefit ratio of the MTD or RD justifies enrollment of patients into an expansion cohort. Patients will continue with weekly infusions until disease progression, unacceptable toxicity, withdrawal of consent by the patient, or if the investigator considers it is in the best interest of a patient to discontinue treatment with the study drug.

The secondary objectives of this study are: 1) determine objective response rate in each part of the study, per RECIST v1.1 and iRECIST; 2) determine clinical benefit rate in each part of the study, per RECIST v1.1 and iRECIST; 3) determine progression free survival (PFS) in each part of the study, per RECIST v1.1 and iRECIST; 4) determine duration of response in each part of the study, per RECIST v1.1 and iRECIST; 5) determine survival rates in each part of the study; 6) AUC of BCA101 and pembrolizumab; 7) Cmax of BCA101 and pembrolizumab; 8) Tmax of BCA101 and pembrolizumab; 9) Concentration vs time profile of BCA101 and pembrolizumab; 10) Half-life of BCA101 and pembrolizumab; and 11) immunogenicity of BCA101 and pembrolizumab through the incidence and titer of anti-drug-antibodies.

Exploratory objectives of this study are to examine the pharmacodynamic markers and biomarkers for BCA101. Exploratory serum endpoints include, the levels of TGFβ1, TGFβ2, TGFβ3, soluble EGFR, VEGF, and other relevant cytokines, interleukins and chemokines. Exploratory blood cell endpoints include, the immunophenotyping by flow cytometry for multiparametric immune profiling of peripheral blood. Exploratory tumor tissue endpoints include, an analysis of archival, pre- and posttreatment biopsy samples for whole exome sequencing and next generation sequencing of DNA; immunohistochemistry for relevant EGFR and TGFβ signaling pathway markers, tumor infiltrating immune cells and other relevant markers.

Investigational Plan

Overall Design and Plan of the Study

This is a Phase 1/1b, open-label study, which consists of dose escalation parts (Part A) followed by expansion cohorts (Part B) for both single agent BCA101 and combination BCA101 plus pembrolizumab.

Dose Escalation (Part A)

Single agent BCA101 will be administered to patients via intravenous infusion weekly at a dose of 64 mg, 240 mg, 800 mg, or 1600 mg. Patients with the following tumor types will be eligible: 1) Squamous Cell Lung Cancer (SqCLC) 2) Squamous Cell Carcinoma of the Head and Neck (HNSCC) 3) RAS wild-type microsatellite stable Colorectal Carcinoma (RAS WT MSS CRC) 4) Triple Negative Breast Cancer (TNBC) 5) Chordoma 6) Squamous Cell Carcinoma of the Anal Canal (SCCAC) 7) Uveal Melanoma 8) Glioblastoma (GBM) 9) Gastric Cancer 10) Any solid tumor with a KRAS G12D or G13D mutation 11) Any solid tumor with EGFR amplification 12) Epithelial Ovarian Cancer 13) Hepatocellular Carcinoma (HCC) 14) Anaplastic Thyroid Cancer (ATC) 15) Pancreatic Cancer 16) Other EGFR-driven advanced solid tumors (if there is compelling data or evidence to enroll a patient with a tumor type other than those listed in 1-15, the treating physician may discuss the patient with the Sponsor to determine eligibility).

Combination BCA101 and pembrolizumab will be administered to patients via intravenous infusion every 3 weeks. Patients with the following tumor types will be eligible: HNSCC and SCCAC.

Cohort expansion (Part B)

Patients must have histologically or cytologically confirmed EGFR-driven, advanced solid tumor refractory to current standard of care therapy. Patients with the following tumor types will be eligible for single agent BCA101 therapy: PD-L1 negative, and EGFR-amplified SqCLC RAS WT MSS CRC EGFR-amplified TNBC, any solid tumor with a KRAS G12D or G13D mutation.

Patients with the following tumor types will be eligible for treatment with combination therapy of BCA101 and pembrolizumab:1) HNSCC 2) SCCAC.

Exclusion Criteria:

Exposure to anti-EGFR antibodies within 4 weeks of the first dose of study drug or any history of treatment with anti-TGFβ therapies.

Prior history of Grade ≥2 intolerance or hypersensitivity reaction to cetuximab or other anti-EGFR therapy or other murine proteins or prior discontinuation of therapy in the setting of toxicity related to treatment.

For Part B only: Prior history of Grade ≥2 intolerance or hypersensitivity reaction to immune checkpoint inhibitors or any history of treatment discontinuation in the setting of toxicity to an immune checkpoint inhibitor.

Pregnant or breastfeeding women.

Any condition requiring systemic treatment with either corticosteroids (>10 mg daily of prednisone or equivalent) or other immunosuppressive medication within 14 days prior to the first dose of study drug, with the exception of topical, intranasal, intrabronchial, or ocular steroids.

Known case of human immunodeficiency virus (HIV), or active hepatitis B (hepatitis B surface antigen; HBsAg) or hepatitis C.

Patients with past hepatitis B virus (HBV) infection or resolved HBV infection (defined as having a negative HBsAg test and a positive antibody to hepatitis B core antigen [anti-HBc] antibody test) are eligible. Patients positive for hepatitis C virus (HCV) antibody are eligible only if polymerase chain reaction is negative for HCV RNA.

What is claimed is:

1. A method of treating cancer in a human subject in need thereof, the method comprising administering to the subject (a) an antibody that specifically binds programmed cell death protein 1 (PD1) comprising a VH that comprises a VH CDR1, VH CDR2, and VH CDR3, wherein (i) the amino acid sequence of the VH CDR1 comprises the amino acid sequence of SEQ ID NO: 1;

(ii) the amino acid sequence of the VH CDR2 comprises the amino acid sequence of SEQ ID NO: 2; and (iii) the amino acid sequence of the VH CDR3 comprises the amino acid sequence of SEQ ID NO: 3; and a VL that comprises a VL CDR1, a VL CDR2, and a VL CDR3, wherein (i) the amino acid sequence of the VL CDR1 comprises the amino acid sequence of SEQ ID NO: 4;

(ii) the amino acid sequence of the VL CDR2 comprises the amino acid sequence of SEQ ID NO: 5; and (iii) the amino acid sequence of the VL CDR3 comprises the amino acid sequence of SEQ ID NO: 6; and (b) a fusion protein that comprises a targeting moiety and an immunomodulatory moiety, wherein: the targeting moiety comprises an antibody that specifically binds epidermal growth factor receptor (EGFR) comprising a VH that comprises a VH CDR1, VH CDR2, and VH CDR3, wherein (i) the amino acid sequence of the VH CDR1 comprises the amino acid sequence of SEQ ID NO: 34;

(ii) the amino acid sequence of the VH CDR2 comprises the amino acid sequence of SEQ ID NO: 35; and (iii) the amino acid sequence of the VH CDR3 comprises the amino acid sequence of SEQ ID NO: 36; and a VL that comprises a VL CDR1, a VL CDR2, and a VL CDR3, wherein (i) the amino acid sequence of the VL CDR1 comprises the amino acid sequence of SEQ ID NO: 37;

(ii) the amino acid sequence of the VL CDR2 comprises the amino acid sequence of SEQ ID NO: 38; and (iii) the amino acid sequence of the VL CDR3 comprises the amino acid sequence of SEQ ID NO: 39; and the immunomodulatory moiety comprises an amino acid sequence at least 95%, 96%, 97%, 98%, 99%, or 100% identical to the amino acid sequence of SEQ ID NO: 56.

2. The method of claim 1, wherein the antibody that specifically binds PD1 is a full-length antibody, a single chain variable fragment (scFv), a scFv2, a scFv-Fc, a Fab, a Fab', a F(ab') 2, or a F(v).

3. The method of claim 1, wherein the antibody that specifically binds PD1 is a full-length antibody.

4. The method of claim 1, wherein the antibody that specifically binds PD1 inhibits binding of PD1 to programmed cell death ligand protein 1 (PDL1).

5. The method of claim 1, wherein the antibody that specifically binds PD1 inhibits signaling of PD1.

6. The method of claim 1, wherein the amino acid sequence of the VH of the antibody that specifically binds PD1 comprises an amino acid sequence at least 95%, 96%, 97%, 98%, 99%, or 100% identical to the amino acid sequence of SEQ ID NO: 7; and the amino acid sequence of the VL of the antibody that specifically binds PD1 comprises an amino acid sequence at least 95%, 96%, 97%, 98%, 99%, or 100% identical to the amino acid sequence of SEQ ID NO: 8.

7. The method of claim 1, wherein the antibody that specifically binds PD1 comprises a heavy chain, wherein the amino acid sequence of the heavy chain comprises an amino acid sequence at least 95%, 96%, 97%, 98%, 99%, or 100% identical to the amino acid sequence of SEQ ID NO: 9; and a light chain, wherein the amino acid sequence of the light chain comprises an amino acid sequence at least 95%, 96%, 97%, 98%, 99%, or 100% identical to the amino acid sequence of SEQ ID NO: 11.

8. The method of claim 1, wherein the antibody that specifically binds EGFR is a full-length antibody, a single chain variable fragment (scFv), a scFv2, a scFv-Fc, a Fab, a Fab', a F(ab') 2, or a F(v).

9. The method of claim 1, wherein the antibody that specifically binds EGFR is a full-length antibody.

10. The method of claim 1, wherein the amino acid sequence of the VH of the antibody that specifically binds EGFR comprises an amino acid sequence at least 95%, 96%, 97%, 98%, 99%, or 100% identical to the amino acid sequence of SEQ ID NO: 40;

and the amino acid sequence of the VL of the antibody that specifically binds EGFR comprises an amino acid sequence at least 95%, 96%, 97%, 98%, 99%, or 100% identical to the amino acid sequence of SEQ ID NO: 41.

11. The method of claim 1, wherein the antibody that specifically binds EGFR comprises a heavy chain, wherein the amino acid sequence of the heavy chain comprises an amino acid sequence at least 95%, 96%, 97%, 98%, 99%, or 100% identical to the amino acid sequence of SEQ ID NO: 43; and a light chain, wherein the amino acid sequence of the light chain comprises an amino acid sequence at least 95%, 96%, 97%, 98%, 99%, or 100% identical to the amino acid sequence of SEQ ID NO: 44.

12. The method of claim 1, wherein the amino acid sequence of the immunomodulatory moiety consists of an amino acid sequence at least 95%, 96%, 97%, 98%, 99%, or 100% identical to the amino acid sequence of SEQ ID NO: 56.

13. The method of claim 1, wherein the immunomodulatory moiety is indirectly fused to the targeting moiety via a peptide linker.

14. The method of claim 13, wherein the amino acid sequence of the linker comprises the amino acid sequence of SEQ ID NO: 57, 58, 59, 60, or 61.

15. The method of claim 13, wherein the amino acid sequence of the linker comprises the amino acid sequence of SEQ ID NO: 57.

16. The method of claim 13, wherein the amino acid sequence of the linker consists of the amino acid sequence of SEQ ID NO: 57.

17. The method of claim 1, wherein the targeting moiety is a full length antibody that comprises a light chain and a heavy chain, and wherein the immunomodulatory moiety is fused to the C terminus of the heavy chain of the targeting moiety.

18. The method of claim 1, wherein the targeting moiety is a full length antibody that comprises a light chain and a heavy chain, and wherein the immunomodulatory moiety is fused to the C terminus of the light chain of the targeting moiety.

19. The method of claim 1, wherein the targeting moiety is an antibody specifically binds EGFR that comprises a heavy chain, wherein the amino acid sequence of the heavy chain comprises an amino acid sequence at least 95%, 96%, 97%, 98%, 99%, or 100% identical to the amino acid sequence of SEQ ID NO: 43, and a light chain, wherein the amino acid sequence of the light chain comprises an amino acid sequence at least 95%, 96%, 97%, 98%, 99%, or 100% identical to the amino acid sequence of SEQ ID NO: 44,and wherein the amino acid sequence of the immunomodulatory moiety comprises an amino acid sequence at least 95%, 96%, 97%, 98%, 99%, or 100% identical to the amino acid sequence of SEQ ID NO: 56, and wherein the N terminus of the immunomodulatory moiety is fused indirectly through a linker to the C terminus of the heavy chain or the light chain, and wherein the amino acid sequence of the linker comprises an amino acid sequence at least 95%, 96%, 97%, 98%, 99%, or 100% identical to the amino acid sequence of SEQ ID NO: 57.

20. The method of claim 1, wherein the targeting moiety is an antibody specifically binds EGFR that comprises a heavy chain, wherein the amino acid sequence of the heavy chain comprises an amino acid sequence at least 95%, 96%, 97%, 98%, 99%, or 100% identical to the amino acid sequence of SEQ ID NO: 43, and a light chain, wherein the amino acid sequence of the light chain comprises an amino acid sequence at least 95%, 96%, 97%, 98%, 99%, or 100% identical to the amino acid sequence of SEQ ID NO: 44,and wherein the amino acid sequence of the immunomodulatory moiety comprises an amino acid sequence at least 95%, 96%, 97%, 98%, 99%, or 100% identical to the amino acid sequence of SEQ ID NO: 56, and wherein the N terminus of the immunomodulatory moiety is fused indirectly through a linker to the C terminus of the light chain, and wherein the linker, wherein the amino acid sequence of the linker comprises an amino acid sequence at least 95%, 96%, 97%, 98%, 99%, or 100% identical to the amino acid sequence of SEQ ID NO: 57.

21. The method of claim 1, wherein the fusion protein comprises an antibody that comprises a heavy chain, wherein the amino acid sequence of the heavy chain comprises an amino acid sequence at least 95%, 96%, 97%, 98%, 99%, or 100% identical to the amino acid sequence of SEQ ID NO: 43; and a light chain, wherein the amino acid sequence of the light chain comprises an amino acid sequence at least 95%, 96%, 97%, 98%, 99%, or 100% identical to the amino acid sequence of SEQ ID NO: 62.

22. The method of claim 1, wherein the fusion protein comprises an antibody that comprises a heavy chain, wherein the amino acid sequence of the heavy chain comprises the amino acid sequence of SEQ ID NO: 43; and a light chain, wherein the amino acid sequence of the light chain comprises the amino acid sequence of SEQ ID NO: 62; and the antibody that specifically binds PD1 comprises a heavy chain, wherein the amino acid sequence of the heavy chain region comprises the amino acid sequence of SEQ ID NO: 10; and a light chain region, wherein the amino acid sequence of the light chain region comprises the amino acid sequence of SEQ ID NO: 11.

23. The method of claim 1, wherein the cancer is a solid tumor.

24. The method of claim 1, wherein the cancer is breast cancer, anal cancer, pancreatic cancer, thyroid cancer, liver cancer, ovarian cancer, lung cancer, skin cancer, brain cancer, spinal cord cancer, head cancer, neck cancer, or head and neck cancer.

25. The method of claim 1, wherein the cancer is head and neck cancer.

26. The method of claim 25, wherein the cancer is head and neck squamous cell carcinoma (HNSCC).

27. A method of treating cancer in a human subject in need thereof, the method comprising administering to the subject (a) an antibody that specifically binds programmed cell death protein 1 (PD1) comprising a VH comprising a VH CDR1, a VH CDR2, and a VH CDR3 and a VL comprising a VL CDR1,a VL CDR2, and a VL CDR3, wherein
  a. the amino acid sequence of the VH CDR1 comprises the amino acid sequence of SEQ ID NO: 1;
  b. the amino acid sequence of the VH CDR2 comprises the amino acid sequence of SEQ ID NO: 2;
  c. the amino acid sequence of the VH CDR3 comprises the amino acid sequence of SEQ ID NO: 3;
  d. the amino acid sequence of the VL CDR1 comprises the amino acid sequence of SEQ ID NO: 4;
  e. the amino acid sequence of the VL CDR2 comprises the amino acid sequence of SEQ ID NO: 5; and
  f. the amino acid sequence of the VL CDR3 comprises the amino acid sequence of SEQ ID NO: 6; and (b) a fusion protein that comprises a targeting moiety indirectly operably connected to an immunomodulatory moiety via a peptide linker, wherein: i) the targeting moiety specifically binds epidermal growth factor receptor (EGFR); and (ii) the immunomodulatory moiety comprises an amino acid sequence of the extracellular domain of transforming growth factor-beta receptor II (TGFβRII); and wherein the targeting moiety comprises a full length antibody comprising a heavy chain and a light chain; wherein the amino acid sequence of the heavy chain comprises an amino acid sequence at least 95%, 96%, 97%, 98%, 99%, or 100% identical to the amino acid sequence set forth in SEQ ID NO: 42; wherein the amino acid sequence of the light chain comprises an amino acid sequence at least 95%, 96%, 97%, 98%, 99%, or 100% identical to the amino acid sequence set forth in SEQ ID NO: 44;

wherein the amino acid sequence of the immunomodulatory moiety comprises an amino acid sequence at least 95%, 96%, 97%, 98%, 99%, or 100% identical to the amino acid sequence set forth in SEQ ID NO: 56; and wherein the amino acid sequence of the peptide linker comprises an amino acid sequence at least 95%, 96%, 97%, 98%, 99%, or 100% identical to the amino acid sequence set forth in SEQ ID NO: 57; and wherein the immunomodulatory moiety is operably connected to the C-terminus of the light chain of the targeting moiety.

28. A method of treating cancer in a human subject in need thereof, the method comprising administering to the subject (a) an antibody that specifically binds programmed cell death protein 1 (PD1) comprising a VH comprising a VH CDR1, a VH CDR2, and a VH CDR3 and a VL comprising a VL CDR1,a VL CDR2, and a VL CDR3, wherein
  a. the amino acid sequence of the VH CDR1 comprises the amino acid sequence of SEQ ID NO: 1;
  b. the amino acid sequence of the VH CDR2 comprises the amino acid sequence of SEQ ID NO: 2;
  c. the amino acid sequence of the VH CDR3 comprises the amino acid sequence of SEQ ID NO: 3;
  d. the amino acid sequence of the VL CDR1 comprises the amino acid sequence of SEQ ID NO: 4;
  e. the amino acid sequence of the VL CDR2 comprises the amino acid sequence of SEQ ID NO: 5; and
  f. the amino acid sequence of the VL CDR3 comprises the amino acid sequence of SEQ ID NO: 6; and (b) a fusion protein that comprises a targeting moiety indirectly operably connected to an immunomodulatory moiety via a peptide linker, wherein: i) the targeting moiety specifically binds epidermal growth factor receptor (EGFR); and (ii) the immunomodulatory moiety comprises an amino acid sequence of the extracellular domain of transforming growth factor-beta receptor II (TGFβRII); and wherein the targeting moiety comprises a full length antibody comprising a heavy chain and a light chain; wherein the amino acid sequence of the heavy chain comprises the amino acid sequence set forth in SEQ ID NO: 42; wherein the amino acid sequence of the light chain comprises the amino acid sequence set forth in SEQ ID NO: 44;

wherein the amino acid sequence of the immunomodulatory moiety comprises the amino acid sequence set forth in SEQ ID NO: 56; and wherein the amino acid sequence of the peptide linker comprises the amino acid sequence set forth in SEQ ID NO: 57; and wherein the immunomodulatory moiety is operably connected to the C-terminus of the light chain of the targeting moiety.

* * * * *